United States Patent
Chevrier et al.

(10) Patent No.: US 10,765,724 B2
(45) Date of Patent: Sep. 8, 2020

(54) METHOD OF TREATING PSORIASIS WITH INCREASED INTERVAL DOSING OF ANTI-IL12/23 ANTIBODY

(71) Applicant: Janssen Biotech, Inc., Horsham, PA (US)

(72) Inventors: Marc Chevrier, Spring House, PA (US); Kamyar Farahi, Spring House, PA (US); Newman Yeilding, Spring House, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 15/471,790

(22) Filed: Mar. 28, 2017

(65) Prior Publication Data

US 2018/0036379 A1 Feb. 8, 2018

Related U.S. Application Data

(60) Provisional application No. 62/314,697, filed on Mar. 29, 2016.

(51) Int. Cl.
| | | |
|---|---|---|
| *A61K 38/20* | (2006.01) | |
| *A61K 39/395* | (2006.01) | |
| *C07K 16/24* | (2006.01) | |
| *A01K 67/027* | (2006.01) | |
| *A61K 39/00* | (2006.01) | |
| *C07K 14/54* | (2006.01) | |
| *A61K 35/12* | (2015.01) | |

(52) U.S. Cl.
CPC ........ *A61K 38/208* (2013.01); *A01K 67/0271* (2013.01); *A61K 38/20* (2013.01); *A61K 39/00* (2013.01); *A61K 39/3955* (2013.01); *C07K 14/5434* (2013.01); *C07K 16/244* (2013.01); *A61K 35/12* (2013.01); *A61K 2035/122* (2013.01); *A61K 2039/505* (2013.01); *A61K 2039/507* (2013.01); *A61K 2039/545* (2013.01); *C07K 16/24* (2013.01); *C07K 2317/34* (2013.01); *C07K 2317/55* (2013.01)

(58) Field of Classification Search
None
See application file for complete search history.

(56) References Cited

PUBLICATIONS

Longbrake et al, Expert Rev. Neurother. 9(3), 319-321 (2009).*
Systemic Lupus Erythematosus, Merck Manuals Professional Edition, 2018.*
Lung and Heart-Lung Transpl; Merck Manuals Professional Edition; 2018.*
Cystic Fibrosis; Merck Manuals Professional Edition; 2018.*
Leonardi et al; Lancet 2008; vol. 371, pp. 1665-1674.*
Langley et al, (British Journal of Dermatology, (2015) ; vol. 172, pp. 1371-1383) first Published on Oct. 11, 2014.*
Warne et al, (European Journal of Pharmaceutics and Biopharmaceutics; 2011; vol. 78, pp. 208-212).*
Healy, et al., "Comparison of hospitalization and serious infections rates among patients with moderate-to-severe osoriasis treated with ustekinumab: Comparisons to a large healthcare claims database", ODAC, Previously presented, (Jan. 2010) (Abstract Only).
Leonardi, et al., "Sustained Improvement in Skin Disease-Specific Quality of Life in Patients with Moderate to Severe Psoriasis Receiving Ustekinumab Maintenance Therapy: Long Term Results from PHOENIX 1", ISPOR Annual, New, (May 2010) (Abstract Only).
Leonardi, et al., "Sustained Improvement in Skin Disease-Specific Quality of Life in Patients with Moderate to Severe Psoriasis Receiving Ustekinumab Maintenance Therapy: Long Term Results from PHOENIX 1", EADV Fall, Previously presented, (Oct. 2010) (Abstract Only).
Leonardi, et al., "Sustained Improvement in Skin Disease-Specific Quality of Life in Patients with Moderate to Severe Psoriasis Receiving Ustekinumab Maintenance Therapy: Long Term Results from PHOENIX 1", AAD Winter, Previously presented, (Feb. 2011) (Abstract Only).
Kimball, et al., "Marked Long-term Clinical Response To Treatment With Ustekinumab, A New Monoclonal Antibody For The Treatment Of Psoriasis [previously presented]", AAD Summer, (Jul.-Aug. 2008) (Abstract Only).
Kimball, et al., "Marked Long-Term Clinical Response to Treatment With Ustekinumab, a New Monoclonal Antibody for the Treatment Of Psoriasis", BAD, (Jul.-Aug. 2008) (Abstract Only).
Reich, et al., "PSS28 Long-Term Improvement in Patient-Reported Outcomes After Transition From Methotrexate to Ustekinumab in Moderate to Severe Psoriasis: TRANSIT Week 52 Results", Value in Health, ISPOR Europe, vol. 15, No. 7: A573, (2012) (Abstract Only).
Leonardi, et al., "Characterization of Infections Associated with Ustekinumab in Moderate to Severe Psoriasis Patients", EADV Fall, Previously presented, (Oct. 2010) (Abstract Only).
Kimball, et al., "Efficacy And Safety Of Ustekinumab, An Anti-IL-12/23p40 Antibody, For The Treatment of Moderate-to-Severe Psoriasis [previously presented]", AAD Summer, (Jul.-Aug. 2008) (Abstract Only).
Kimball, et al., "Marked Long-term Clinical Response To Treatment With Ustekinumab, A New Monoclonal Antibody For The Treatment Of Psoriasis [previously presented]", Winter Clinical Derm, (2008) (Abstract Only).
Rich, et al., "Ustekinumab demonstrates rapid onset of efficacy in the treatment of moderate-to-severe psoriasis", CPIN ICOP, New, (Jul. 2010) (Abstract Only).

(Continued)

*Primary Examiner* — Bridget E Bunner
*Assistant Examiner* — Fozia Hamud
(74) *Attorney, Agent, or Firm* — Eric Dichter

(57) ABSTRACT

A method of treating an IL-12/23-related disease in a patient using an increasing dosing interval, comprises increasing the dosing interval of IL-12/IL-23 antibody to a patient, wherein the antibody is administered initially and after 4 weeks, after 16 weeks and after 28 weeks, and increasing the dosing interval after 28 weeks to an increased interval, e.g., every 16, 20 or 24 weeks.

9 Claims, 9 Drawing Sheets

Specification includes a Sequence Listing.

(56) References Cited

PUBLICATIONS

Carter, et al., "Real-World Treatment Patterns for the First Year of Ustekinumab Therapy in Patients with Moderate-to-Severe Psoriasis", AAD Winter, (Mar. 2013) (Abstract Only).
Gordon, et al., "The Ustekinumab Safety Experience in Patients With Moderate-to-Severe Psoriasis: Results From Pooled Analyses of Phase 2 and Phase 3 Clinical Trial Data", Hawaii Derm, Previously presented, (Feb. 2010) (Abstract Only).
Odom D., et al., "PSY9—A network meta-analysis of randomized, controlled trials of ustekinumab and adalimumab for moderate-to-severe psoriasis", Value in Health, vol. 16, No. 3: A112, (2013) (Abstract Only).
Rich, et al., "Ustekinumab demonstrates rapid onset of efficacy in the treatment of moderate-to-severe psoriasis", AAD Winter, Previously presented, (Feb. 2011) (Abstract Only).
Leonardi, et al., "Characterization of Infections Associated with Ustekinumab in Moderate to Severe Psoriasis Patients", AAD Summer, Previously presented, (Aug. 2010). (Abstract Only).
Landells, et al., "Safety and efficacy of ustekinumab in adolescent patients with moderate to severe plaque psoriasis: Results through 1 year of the phase 3 CADMUS trial", Journal of the American Academy of Dermatology, vol. 75, No. 5: AB202, (2015) (Abstract Only).
Papp, et al., "Malignancies in Ustekinumab-Treated Psoriasis Patients: Comparisons to the General United States Population [previously presented]", BAD, (Jul. 2009) (Abstract).
Shakery et al., "Efficacy and safety of ustekinumab for psoriasis vulgaris in German patients—A subanalysis of the PHOENIX 2 study", CPIN ICOP, New, (Jul. 2010) (Abstract Only).
Leonardi, et al., "Characterization of Infections Associated with Ustekinumab in Moderate to Severe Psoriasis Patients", CPIN ICOP, New, (Jul. 2010) (Abstract Only).
Guenther, et al., "Impact of ustekinumab on quality of life and sexual difficulties associated with psoriasis: Results from Phase 3 clinical trials", Previously presented, AAD Winter, (Mar. 2010) (Abstract Only).
Prinz, et al., "Ustekinumab Has a Consistent Efficacy and Safety Profile in Patients With Moderate to Severe Psoriasis: Results From the PHOENIX 1 and 2 Clinical Trial Program [previously presented]", BAD, (Jul. 2009) (Abstract Only).
Gordon, et al., "Infection rates in Ustekinumab-treated psoriasis patients: observations with up to 3 years of follow-up and comparisons to a large health care claims database", Journal of the European Academy of Dermatology and Venereology, CPIN ICOP, vol. 24, S4, pp. 23-24 (2010) (Abstract Only).
Sofen, et al., "Ustekinumab Improves Overall Skin Response and Health-Related Quality of Life in a Subset of Moderate to Severe Psoriasis Patients With Psoriatic Arthritis: Analysis of PHOENIX 1 and 2", ISPOR Annual, New, (May 2010) (Abstract Only).
Zhu, et al., "Marked Clinical Responses in Asian Patients with Moderate to Severe Psoriasis Treated with Ustekmumab: Results from the LOTUS, PEARL, and Japanese Clinical Studies", ADC, (Jul. 2013) (Abstract Only).
Lebwohl, et al., "Two Doses of Subcutaneous Ustekinumab Based on Body Weight Provides Similar Efficacy in Heavier and Lighter Weight Patients With Moderate-to-Severe Psoriasis", Hawaii Derm, Previously presented, (Feb. 2010) (Abstract Only).
Sofen, et al., "Ustekinumab improves overall skin response and health-related quality of life in a subset of moderate to severe psoriasis patients with psoriatic arthritis: Analysis of PHOENIX 1 and 2", Journal of the American Academy of Dermatology, AAD Winter, vol. 64, No. 2 :AB156, (2011) (Abstract Only).
Papp, et al., "Malignancies in Ustekinumab-Treated Psoriasis Patients: Comparisons to the General United States Population", Winter Clinical Derm, Previously presented, (Jan. 2010) (Abstract Only).
Papp, et al., "Malignancies in Ustekinumab-Treated Psoriasis Patients: Comparisons to the General United States Population", Previously presented, ODAC, (Jan. 2010) (Abstract Only).
Papp, et al., "Malignancies in Ustekinumab-Treated Psoriasis Patients: Comparisons to the General United States Population", Maui Derm, Previously presented, (Jan. 2010) (Abstract Only).
Papp, et al., "Malignancies in Ustekinumab-Treated Psoriasis Patients: Comparisons to the General United States Population", AAD Summer, (Jul.-Aug. 2009) (Abstract Only).
Gordon, et al., "The ustekinumab safety experience in patients with moderate-to-severe psoriasis: Results from pooled analyses of Phase 2 and Phase 3 clinical trial data", Caribbean Derm, Previously presented, (Jan. 2010) Abstract Only).
Langley, et al., "Efficacy of switching from ustekinumab to guselkumab in patients with moderate-to-severe plaque psoriasis: Results from the NAVIGATE study", Journal of the American Academy of Dermatology, vol. 76, No. 6: AB120, (2017) (Abstract Only).
Schenkel, et al., "Ustekinumab Is Associated With Significant Improvements In Overall Health-Related Quality Of Life In Moderate-To-Severe Psoriasis Patients", Value in Health, ISPOR Latin America, vol. 12, No. 7: A528 (2009) (Abstract Only).
Papp, et al., "Malignancies in Ustekinumab-Treated Psoriasis Patients: Comparisons to the General United States Population", Hawaii Derm, Previously presented, (Feb. 2010) (Abstract Only).
Ritchlin, et al., "Maintenance of efficacy and safety of ustekinumab in patients with active psoriatic arthritis despite prior conventional nonbiologic and anti-TNF biologic therapy: 1 year results of a phase 3, multicenter, double-blind, placebo-controlled trial", Arthritis & Rheumatism, vol. 65, S10 :S127-S128 (2013) (Abstract Only).
Zhang, et al., "Patient-reported treatment satisfaction and choice of dosing frequency with biologic treatment for moderate to severe plaque psoriasis", Patient Preference and Adherence, vol. 8, pp. 777-784 (2015).
Singh, et al., "Effect of Age of Onset of Psoriasis on Clinical Outcomes with Systemic Treatment in the Psoriasis Longitudinal Assessment and Registry (PSOLAR)", American Journal of Clinical Dermatology, vol. 19, No. 6, pp. 879-886 (2018).
Kavanaugh, et al., "Efficacy and safety of ustekinumab in psoriatic arthritis patients with peripheral arthritis and physician-reported spondylitis: post-hoc analyses from two phase III, multicentre, double-blind, placebo-controlled studies (PSUMMIT-1/PSUMMIT-2)", Annals of the Rheumatic Diseases, vol. 75, No. 11, pp. 1984-1988, (2016).
Rahman, et al., "Ustekinumab Treatment and Improvement of Physical Function and Health Related Quality of Life in Patients With Psoriatic Arthritis", Arthritis Care & Research, vol. 68, No. 12, pp. 1812-1822 (2016).
Kalb, et al., "Risk of Serious Infection With Biologic and Systemic Treatment of Psoriasis: Results From the Psoriasis Longitudinal Assessment and Registry (PSOLAR)", JAMA Dermatology, vol. 151, No. 9, pp. 961-969, (2015).
Reich, et al., "Cardiovascular Safety in the Ustekinumab Clinical Development Program: Final Update with up to 5 Years of Follow-Up", Journal of the American Academy of Dermatology, vol. 68, 4 Suppl:AB194 (2013) (Abstract only).
Kavanaugh, et al., "Maintenance of Clinical Efficacy and Radiographic Benefit Through Two Years of Ustekinumab Therapy in Patients With Active Psoriatic Arthritis: Results From a Randomized, Placebo-Controlled Phase III Trial", Arthritis Care & Research, vol. 67, No. 12, pp. 1739-1749, (2015).
Han, et al., "Increased prevalence of psychiatric disorders and health care-associated costs among patients with moderate-to-severe psoriasis", Journal of drugs in dermatology, vol. 10, No. 8, pp. 843-850, (2010).
Gottlieb, et al., "Ustekinumab, a human interleukin 12/23 monoclonal antibody, for psoriatic arthritis: randomised, double-blind, placebo-controlled, crossover trial", Lancet, vol. 373, pp. 633-640, (2009).
Gottlieb, et al., "Ustekinumab in patients with active psoriatic arthritis: Results of the phase III, multicenter, double-blind, placebo-controlled PSUMMIT I study", Journal of the American Academy of Dermatology, vol. 68, 4 Suppl 1: AB218, (2013) (Abstract Only).
Zhu, et al. "Comparison of the Pharmacokinetics of Subcutaneous Ustekinumab between Chinese and Non-Chinese Healthy Male Subjects across Two Phase 1 Studies", Clinical Drug Investigation, vol. 33, No. 4, pp. 291-301, (2013).

(56) References Cited

PUBLICATIONS

Kavanaugh, et al., "Effect of ustekinumab on physical function and health-related quality of life in patients with psoriatic arthritis: a randomized, placebo-controlled, phase II trial", Current Medical Research and Opinion, vol. 26, No. 10, pp. 2385-2392, (2010).

Bissonnette, et al., "Evaluation of Risk of Major Adverse Cardiovascular Events With Biologic Therapy in Patients With Psoriasis", Journal of drugs in dermatology JDD, vol. 16, No. 10, pp. 1002-1013, (2017).

Benson, et al., "Discovery and mechanism of ustekinumab: A human monoclonal antibody targeting Interleukin-12 and Interleukin-23 for treatment of immune-mediated disorders", mAbs, vol. 3, No. 6, pp. 535-545, (2011).

Elliot, et al., "Ustekinumab: Lessons Learned from Targeting Interleukin-12/23p40 in Immune-Mediated Diseases", Annals of the New York Academy of Sciences, vol. 1182, pp. 97-110, (2009).

Frieder, et al., "Secukinumab: a review of the anti-IL-17A biologic for the treatment of psoriasis [Review]", Therapeutic Advances in Chronic Disease, vol. 9, No. 1, pp. 5-21, (2018).

Benson, et al., "Therapeutic targeting of the IL-12/23 pathways: generation and characterization of ustekinumab", Nature Biotechnology, vol. 29, No. 7, pp. 615-624, (2011).

Hu, et al., "Information contributed by meta-analysis in exposure-response modeling: application to phase 2 dose selection of guselkumab in patients with moderate-to-severe psoriasis", Journal of Pharmacokinetics and Pharmacodynamics, vol. 41, No. 3, pp. 239-250, (2014).

Tsai, et al., "A case of latent tuberculosis reactivation in a patient treated with ustekinumab without concomitant isoniazid chemoprophylaxis in the PEARL trial [Letter]", British journal of dermatology, vol. 168, No. 2, pp. 444-446 (2013).

Menter, et al., "Drug survival of biologic therapy in a large, disease-based registry of patients with psoriasis: results from the Psoriasis Longitudinal Assessment and Registry (PSOLAR)", Journal of the European Academy of Dermatology and Venereology, vol. 30, No. 7, pp. 1148-1158, (2016).

Smolen, et al., "A randomised phase II study evaluating the efficacy and safety of subcutaneously administered ustekinumab and guselkumab in patients with active rheumatoid arthritis despite treatment with methotrexate", Annals of the Rheumatic Diseases, vol. 76, No. 5, pp. 831-839 (2017).

Ritchlin, et al., "Efficacy and safety of the anti-IL-12/23 p40 monoclonal antibody, ustekinumab, in patients with active psoriatic arthritis despite conventional non-biological and biological anti-tumour necrosis factor therapy: 6-month and 1-year results of the phase 3, multicentre, double-blind, placebo-controlled, randomised PSUMMIT 2 trial", Annals of the Rheumatic Diseases, vol. 73, No. 6, pp. 990-999 (2014).

Zhu, et al., "Population pharmacokinetics of ustekinumab in patients with active psoriatic arthritis", International Journal of Clinical Pharmacology and Therapeutics, vol. 48, pp. 830-846, (2010).

Gottlier, et al., "Safety Observations in 12095 Patients With Psoriasis Enrolled in an International Registry (PSOLAR): Experience With Infliximab and Other Systemic and Biologic Therapies", Journal of Drugs in Dermatology, vol. 13, No. 13, pp. 1441-1448, (2014).

Mcinnes, et al., "Efficacy and safety of ustekinumab in patients with active psoriatic arthritis: 1 year results of the phase 3, multicentre, double-blind, placebo-controlled PSUMMIT 1 trial", Lancet, vol. 382, No. 9894, pp. 780-789, (2013).

Fiorentino, et al., "Risk of malignancy with systemic psoriasis treatment in the Psoriasis Longitudinal Assessment Registry", Journal of the American Academy of Dermatology, vol. 77, No. 5, pp. 845-854, e5 (2017).

Strober, et al., "Comparative effectiveness of biologic agents for the treatment of psoriasis in a real-world setting: Results from a large, prospective, observational study (Psoriasis Longitudinal Assessment and Registry [PSOLAR]", Journal of the American Academy of Dermatology, vol. 74, No. 5, pp. 851-861, e4 (2016).

Lee, et al., "Evaluating the Effect of Treatment Persistence on the Economic Burden of Moderate to Severe Psoriasis and/or Psoriatic Arthritis Patients in the U.S. Department of Defense Population", Journal of managed care & specialty pharmacy, vol. 24, No. 7, pp. 654-663, (2018).

Greenspan, et al., "Risk of malignancies associated with ustekinumab [Letter]", British Journal of Dermatology, vol. 178, No. 1, pp. 299-300, (2018).

Kimball, et al., "Correlation of psoriasis activity with socioeconomic status: cross-sectional analysis of patients enrolled in the Psoriasis Longitudinal Assessment and Registry (PSOLAR) [Research Letter]", British Journal of Dermatology, vol. 179, No. 4, pp. 984-986, (2018).

Cameron, et al., "Importance of properly adjusting for heterogeneity among network meta-analyses considering putcomes with multiple pre-defined levels: an illustrative example in psoriasis", (Abstract Only), 2018.

Pilon, et al., "The economic burden of psoriasis with high comorbidity among privately insured patients in the United States", Journal of Medical Economics (2018).

Wu, et al., "Treatment Adherence and Persistence of Five Commonly Prescribed Medications for Moderate-to-Severe Psoriasis in a US Commercial Population", (Mar. 2019) (Abstract Only).

Kavanaugh, et al., "Demography, baseline disease characteristics, and treatment history of psoriasis patients with self-reported psoriatic arthritis enrolled in the PSOLAR registry", BMC Rheumatology, vol. 2, No. 1, pp. 29, (2018).

Strober, et al., "Depressive symptoms, depression, and the effect of biologic therapy among patients in Psoriasis Longitudinal Assessment and Registry (PSOLAR)", Journal of the American Academy of Dermatology, vol. 78, No. 1, pp. 70-80 (2018).

Reich, et al., "Safety of guselkumab in patients with moderate-to-severe psoriasis treated through 100 weeks: a pooled analysis from the randomised VOYAGE 1 and VOYAGE 2 studies", British Journal of Dermatology (2018).

Krueger, et al., "A Human Interleukin-12/23 Monoclonal Antibody for the Treatment of Psoriasis", New England Journal of Medicine, vol. 356, pp. 580-592, (2007).

Brodmerkel, et al., "Immune response to pneumococcus and tetanus toxoid in patients with moderate-to-severe psoriasis following long-term ustekinumab use", Journal of drugs in dermatology, JDD, vol. 12, No. 10, pp. 1122-1129, (2013).

Papp, et al., "Response to retreatment with ustekinumab after withdrawal from therapy in moderate-to- severe psoriasis patients: Results from the PHOENIX 1 and ACCEPT phase 3 clinical trials", (Jun. 2011) (Abstract Only).

Gensler, et al., "An Integrated Safety Data Analysis Across All Phase II and Phase III Clinical Programs for Ustekinumab in Psoriatic Arthritis, Crohns Disease, and Psoriasis", Annals of the Rheumatic Diseases, vol. 76, Suppl 2, p. 950, (2017) (Abstract Only).

Gordon, et al., "Response to retreatment with ustekinumab after withdrawal from therapy in moderate-to- severe psoriasis patients: Results from the PHOENIX 1 and ACCEPT Phase 3 clinical trials", Previously presented (Aug. 2011) (Abstract Only).

Augustin, et al., "Assessment of patient benefit following transition from methotrexate to ustekinumab in psoriasis patients: a sub-analysis of the TRANSIT study", (Oct. 2013) (Abstract Only).

Lebwohl et al. "Ustekinumab reduces itch, bodily pain, and fatigue in patients with moderate to severe psoriasis", Value in Health, vol. 12, No. 3 :A138, (2009) (Abstract Only).

Griffiths, et al., "Response to retreatment with ustekinumab after withdrawal from therapy in patients with moderate to severe psoriasis: results from the PHOENIX 1 and ACCEPT phase 3 clinical trials", British Journal of Dermatology, vol. 165, Suppl 1:43, (2011) (Abstract Only).

Papp, et al., "Long-term safety of ustekinumab: 5 years of follow-up from the psoriasis clinical development program including patients with psoriatic arthritis", (Oct. 2013) (Abstract Only).

Kimball, et al., "Underdiagnosis and undertreatment of cardiovascular risk factors among patients with moderate-to-severe psoriasis: Results from Phase 3 ustekinumab clinical trials", New, (Mar. 2010) (Abstract Only).

(56) References Cited

PUBLICATIONS

Kimball, et al., "Efficacy of ustekinumab is sustained through 3 years of treatment for patients with moderate-to-severe psoriasis maintained on q12 week dosing based on body weight", New, (Jul. 2010) (Abstract Only).

Kavanaugh, et al., "Long Term Improvements in Physical Function Are Associated with Improvements in Dactylitis, Enthesitis, Tender and Swollen Joint Counts, and Psoriasis Skin Involvement: Results from a Phase 3 Study of Ustekinumab in Psoriatic Arthritis Patients", Arthritis & Rheumatology, vol. 66, 11 Suppl :S688, (2014) (Abstract Only).

Reich, et al., "Effect of Ustekinumab on Cardiovascular Events: Results from Pooled Phase 2 and 3 Psoriasis Trials", Previously presented, Canadian Dermatology Association (CDA) (Jun. 2011) (Abstract Only).

Blauvelt, et al., "Extension of ustekinumab maintenance dosing interval in moderate-to-severe psoriasis: results of a phase IIIb, randomized, double-blinded, active-controlled, multicenter study (PSTELLAR)," British Journal of Dermatology, 177: 1552-1561 (2017).

Cao, et al., "Ustekinumab dosing, persistence, and discontinuation patterns in patients with moderate-to-severe psoriasis," Journal of Dermatological Treatment, 26(20): 113-120 (2015).

Carter, et al., "Observational Ustekinumab Dosing Paradigm in Psoriasis: Evidence of Step-Up and Step-Down Events," Abstract No. PSS20, Value in Health, 16: A179 (2013).

Kimball, et al., "Long-term efficacy of ustekinumab in patients with moderate-to-severe psoriasis treated for up to 5 years in the PHOENIX 1 Study," Journal of European Academy of Dermatology and Venereology, 27: 1535-1545 (2013). Abstract Only.

Lebwohl, et al., "Impact of weight on the efficacy and safety of ustekinumab in patients with moderate to severe psoriasis: Rationale for dosing recommendations," Journal of the American Academy of Dermotology, 63: 571-579 (2010).

Papp, et al., "Long-term safety of ustekinumab in patients with moderate-to-severe psoriasis: final results from 5 years of follow-up," British Journal of Dermatology, 168: 844-854 (2013).

Papp, et al., "Safety Surveillance of Ustekinumab and Other Psoriasis Treatment from the Psoriasis Longitudinal Assessment and Registry (PSOLAR)," Journal of Drugs in Dermatology, 14(7): 706-714 (2015).

Papp, et al., "Efficacy and safety of ustekinumab, a human interleukin-12/23 monoclonal antibody, in patients with psoriasis: 52-week results from a randomized, double-blind, placebo-controlled trial (PHOENIX 2)," Lancet, 371: 1675-1684 (2008).

Reich, et al., "An Update on the Long-Term Safety Experience of Ustekinumab: Results from the Psoriasis Clinical Development Program With up to Four Years of Follow-Up," Journal of Drugs in Dermatology, 11(3): 300-312 (2012).

Reich, et al., "Ustekinumab and Marked Clinical Responses in Patients with Moderate to Severe Psoriasis," Psoriasis Forum, 16(1): 3-11 (2010).

Tsai, et al., "The safety of ustekinumab treatment in patients with moderate-to-severe psoriasis and latent tuberculosis infection," British Journal of Dermatology, 167: 1145-1152 (2012).

Yeilding, et al., "Development of the IL-12/23 antagonist ustekinumab in psoriasis: past, present,and future perspectives," Annals of the New York Academy of Sciences, 1222: 30-39 (2011).

Zhu, et al., "Ustekinumab improves health-related quality of life in Chinese patients with moderate to severe plaque psoriasis," Journal of Dermatology, 39 (Suppl. 1): 1-280 (2012).

Zhu, et al., "Exposure-Response Relationship of Ustekinumab in Two Phase 3 Studies in Patients with Moderate-to-Severe Plaque Psoriasis," Abstract Only.

Journal of Clinical Pharmacology, 2010; vol. 50, pp. 257-267.

Langley, et al., "Efficacy and safety of guselkumab in patients with psoriasis who have an inadequate response to ustekinumab: Results of the randomized, double-blind, Phase 3 NAVIGATE trial", British Journal of Dermatology, vol. 178, No. 1, pp. 114-123, (2018).

Reich, et al., "An Update on the Long-Term Safety Experience of Ustekinumab: Results From the Psoriasis Clinical Development Program With up to Four Years of Follow-Up", Journal of drugs in dermatology, vol. 11, No. 3, pp. 300-312, (2012).

Papp, et al., "Efficacy and safety of ustekinumab, a human interleukin-12/23 monoclonal antibody, in patients with psoriasis: 52-week results from a randomised, double-blind, placebo-controlled trial (PHOENIX 2)", Lancet, vol. 371, pp. 1675-1684, (2008).

Papp, et al., "Malignancy Rates in the Ustekinumab Psoriasis Clinical Trial Program: Update With Up to 4 Years of Follow-up and Comparisons to the General United States Population", Previously presented, EADV Fall, (Oct. 2011) (Abstract Only).

Papp, et al., "Malignancies in the Ustekinumab Psoriasis Clinical Development Program: Final Report With Up to 5 Years of Follow-up", BAD, (Jul. 2013) (Abstract Only).

Kimball, et al., "Infection Rates in the Ustekinumab Psoriasis Clinical Trial Program: Update With Up to 4 Years of Follow-Up", Previously presented, EADV Fall, (Oct. 2011) (Abstract Only).

Strober, et al., "Infections in the Ustekinumab Psoriasis Clinical Trial Program: Final Report With Up to 5 Years of Follow-Up", AAD Winter, (Mar. 2013) (Abstract Only).

Strober, et al., "Infections in the Ustekinumab Psoriasis Clinical Trial Program: Final Report With Up to 5 Years of Follow-Up", BAD, (Jul. 2013) (Abstract Only).

Papp, et al., "Malignancy rates in the ustekinumab psoriasis clinical trial program: Update with up to 4 years of follow-up and comparisons to the general United States population", Journal of the American Academy of Dermatology, AAD Winter, vol. 66, 4 Suppl 1 :AB196, (2012) (Abstract Only).

Papp, et al., "Safety Surveillance for Ustekinumab and Other Psoriasis Treatments From the Psoriasis Longitudinal Assessment and Registry (PSOLAR)", Journal of Drugs in Dermatology, vol. 14, No. 7, pp. 706-714, (2015) (Abstract only).

Papp, et al.. "Malignancy rates in ustekinumab psoriasis clinical trials: Up to 4 years of follow-up and comparisons to the general US population". Australasian Journal of Dermatology, ACD, vol. 53, p. 51, (2012) (Abstract Only).

Ho, et al., "Consistency of efficacy and safety outcomes across different ethnic populations: Results from ustekinumab psoriasis clinical trials in Non-Asian and Asian countries", CDA, (Jun. 2013) (Abstract Only).

Tsai, et al., "Consistency of efficacy and safety outcomes across different ethnic populations: Results from ustekinumab psoriasis clinical trials in Non-Asian and Asian countries", ADC, (Jul. 2013) (Abstract Only).

Papp, et al., "Long-term safety of ustekinumab in patients with moderate-to-severe psoriasis: final results from five years of follow-up", British Journal of Dermatology, vol. 168, No. 4, pp. 844-854, (2013).

Kimball, et al., "Infection rates in the ustekinumab psoriasis clinical trial program: Update with up to 4 years of follow-up",, Australasian Journal of Dermatology, ACD, vol. 53, p. 52, (2012) (Abstract Only).

Kimball, et al., "Infection rates in the ustekinumab psoriasis clinical trial program: Update with up to 4 years of follow-up", Journal of the American Academy of Dermatology, AAD Winter, vol. 66, 4 Suppl 1:AB195, (2012) (Abstract Only).

Gordon, et al., "Ustekinumab Safety Update: Cumulative Experience From Longer Term Follow-up of Patients Treated in the Ustekinumab Psoriasis Clinical Development Program", New, BAD, (Jul. 2010) (Abstract Only).

Gordon, et al., "Ustekinumab Safety Update: Cumulative Experience From Longer Term Follow-up of Patients Treated in the Ustekinumab Psoriasis Clinical Development Program", Previously presented, EADV Fall, (Oct. 2010) (Abstract Only).

Gordon, et al., "Ustekinumab Safety Update: Cumulative Experience From Longer Term Follow-up of Patients Treated in the Ustekinumab Psoriasis Clinical Development Program", Previously presented, CPIN ICOP, (Jul. 2010) (Abstract Only).

Gordon, et al., "Ustekinumab Safety Update: Cumulative Experience From Longer Term Follow-up of Patients Treated in the Ustekinumab Psoriasis Clinical Development Program", Previously presented, (Nov. 2010) (Abstract Only).

(56) References Cited

PUBLICATIONS

Gordon, et al., "Ustekinumab Safety Update: Cumulative Experience From Longer Term Follow-up of Patients Treated in the Ustekinumab Psoriasis Clinical Development Program", Previously presented, AAD Summer, (Aug. 2010) (Abstract Only).
Papp, et al., "Malignancies in the Ustekinumab Psoriasis Clinical Development Program: Final Report With Up to 5 Years of Follow-up", Journal of the American Academy of Dermatology, vol. 68, No. 4 :AB206, (2013) (Abstract Only).
Zhu, et al., "Efficacy and Safety of Ustekinumab in Chinese Patients With Moderate to Severe Plaque-type Psoriasis: Results From a Phase 3 Clinical Trial (LOTUS)", Journal of drugs in dermatology, vol. 12, No. 2, pp. 166-174, (2013).
Loesche, et al., "Longitudinal Study of the Psoriasis-Associated Skin Microbiome during Therapy with Ustekinumab in aÂ Randomized Phase 3b Clinical Trial", Journal of Investigative Dermatology 2018, vol. 138, No. 9, pp. 1973-1981, (2018).
Igarashi, et al., "A Randomized, Double-Blind Placebo-Controlled Study of Ustekinumab in Japanese Patients With Moderate to Severe Plaque Psoriasis", CPIN ICOP, (Jul. 2010), (Abstract Only).
Nakagawa, et al., "Ustekinumab Improves Quality of Life in Japanese Patients With Moderate to Severe Plaque Psoriasis", CPIN ICOP, New, (Jul. 2010) (Abstract Only).
Igarashi, et al., "Efficacy and safety of ustekinumab in Japanese patients with moderate-to-severe plaque-type psoriasis: Long-term results from a phase 2/3 clinical trial", Journal of dermatology, vol. 39, No. 3, pp. 242-252, (2012).
Tsai, et al., "The safety of ustekinumab treatment in patients with moderate-to-severe psoriasis and latent tuberculosis infection", British Journal of Dermatology, vol. 167, No. 5, pp. 1145-1152, (2012).
Nakagawa, et al., "Impact of ustekinumab on health-related quality of life in Japanese patients with moderate-to-severe plaque psoriasis: Results from a randomized, double-blind, placebo-controlled phase 2/3 trial", Journal of Dermatology.2012, vol. 39, No. 9, pp. 761-769, (2012).
Papp, et al., "PSOLAR: Global Update of a Multicentre, Open Registry of Psoriasis Patients", EADV Fall, (Sep. 2012) (Abstract Only).
Papp, et al, "PSOLAR: design, utility, and preliminary results of a prospective, international, disease-based registry of patients with psoriasis who are receiving, or are candidates for, conventional systemic treatments or biologic agents", Journal of Drugs in Dermatology, vol. 11, No. 10, pp. 1210-1217, (2012).
Benson, et al., "Discovery and mechanism of ustekinumab: a human monoclonal antibody targeting interleukin-12 and interleukin-23 for treatment of immune-mediated disorders [Review]", mAbs, vol. 3, No. 6, pp. 535-545, (2011).
Papp, et al., "Long-term safety of ustekinumab: 5 years of follow-up from the psoriasis clinical development program including patients with psoriatic arthritis", EADV, (Oct. 2013) (Abstract Only).
Gordon, et al., "The ustekinumab safety experience in patients with moderate-to-severe psoriasis: Results from pooled analyses of Phase 2 and Phase 3 clinical trial data", Maui Derm, (Jan. 23-27, 2010) (Abstract Only).
Healy, et al., "Comparison of hospitalization and serious infections rates among patients with moderate-to-severe psoriasis treated with ustekinumab: Comparisons to a large healthcare claims database", AAD Summer, (Jul. 29-Aug. 2, 2009) (Abstract Only).
Papp, et al., "Safety of ustekinumab from the placebo-controlled periods of psoriatic arthritis and psoriasis clinical developmental programs", (Oct. 2013) (Abstract Only).
Gordon, et al., "Effect of Ustekinumab on Cardiovascular Events: Results from Pooled Phase 2 and 3 Psoriasis Trials", New, Feb. 2011, (Abstract Only).
Kimball, et al., "Long Term Efficacy and Safety of Ustekinumab in Patients with Moderate to Severe Psoriasis Through 5 Years of Follow-up: Results from the PHOENIX 1 Long-Term Extension", (Jun. 2012) (Abstract Only).
Kimball, et al., "Efficacy of ustekinumab is sustained through 3 years of treatment for patients with moderate-to-severe psoriasis maintained on q12 week dosing based on body weight", Previously presented, American Academy of Dermatology (Aug. 2010) (Abstract Only).
Gordon, et al., "Sustained efficacy of ustekinumab for the treatment of moderate to severe psoriasis in initial responders continuing with maintenance therapy through year 3", New, (Jul. 2010) (Abstract Only).
Lebwohl, et al., "Two-step dosing of subcutaneous ustekinumab by body weight provides similar efficacy in heavier and lighter weight patients with moderate-to-severe psoriasis [previously presented]", EADV Fall, (Abstract Only), 2009.
Gordon, et al., "The ustekinumab safety experience in patients with moderate-to-severe psoriasis: Results from pooled analyses of Phase 2 and Phase 3 clinical trial data", Winter Clinical Derm, Previously presented, Winter Clinical Derm, (Jan. 2010) (Abstract Only).
Gordon, et al., "The ustekinumab safety experience in patients with moderate-to-severe psoriasis: Results from pooled analyses of Phase 2 and Phase 3 clinical trial data", OADC, Previously presented, OADC, (Jan. 2010) (Abstract Only).
Reich, et al., "Ustekinumab improves quality of life outcomes in psoriasis patients transitioned from methotrexate regardless of transition strategy: Week 16 results from the TRANSIT study", Experimental Dermatology, ADF, vol. 21, No. 3 :e13 (2012) (Abstract Only).
Gordon, et al., "The ustekinumab safety experience in patients with moderate-to-severe psoriasis: Results from pooled analyses of Phase 2 and Phase 3 clinical trial data", Previously presented, AAD Winter, (Mar. 2010) (Abstract Only).
Papp, et al., "Long-term safety of ustekinumab in patients with moderate to severe psoriasis through up to 5 years of continuous follow-up", EADV Fall, (Sep. 2012) (Abstract Only).
Reich, et al., "Long-term improvement in patient-reported outcomes after transition from methotrexate to ustekinumab in moderate to severe psoriasis: TRANSIT Week 52 results", EADV Fall (Sep. 2012) (Abstract Only).
Mcinnes, et al., "Safety of ustekinumab from the placebo-controlled periods of psoriatic arthritis and psoriasis clinical developmental programs", ACR, (Oct. 2013) (Abstract Only).
Feldman, et al.,"Cost per responder of ustekinumab versus etanercept in patients with moderate-to-severe plaque psoriasis: Analysis from the ACCEPT Trial" , EADV Fall, (Oct. 2010) (Abstract Only).
Langley, et al., "Long Term Efficacy and Safety of Ustekinumab in Patients with Moderate to Severe Psoriasis Through 5 Years of Follow-up: Results from the PHOENIX 2 Long-Term Extension", EADV Fall, (Sep. 2012) (Abstract Only).
Papp, et al., "Long Term Efficacy and Safety of Ustekinumab in Patients with Moderate to Severe Psoriasis Through 5 Years of Follow-up: Results from the PHOENIX 1 Long-Term Extension", CDA, (Jun.-Jul. 2012), (Abstract Only).
Reich, et al., "Update on the cardiovascular safety of ustekinumab in pooled phase 2 and 3 psoriasis clinical trials with up to 4 years of follow-up", EADV Fall, Previously presented, (Oct. 2011) (Abstract Only).
Gordon, et al., "Sustained efficacy of ustekinumab for the treatment of moderate to severe psoriasis in initial responders continuing with maintenance therapy through year 3", AAD Winter, Previously presented, (Feb. 2011) (Abstract Only).
Carter, et al., "Discontinuation, Restart, and Switching Patterns Among Psoriasis Patients Treated With Adalimumab, Etanercept, or Ustekinumab: A United States Claims Database Analysis", Medical Decision Making, SMDM, vol. 35, No. 1: E32-33, (2015) (Abstract Only).
Matheson, et al., "Consistency of ustekinumab response across different body regions and PASI components for the treatment of moderate-to-severe psoriasis: Results from the PHOENIX 1 and PHOENIX 2 trials", AAD Summer, (Jul.-Aug. 2009) (Abstract Only).
Griffiths, et al., "Ustekinumab treatment in patients with moderate-to-severe psoriasis who are non-responders to etanercept: Results from a Phase 3 clinical trial", AAD Winter, New, (Mar. 2010) (Abstract Only).
Lebwohl, et al., "Two doses of subcutaneous ustekinumab based on body weight provides similar efficacy in heavier and lighter weight

(56) References Cited

PUBLICATIONS patients with moderate-to-severe psoriasis", Winter Clinical Derm, Previously presented, (Jan. 2010) (Abstract Only).

Griffiths, et al., "Ustekinumab Treatment in Patients with Moderate-to-Severe Psoriasis who are Nonresponders to Etanercept: Results from a Phase 3 Clinical Trial", AAD Winter, (Abstract Only), 2010.

Paul, et al., "Ustekinumab is well-tolerated & effective in patients with psoriasis inadequately responsive to methotrexate: Week 12 results from the TRANSIT study", Experimental Dermatology, ADF, vol. 21, No. 3 :e13, (2012) (Abstract Only).

Sobell, et al., "Improved clinical response following a third dose of ustekinumab in psoriasis patients not achieving PASI75 at week 16: Results from the PHOENIX 1 and PHOENIX 2 trials", CPIN ICOP, New, (Jul. 2010) (Abstract Only).

Reich, et al., "Improved clinical response following a third dose of ustekinumab in psoriasis patients not achieving PASI75 at week 16: Results from the PHOENIX 1 and PHOENIX 2 trials", EADV Fall, Previously presented (Oct. 2010) (Abstract Only).

Healy, et al., "Comparison of hospitalization and serious infections rates among patients with moderate-to-severe psoriasis treated with ustekinumab: Comparisons to a large healthcare claims database [previously presented]", BAD, (Jul. 2009) (Abstract Only).

Papp, et al., "Malignancies in Ustekinumab-Treated Moderate-to-Severe Psoriasis Patients: Observations With Up to 3 Years of Follow-Up and Comparisons to the General United States Population", EADV Fall, Previously Presented, (Oct. 2010) (Abstract Only).

Feldman, et al., "Cost per responder of ustekinumab versus etanercept in patients with moderate-to-severe plaque psoriasis: Analysis from the ACCEPT Trial", ISPOR Annual, (May 2010) (Abstract Only).

Feldman, et al., "Cost per responder of ustekinumab versus etanercept in patients with moderate-to-severe plaque psoriasis: Analysis from the ACCEPT Trial", AAD Summer, (Aug. 2010) (Abstract Only).

Kimball, et al., "Long Term Efficacy and Safety of Ustekinumab in Patients with Moderate to Severe Psoriasis Through 5 Years of Follow-up: Results from the PHOENIX 1 Long-Term Extension", British Journal of Dermatology, BAD, vol. 167, Suppl 1, pp. 63-64, (2012) (Abstract Only).

Ghislain, et al., "Maintenance of long-term efficacy of ustekinumab through year 3 for patients with moderate-to-severe psoriasis", EADV Fall, (Oct. 2010)(Abstract Only).

Papp, et al., "Malignancies in Ustekinumab-Treated Psoriasis Patients: Observations With Up to 3 Yrs of Follow-Up and Comparisons to the General US Population", SID, New, (May 2010) (Abstract Only).

Gordon, et al., "Infection Rates in Ustekinumab-Treated Psoriasis Patients: Observations With Up to 3 Years of Follow-Up and Comparisons to a Large Health Care Claims Database", AAD Summer, Previously presented, (Aug. 2010) (Abstract Only).

Lebwohl, et al., "Two doses of subcutaneous ustekinumab based on body weight provides similar efficacy in heavier and lighter weight patients with moderate-to-severe psoriasis", ODAC, Previously presented, (Jan. 2010) (Abstract Only).

Lebwohl, et al., "Two doses of subcutaneous ustekinumab based on body weight provides similar efficacy in heavier and lighter weight patients with moderate-to-severe psoriasis", Maui Derm, Previously presented, (Jan. 2010) (Abstract Only).

Lebwohl, et al., "Two-step dosing of subcutaneous ustekinumab by body weight provides similar efficacy in heavier and lighter weight patients with moderate-to-severe psoriasis", AAD Summer, (Jul.-Aug. 2009) (Abstract Only).

Leonardi, et al., "Maintenance of long-term efficacy of ustekinumab through year 3 for patients with moderate-to-severe psoriasis", Previously presented, (Nov. 2010) (Abstract Only).

Reich, et al., "Update on the cardiovascular safety of ustekinumab in pooled phase II and III psoriasis clinical trials with up to 4 years of follow-up", Journal of the American Academy of Dermatology, AAD Winter, 2vol. 66, 4 Suppl 1: AB206, (2012) (Abstract Only).

Gordon, et al., "Effect of ustekinumab on cardiovascular events: Results from pooled phase II and III psoriasis trials", Journal of the American Academy of Dermatology, AAD Winter, vol. 64, 2 Suppl 1: AB146, (2011) (Abstract Only).

Papp, et al., "Malignancies in Ustekinumab-Treated Moderate-to-Severe Psoriasis Patients: Observations With Up to 3 Years of Follow-Up and Comparisons to the General United States Population", AAD Summer, Previously presented, (Aug. 2010) (Abstract Only).

Davis, et al., "Systemic Exposure and Efficacy/Safety of Ustekinumab in Patients with Moderate to Severe Psoriasis", EADV Fall, New, (Oct. 2010) (Abstract Only).

Brodmerkel, et al., "Long-term treatment with ustekinumab does not compromise the immune response to T-cell dependent or T-cell independent vaccines in patients with moderate-to-severe psoriasis: A comparison of ustekinumab-treated versus untreated psoriasis patients", SID, (May 2012) (Abstract Only).

Carter, et al., "PSS20—Observational Ustekinumab Dosing Paradigm In Psoriasis: Evidence Of Step-Up And Step-Down Events", Value in Health, ISPOR Annual, vol. 16, No. 3:A179, (2013)(Abstract Only).

Langley, et al., "Ustekinumab is Associated with Significant Improvements in Overall Health-Related Quality of Life in Moderate-to-Severe Psoriasis Patients", AAD Summer, (Jul.-Aug. 2008) (Abstract Only).

Zhu, et al. "Exposure-Response Relationship of Ustekinumab in Two Phase 3 Studies in Patients with Moderate-to-Severe Plaque Psoriasis", AAPS, (Nov. 2009) (Abstract Only).

Papp, et al., "Long term efficacy and safety of ustekinumab in patients with moderate to severe psoriasis through 5 years of follow-up: results from the PHOENIX 1 long-term extension", The Journal of Dermatology, JDA, vol. 39, Suppl 1, pp. 239-240, (2012) (Abstract Only).

Papp, et al., "Long-term safety of ustekinumab in patients with moderate to severe psoriasis through up to 5 years of continuous follow-up", Journal of the American Academy of Dermatology, AAD Winter, vol. 68, 4 Suppl.: AB205, (2013) (Abstract Only).

Brodmerkel, et al., "Long-term treatment with ustekinumab does not compromise the immune response to T-cell dependent or T-cell independent vaccines in patients with moderate to severe psoriasis: A comparison of ustekinumab-treated versus untreated psoriasis patients", EADV Fall, (Sep. 2012) (Abstract Only).

Reich, et al., "Ustekinumab And Marked Clinical Responses In Patients With Moderate-to-Severe Psoriasis", AAD Summer (Jul.-Aug. 2008) (Abstract Only).

Langley, et al., "Ustekinumab significantly improves symptoms of anxiety, depression, and skin-related quality of life in patients with moderate-to-severe psoriasis: Results from a randomized, double-blind, placebo-controlled phase III trial", Journal of the American Academy of Dermatology, vol. 63, No. 3, pp. 457-465, (2010).

Zhu, et al., "Ustekinumab Improves Health-Related Quality of Life in Chinese Patients with Moderate to Severe Plaque Psoriasis", Journal of Dermatology, vol. 39, Suppl. 1:239 (2012) (Abstract Only).

Hu, et al., "Informative dropout modeling of longitudinal ordered categorical data and model validation: application to exposure-response modeling of physician's global assessment score for ustekinumab in patients with psoriasis", Journal of Pharmacokinetics and Pharmacodynamics, vol. 38, No. 2, pp. 237-260, (2011).

Lebwohl, et al., "Ustekinumab improves health-related quality of life in patients with moderate-to-severe psoriasis: results from the Phoenix 1 trial", British Journal of Dermatology, vol. 162, No. 1, pp. 137-146, (2010).

Opel, et al., "Two Cases of Hepatitis B in Patients With Moderate to Severe Psoriasis Treated With Ustekinumab", Journal of drugs in dermatology, vol. 11, No. 12, pp. 1498-1501, (2012).

Hu, et al., "Bounded outcome score modeling: application to treating psoriasis with ustekinumab", Journal of Pharmacokinetics and Pharmacodynamics, vol. 38, No. 4, pp. 497-517, (2011).

Zhang, et al., "Characterizing Patients with Psoriasis on Injectable Biologics Adalinumab, Etanercept, and Ustekinumab: A Chart Review Study", Journal of Dermatological Treatment, (2015).

Zhu, et al., "Immunogenicity Assessment of Ustekinumab in Phase 3 Studies in Patients with Moderate to Severe Plaque Psoriasis", Previously presented, EADV Fall, (Oct. 2010) (Abstract Only).

(56) References Cited

PUBLICATIONS

Zhu, et al., "Immunogenicity Assessment of Ustekinumab in Phase 3 Studies in Patients with Moderate to Severe Plaque Psoriasis", New, AAPS-NBC, (May 2010) (Abstract Only).
Reddy, et al., "Positive treatment effects of ustekinumab in psoriasis: Analysis of lesional and systemic parameters", Journal of Dermatology, vol. 47, pp. 413-425, (2010).
Reich, et al., "Ustekinumab Reduces Work Limitations, Increases Work Productivity and Decreases Workdays Missed Due to Psoriasis in Patients With Moderate to Severe Psoriasis", Value in Health, ISPOR Health, vol. 11, No. 6: A626 (2008) (Abstract Only).
Blauvelt, et al., "Extension of ustekinumab maintenance dosing interval in moderate-to-severe psoriasis: results of a Phase 3b, randomized, double-blinded, active-controlled, multicenter study (PSTELLAR)", British Journal of Dermatology, vol. 177, No. 6, pp. 1552-1561, (2017).
Li, et al., "HLA-C*06:02 Allele and Response to IL-12/23 Inhibition: Results from the Ustekinumab Phase 3 Psoriasis Program", Journal of Investigative Dermatology, vol. 136, No. 12, pp. 2364-2371, (2016).
Avgerinou, et al., "Budget impact analysis of ustekinumab in the management of moderate to severe psoriasis in Greece", BMC Dermatology, vol. 12, No. 1, p. 10, (2012).
Lebwohl, et al., "Long-term safety experience of ustekinumab in patients with moderate-to-severe psoriasis (Part I of II): Results from analyses of general safety parameters from pooled Phase 2 and 3 clinical trials", Journal of the American Academy of Dermatology, vol. 66, No. 5, pp. 731-741, (2012).
Lebwohl, et al., "Impact of weight on the efficacy and safety of ustekinumab in patients with moderate to severe psoriasis: Rationale for dosing recommendations", Journal of the American Academy of Dermatology, vol. 63, No. 4, pp. 571-579, (2010).
Reich, et al., "Ustekinumab and Marked Clinical Responses in Patients with Moderate to Severe Psoriasis", Psoriasis Forum, vol. 16, No. 1, pp. 3-11, (2010).
Zhu, et al., "Population Pharmacokinetic Modeling of Ustekinumab, a Human Monoclonal Antibody Targeting IL-12/23p40, in Patients With Moderate to Severe Plaque Psoriasis", Journal of Clinical Pharmacology, vol. 49, pp. 162-175, (2009).
Gordon, et al., "Long-term safety experience of ustekinumab in patients with moderate to severe psoriasis (Part II of II): Results from analyses of infections and malignancy from pooled phase II and III clinical trials", Journal of the American Academy of Dermatology, vol. 66, No. 5, 742-751, (2012).
Martin, et al., "Cost per responder analysis of ustekinumab and etanercept for moderate to severe plaque psoriasis", Journal of Dermatological Treatment, vol. 22, No. 3, pp. 138-143, (2011).
Papp, et al., "Long-term safety of ustekinumab in patients with moderate-to-severe psoriasis: final results from 5 years of follow-up", British Journal of Dermatology, vol. 168, No. 4, pp. 844-854, (2013).
Reich, et al., "Ustekinumab decreases work limitations, improves work productivity, and reduces work days missed in patients with moderate-to-severe psoriasis: Results from PHOENIX 2", Journal of Dermatological Treatment, vol. 22, No. 6, pp. 337-347, (2011).
Zhou, et al., "Population-Based Exposure-Efficacy Modeling of Ustekinumab in Patients With Moderate to Severe Plaque Psoriasis", Journal of Clinical Pharmacology, vol. 50, pp. 257-267, (2010).
Yeilding, et al., "Development of the IL-12/23 antagonist ustekinumab in psoriasis: past, present, and future perspectives", Annals of the New York Academy of Sciences, vol. 1222, pp. 30-39 (2011).
Guenther, et al., "Impact of ustekinumab on health-related quality of life and sexual difficulties associated with psoriasis: results from two phase III clinical trials", Journal of the European Academy of Dermatology and Venereology, vol. 25, pp. 851-857, (2011).
Tsai, et al., "Efficacy and safety of ustekinumab for the treatment of moderate-to-severe psoriasis: A phase III, randomized, placebo-controlled trial in Taiwanese and Korean patients (PEARL)", Journal of Dermatological Science, vol. 63, No. 3. pp. 154-163, (2011).
Kimball, et al., "Long-term efficacy of ustekinumab in patients with moderate-to-severe psoriasis treated for up to 5 years in the PHOENIX 1 study", Journal of the European Academy of Dermatology and Venereology, vol. 27, No. 12, pp. 1535-1545, (2013).
Reich, et al., "Cardiovascular safety of ustekinumab in patients with moderate-to-severe psoriasis: Results of integrated analyses of data from phase II and III clinical studies", British Journal of Dermatology, vol. 164, pp. 862-872, (2011).
Landells, et al., "Safety and efficacy of ustekinumab in adolescent patients with moderate-to-severe plaque psoriasis: Results through 1 year of the Phase 3 CADMUS trial", EADV Fall, (Oct. 2015) (Abstract Only).
Rich, et al., "Ustekinumab improves nail disease in patients with moderate-to-severe psoriasis: results from PHOENIX 1", British Journal of Dermatology, vol. 170, No. 2, pp. 398-407, (2014).
Cao, et al., "Ustekinumab dosing, persistence, and discontinuation patterns in patients with moderate-to-severe psoriasis", Journal of Dermatological Treatment, vol. 26, No. 2, pp. 113-120, (2015).
Langley, et al., "Long-term efficacy and safety of ustekinumab, with and without dosing adjustment, in patients with moderate-to-severe psoriasis: Results from the PHOENIX 2 study through 5 years of follow-up", British Journal of Dermatology, vol. 172, No. 5, pp. 1371-1383, (2015).
Leonardi, et al., "Efficacy and safety of ustekinumab, a human interleukin-12/23 monoclonal antibody, in patients with psoriasis: 76-week results from a randomised, double-blind, placebo-controlled trial (PHOENIX 1", Lancet, vol. 371, pp. 1665-1674, (2008).
Landells, et al., "Ustekinumab in adolescent patients age 12 to 17 years with moderate-to-severe plaque psoriasis: Results of the randomized phase 3 CADMUS study", Journal of the American Academy of Dermatology, vol. 73, No. 4, pp. 594-603, (2015).
Tsai, et al., "Consistency of responses across different ethnic populations with moderate-to-severe psoriasis: Results from the ustekinumab psoriasis clinical development program", Previously presented, AAD Summer, (Aug. 2011) (Abstract Only).
Papp, et al., "Experience with ustekinumab in patients with psoriasis enrolled in a large, multicenter, prospective, disease-based registry (Psoriasis Longitudinal Assessment and Registry [PSOLAR]) [Please Note: This publication has been voluntarily withdrawn by the authors in order to present more updated data in a subsequent manuscript.", Journal of the American Academy of Dermatology, (2015).
Reich et al., "Effect of Ustekinumab on Cardiovascular Events: Results from Pooled Phase 2 & 3 PsoriasisTrials," Journal of the American Academy of Dermatology. vol. 64, No. 2, Suppl. 1:AB146, 2 pages (2011) (Abstract Only).
Papp et al., "Response to retreatment with ustekinumab after withdrawal from therapy in moderate-to-severe psoriasis patients: Results form the PHOENIX 1 and ACCEPT phase 3 clinical trials," CDA, (Jun. 22-26, 2011) (Abstract Only).
Bissonnette, et al., "Reduction in C-Reactive Protein Concentrations in Patients With Moderate to Severe Psoriasis: Results From the PHOENIX 1 and 2 Clinical Trials", (Oct. 2010), (Abstract Only).
Suarez-Farinas et al., "Expanding the Psoriasis Disease Profile: Interrogation of the Skin and Serum of Patients with Moderate-to-Severe Psoriasis", Journal of Investigative Dermatology. vol. 132, No. 11, pp. 2552-2564, (2012).
Vender, et al., "Comparison of guselkumab with placebo and adalimumab on health-related quality of life in a phase 2b clinical trial X-PLORE", Journal of the American Academy of Dermatology, vol. 74, No. 5, AB241, (2016) (Abstract Only).
Deodhar, et al., "Efficacy and safety of guselkumab in patients with active psoriatic arthritis: a randomised, double-blind, placebo-controlled, phase 2 study", Lancet.vol. 391, No. 10136, pp. 2213-2224, (2018).
Strober, et al., "Features of a Population of Psoriasis Patients Who Are Candidates for Systemic Therapy Including Biologics: Results From the PSOLAR Registry", (Oct. 2011) (Abstract only).
Kimball, et al., "Pregnancy outcomes in women with moderate to severe psoriasis: The PSOLAR experience", Journal of Investigative Dermatology, 135:S16 (2015) (Abstract only).

(56) References Cited

PUBLICATIONS

Papp, et al., "PSOLAR: International Update of a Multicenter, Open Registry of Psoriasis Patients", EADV Fall, (Oct. 2011) (Abstract Only).
Augustin, et al., "Psoriasis Longitudinal Assessment and Registry (PSOLAR): Global Update of a Multicentre, Open Registry of Psoriasis Patients", (Oct. 2013) (Abstract Only).
Gottlieb, et al., "A phase 1, double-blind, placebo-controlled study evaluating single subcutaneous administrations of a human interleukin-12/23 monoclonal antibody in subjects with plaque psoriasis", Current Medical Research and opinion, vol. 23, No. 5, pp. 1081-1092, (2007).
Toichi, et al., "An Anti-IL-12p40 antibody Down-Regulates type 1 Cytokines, Chemokines, and IL-12/IL-23 in Psoriasis", Journal of Immunology vol. 177, pp. 4917-4926, (2006).
Kauffman, et al., "A Phase I Study Evaluating the Safety, Pharmacokinetics, and Clinical Response of a Human IL-12 p40 Antibody in Subjects with Plaque Psoriasis", Journal of Investigative Dermatology, vol. 123, pp. 1037-1044, (2004).
Bissonnette, et al., "Major Adverse Cardiovascular Events Among Initiators of Biologic Therapies in the Psoriasis Longitudinal Assessment and Registry (PSOLAR) Study", (Oct. 2013) (Abstract Only).
Loftus, et al., "[Mo1884] Prevalence of Inflammatory Bowel Disease Among Patients With Psoriasis and Incidence of Serious Infections in This Subset: Results From the PSOLAR Registry", Gastroenterology vol. 150, No. 4 :S805, (2016) (Abstract Only).
Fiorentino, et al., "Malignancies in the psoriasis longitudinal assessment and registry (PSOLAR) study: Current status of observations", Annals of the Rheumatic Diseases,vol. 74, Suppl 2, p. 862, (2015) (Abstract Only).
Menter, et al., "Persistence of biologic therapy in psoriatic disease: Results from the Psoriasis Longitudinal Assessment and Registry (PSOLAR)", Journal of the American Academy of Dermatology, vol. 72, No. 5 :AB242, (2015) (Abstract Only).
Obando, et al., "Cost-Effectiveness Analysis of Ustekinumab Compared With Etanercept for the Treatment of Moderate to Severe Psoriasis in Costa Rica", ISPOR Europe, (Nov. 8-12, 2014) (Abstract Only).
Bolge, et al., "Patient experience with intravenous biologic therapies for ankylosing spondylitis, Crohn's disease, psoriatic arthritis, psoriasis, rheumatoid arthritis, and ulcerative colitis", Patient Preference and Adherence, vol. 11, pp. 661-669, (2017).
Gottlieb, et al., "Major Adverse Cardiovascular Events in the Psoriasis Longitudinal Assessment and Registry (PSOLAR) Study: Current Status of Observations", EADV, (Oct. 2013) (Abstract Only).
Loftus, et al., "[P626] Prevalence of inflammatory bowel disease amongst patients with psoriasis and incidence of serious infections in this subset: results from the PSOLAR Registry", Journal of Crohns and Colitis, vol. 10, No. 1 : S418-S418, (2016) (Abstract Only).
Kalb, et al., "Serious Infection Events in the Psoriasis Longitudinal Assessment and Registry Study: Cumulative Experience", Arthritis & Rheumatology, vol. 66, 11 Suppl :S232, (2014) (Abstract Only).
Leonardi, et al., "Serious Infection Events in the Psoriasis Longitudinal Assessment and Registry (PSOLAR) Study: Current Status of Observations", Journal of the American Academy of Dermatology, vol. 68, No. 4 :AB213, (2013) (Abstract Only).
Strober, et al, "Psoriasis Longitudinal Assessment and Registry: Global Update upon Full Enrollment", Arthritis & Rheumatology, vol. 66, 11 Suppl :S690, (2014) (Abstract Only).
Alcusky, et al., "Dermatologist and Patient Preferences in Choosing Treatments for Moderate to Severe Psoriasis", Dermatology and Therapy, (2017).
Kalb, et al., "Serious Infection Events in the Psoriasis Longitudinal Assessment and Registry (PSOLAR) Study: Current Status of Observations", (Oct. 2013) (Abstract Only).
Reich, et al., "Efficacy of guselkumab in patients with moderate-to-severe plaque psoriasis with involvement of the scalp, nails, hands, and feet: Results from the phase 3 VOYAGE 2 study", Journal of the American Academy of Dermatology, vol. 76, No. 6 :AB120, (2017) (Abstract Only).
Lebwohl, et al., Malignancy Events in the Psoriasis Longitudinal Assessment and Registry (PSOLAR) Study: Current Status of Observations, (Oct. 2013) (Abstract Only).
Gottlieb, et al., "Efficacy, safety and health-related quality of life of infliximab therapy in plaque psoriasis patients previously treated with etanercept: Analysis of PSUNRISE", (Jul. 2010) (Abstract Only).
Krueger, et al., "The molecular profile of psoriatic skin in responders to ustekinumab or etanercept following twelve weeks of treatment: Results from the ACCEPT Trial", (Mar. 2010) (Abstract Only).
Fiorentino, et al., "Malignancies in the Psoriasis Longitudinal Assessment and Registry Study: Cumulative Experience", Arthritis & Rheumatology, vol. 66, 11 Suppl :S690, (2014) (Abstract Only).
Strober, et al., "PSOLAR: Update of a multicenter registry of patients with psoriasis who are candidates for systemic therapy including biologics", Journal of the American Academy of Dermatology, vol. 66, 4 Suppl 1: AB89, (2012) (Abstract Only).
Strober, et al., "PSOLAR: Update of a Multicenter Registry of Patients with Psoriasis Who Are Candidates for Systemic Therapy Including Biologics", (Feb. 2011) (Abstract Only).
Menter, et al. "Persistence of biologic therapy in psoriatic disease: Results from the psoriasis longitudinal assessment and registry (PSOLAR)", Annals of the Rheumatic Diseases, vol. 74, Suppl 2 :863, (2015) (Abstract Only).
Gottlieb, et al., "Ustekinumab, a Human Interleukin-12/23 Monoclonal Antibody, Significantly Improves Overall Skin Response and Health Related Quality Of Life in Patients with Psoriatic Arthritis [previously presented]", Jul. 30-Aug. 3, 2008, (Abstract Only).
Bissonnette, et al., "Major Adverse Cardiovascular Events in the Psoriasis Longitudinal Assessment and Registry (PSOLAR) Study: Current Status of Observations", (Jun. 2013) (Abstract Only).
Kavanaugh, et al., "Efficacy and safety of ustekinumab in patients with active psoriatic arthritis: 2-year results from a phase 3, multicenter, double-blind, placebo-controlled study", Annals of the Rheumatic Diseases, vol. 73, Suppl 2 :737-738, (2014) (Abstract Only).
Kalb, et al., "Serious infection events in the psoriasis longitudinal assessment and registry study: Current status of observations", Annals of the Rheumatic Diseases, vol. 74, Suppl 2 :862-863, (2015) (Abstract Only).
Naldi, et al., "Major Adverse Cardiovascular Events in the Psoriasis Longitudinal Assessment and Registry (PSOLAR) Study: Current Status of Observations", (Sep. 2012) (Abstract Only).
Langley, et al., "Malignancy events in the psoriasis longitudinal assessment and registry (PSOLAR) study: Current status of observations", (Jun. 2013) (Abstract Only).
Luo, et al., "Structural basis for the dual recognition of IL-12 and IL-23 by ustekinumab", Journal of Molecular Biology, vol. 402, No. 5, pp. 797-812, (2010).
Shear, et al., "Observations from our evaluation of bodyweight changes after initiation of a biologic therapy in the Psoriasis Longitudinal Assessment and Registry (PSOLAR) [Letter]", Journal of the European Academy of Dermatology and Venereology, vol. 31, No. 12: e544-e547 (2017) (Abstract Only).
Langley, et al., "Malignancy events in the psoriasis longitudinal assessment and registry (PSOLAR) study: Current status of observations", Journal of the American Academy of Dermatology, 68, 4 Suppl 1 :AB206 (2013) (Abstract Only).
Langley, et al., "Malignancy events in the psoriasis longitudinal assessment and registry (PSOLAR) study: Current status of observations", (Sep. 2012) (Abstract Only).
Leonardi, et al., Serious Infection Events in the Psoriasis Longitudinal Assessment and Registry (PSOLAR) Study: Current Status of Observations, EADV Fall, (Sep. 2012) (Abstract Only).
Gordon, et al., "A Phase 2 Trial of Guselkumab versus Adalimumab for Plaque Psoriasis", New England Journal of Medicine, vol. 373, No. 2, pp. 136-144, (2015).
Langley, et al., "Malignancy events in the psoriasis longitudinal assessment and registry study: current status of observations",

(56) References Cited

PUBLICATIONS

Journal of the European Academy of Dermatology and Venereology, vol. 27, Suppl 4:23-24, (2013) (Abstract Only).

Fiorentino, et al., "Malignancy events in the Psoriasis Longitudinal Assessment and Registry (PSOLAR) study: Current status of observations", Journal of the American Academy of Dermatology, vol. 70, 5 Suppl 1: AB175 (2014) (Abstract Only).

Gottlieb, et al., "Major Adverse Cardiovascular Events in the Psoriasis Longitudinal Assessment and Registry (PSOLAR) Study: Current Status of Observations", Journal of the American Academy of Dermatology, vol. 68, 4 Suppl 1 :AB205, (2013) (Abstract Only).

Gordon, et al., "A Phase 2 Trial of Guselkumab versus Adalimumab for Plaque Psoriasis," New England Journal of Medicine, 373 (2): 136-144 (2015).

Anonymous, "NCT02207231: A Study of Guselkumab in the Treatment of Participants with Moderate to Severe Plaque-Type Psoriasis," https://clinicaltrials.gov/archive/ (Jul. 4, 2017).

Anonymous, "NCT02207244: A Study of Guselkumab in the Treatment of Participants with Moderate to Severe Plaque-type Psoriasis with Randomized Withdrawal and Retreatment," https://clinicaltrials.gov/archive/ (Jul. 4, 2017).

NCBI Accession No. 3HMW_L, Chain L, Ustekinumab Fab Light Chain, Release Date Jul. 22, 2015.

NCBI Accession No. 3HMW_H, Chain H, Ustekinumab Fab Heavy Chain, Release Date Jul. 22, 2015.

\* cited by examiner

Group 1 = ustekinumab q12w maintenance regimen; Group 2 = ustekinumab subject-tailored interval maintenance regimen

[GEFPASI01.RTF] [CNTO1275\PSO3009\DBR_WEEK_124\RE_WEEK_124_CSR\PROD\GEFPASI01.SAS] 01OCT2015, 14:12

SEQUENCE LISTING

<160> NUMBER OF SEQ ID NOS: 9

<210> SEQ ID NO 1
<211> LENGTH: 5
<212> TYPE: PRT
<213> ORGANISM: Homo sapiens

<400> SEQUENCE: 1

Thr Tyr Trp Leu Gly
1               5

<210> SEQ ID NO 2
<211> LENGTH: 17
<212> TYPE: PRT
<213> ORGANISM: Homo sapiens

<400> SEQUENCE: 2

Ile Met Ser Pro Val Asp Ser Asp Ile Arg Tyr Ser Pro Ser Phe Gln
1               5                   10                  15

Gly

```
<210> SEQ ID NO 3
<211> LENGTH: 10
<212> TYPE: PRT
<213> ORGANISM: Homo sapiens

<400> SEQUENCE: 3

Arg Arg Pro Gly Gln Gly Tyr Phe Asp Phe
1               5                   10

<210> SEQ ID NO 4
<211> LENGTH: 11
<212> TYPE: PRT
<213> ORGANISM: Homo sapiens

<400> SEQUENCE: 4

Arg Ala Ser Gln Gly Ile Ser Ser Trp Leu Ala
1               5                   10

<210> SEQ ID NO 5
<211> LENGTH: 7
<212> TYPE: PRT
<213> ORGANISM: Homo sapiens

<400> SEQUENCE: 5

Ala Ala Ser Ser Leu Gln Ser
1               5

<210> SEQ ID NO 6
<211> LENGTH: 9
<212> TYPE: PRT
<213> ORGANISM: Homo sapiens

<400> SEQUENCE: 6

Gln Gln Tyr Asn Ile Tyr Pro Tyr Thr
1               5

<210> SEQ ID NO 7
<211> LENGTH: 119
<212> TYPE: PRT
<213> ORGANISM: Homo sapiens

<400> SEQUENCE: 7

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
                20                  25                  30

Trp Leu Gly Trp Val Arg Gln Met Pro Gly Lys Gly Leu Asp Trp Ile
            35                  40                  45

Gly Ile Met Ser Pro Val Asp Ser Asp Ile Arg Tyr Ser Pro Ser Phe
        50                  55                  60

Gln Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                85                  90                  95

Ala Arg Arg Arg Pro Gly Gln Gly Tyr Phe Asp Phe Trp Gly Gln Gly
                100                 105                 110

Thr Leu Val Thr Val Ser Ser
            115

<210> SEQ ID NO 8
<211> LENGTH: 108
<212> TYPE: PRT
```

<213> ORGANISM: Homo sapiens

<400> SEQUENCE: 8

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Tyr
                85                  90                  95

Thr Phe Gly Gln Gly Thr Lys Leu Glu Ile Lys Arg
            100                 105
```

<210> SEQ ID NO 9
<211> LENGTH: 503
<212> TYPE: PRT
<213> ORGANISM: Homo sapiens

<400> SEQUENCE: 9

```
Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser Ile Trp Glu Leu Lys Lys Asp Val Tyr Val Val
        195                 200                 205

Glu Leu Asp Trp Tyr Pro Asp Ala Pro Gly Glu Met Val Val Leu Thr
    210                 215                 220

Cys Asp Thr Pro Glu Glu Asp Gly Ile Thr Trp Thr Leu Asp Gln Ser
225                 230                 235                 240

Ser Glu Val Leu Gly Ser Gly Lys Thr Leu Thr Ile Gln Val Lys Glu
```

```
                        245                 250                 255
Phe Gly Asp Ala Gly Gln Tyr Thr Cys His Lys Gly Gly Glu Val Leu
                260                 265                 270
Ser His Ser Leu Leu Leu His Lys Lys Glu Asp Gly Ile Trp Ser
            275                 280                 285
Thr Asp Ile Leu Lys Asp Gln Lys Glu Pro Lys Asn Lys Thr Phe Leu
        290                 295                 300
Arg Cys Glu Ala Lys Asn Tyr Ser Gly Arg Phe Thr Cys Trp Trp Leu
305                 310                 315                 320
Thr Thr Ile Ser Thr Asp Leu Thr Phe Ser Val Lys Ser Ser Arg Gly
                325                 330                 335
Ser Ser Asp Pro Gln Gly Val Thr Cys Gly Ala Ala Thr Leu Ser Ala
                340                 345                 350
Glu Arg Val Arg Gly Asp Asn Lys Glu Tyr Glu Tyr Ser Val Glu Cys
                355                 360                 365
Gln Glu Asp Ser Ala Cys Pro Ala Ala Glu Glu Ser Leu Pro Ile Glu
            370                 375                 380
Val Met Val Asp Ala Val His Lys Leu Lys Tyr Glu Asn Tyr Thr Ser
385                 390                 395                 400
Ser Phe Phe Ile Arg Asp Ile Ile Lys Pro Asp Pro Pro Lys Asn Leu
                405                 410                 415
Gln Leu Lys Pro Leu Lys Asn Ser Arg Gln Val Glu Val Ser Trp Glu
                420                 425                 430
Tyr Pro Asp Thr Trp Ser Thr Pro His Ser Tyr Phe Ser Leu Thr Phe
            435                 440                 445
Cys Val Gln Val Gln Gly Lys Ser Lys Arg Glu Lys Lys Asp Arg Val
    450                 455                 460
Phe Thr Asp Lys Thr Ser Ala Thr Val Ile Cys Arg Lys Asn Ala Ser
465                 470                 475                 480
Ile Ser Val Arg Ala Gln Asp Arg Tyr Tyr Ser Ser Ser Trp Ser Glu
                485                 490                 495
Trp Ala Ser Val Pro Cys Ser
                500
```

METHOD OF TREATING PSORIASIS WITH INCREASED INTERVAL DOSING OF ANTI-IL12/23 ANTIBODY

CROSS-REFERENCE TO RELATED APPLICATION

This application claims the benefit of priority of U.S. Provisional Application No. 62/314,697, filed Mar. 29, 2016, the entire contents of which are incorporated herein by reference in their entireties.

FIELD OF THE INVENTION

The present invention concerns methods for treating an IL-12/23-related disease with an antibody that binds human IL-12 and/or human IL-23 proteins using specific dosing regimens. In particular, it relates to identification of an increased dosing (or maintenance) interval for subcutaneously administered anti-IL-12/23p40 antibody and specific pharmaceutical compositions of an antibody, e.g., ustekinumab, which are safe and effective for administration to patients with an IL-12/23-related disease.

BACKGROUND OF THE INVENTION

Interleukin (IL)-12 is a secreted heterodimeric cytokine comprised of 2 disulfide-linked glycosylated protein subunits, designated p35 and p40 for their approximate molecular weights. IL-12 is produced primarily by antigen-presenting cells and drives cell-mediated immunity by binding to a two-chain receptor complex that is expressed on the surface of T cells or natural killer (NK) cells. The IL-12 receptor beta-1 (IL-12Rβ1) chain binds to the p40 subunit of IL-12, providing the primary interaction between IL-12 and its receptor. However, it is IL-12p35 ligation of the second receptor chain, IL-12Rβ2, that confers intracellular signaling (e.g. STAT4 phosphorylation) and activation of the receptor-bearing cell (Presky et al, 1996). IL-12 signaling concurrent with antigen presentation is thought to invoke T cell differentiation towards the T helper 1 (Th1) phenotype, characterized by interferon gamma (IFNγ) production (Trinchieri, 2003). Th1 cells are believed to promote immunity to some intracellular pathogens, generate complement-fixing antibody isotypes, and contribute to tumor immunosurveillance. Thus, IL-12 is thought to be a significant component to host defense immune mechanisms.

It was discovered that the p40 protein subunit of IL-12 can also associate with a separate protein subunit, designated p19, to form a novel cytokine, IL-23 (Oppman et al, 2000). IL-23 also signals through a two-chain receptor complex. Since the p40 subunit is shared between IL-12 and IL-23, it follows that the IL-12Rβ1 chain is also shared between IL-12 and IL-23. However, it is the IL-23p19 ligation of the second component of the IL-23 receptor complex, IL-23R, that confers IL-23 specific intracellular signaling (e.g., STAT3 phosphorylation) and subsequent IL-17 production by T cells (Parham et al, 2002; Aggarwal et al. 2003). Studies have demonstrated that the biological functions of IL-23 are distinct from those of IL-12, despite the structural similarity between the two cytokines (Langrish et al, 2005).

Abnormal regulation of IL-12 and Th1 cell populations has been associated with many immune-mediated diseases since neutralization of IL-12 by antibodies is effective in treating animal models of psoriasis, multiple sclerosis (MS), rheumatoid arthritis, inflammatory bowel disease, insulin-dependent (type 1) diabetes mellitus, and uveitis (Leonard et al, 1995; Hong et al, 1999; Malfait et al, 1998; Davidson et al, 1998). However, since these studies targeted the shared p40 subunit, both IL-12 and IL-23 were neutralized in vivo. Therefore, it was unclear whether IL-12 or IL-23 was mediating disease, or if both cytokines needed to be inhibited to achieve disease suppression. Additional studies have confirmed through IL-23p19 deficient mice or specific antibody neutralization of IL-23 that IL-23 inhibition can provide equivalent benefit as anti-IL-12p40 strategies (Cua et al, 2003, Murphy et al, 2003, Benson et al 2004). Therefore, there is evidence for the roles of IL-12 and IL-23 in immune-mediated disease Psoriasis is a chronic immune-mediated skin disorder with significant co-morbidities, such as psoriatic arthritis (PsA), depression, cardiovascular disease, hypertension, obesity, diabetes, metabolic syndrome, and Crohn's disease. Plaque psoriasis is the most common form of the disease and manifests in well demarcated erythematous lesions topped with white silver scales. Plaques are pruritic, painful and often disfiguring and a significant proportion of psoriatic patients have plaques on hands/nails face, feet and genitalia. As such, psoriasis can impose physical and psychosocial burdens that extend beyond the physical dermatological symptoms and interfere with everyday activities. For example, psoriasis negatively impacts familial, spousal, social, and work relationships, and is associated with a higher incidence of depression and increased suicidal tendencies.

Histologic characterization of psoriasis lesions reveals a thickened epidermis resulting from aberrant keratinocyte proliferation and differentiation as well as dermal infiltration and co-localization of CD3+T lymphocytes and dendritic cells. While the etiology of psoriasis is not well defined, gene and protein analysis have shown that IL-12, IL-23 and their downstream molecules are over-expressed in psoriatic lesions, and some may correlate with psoriasis disease severity. Some therapies used in the treatment of psoriasis modulate IL-12 and IL-23 levels, which is speculated to contribute to their efficacy. Th1 and Th17 cells can produce effector cytokines that induce the production of vasodilators, chemoattractants and expression of adhesion molecules on endothelial cells which in turn, promote monocyte and neutrophil recruitment, T cell infiltration, neovascularization and keratinocyte activation and hyperplasia. Activated keratinocytes can produce chemoattractant factors that promote neutrophil, monocyte, T cell, and dendritic cell trafficking, thus establishing a cycle of inflammation and keratinocyte hyperproliferation.

Results of three phase 3 clinical studies of the IL-12/23 antibody ustekinumab in the treatment of moderate-to-severe plaque psoriasis have been published. Ustekinumab administered by subcutaneous injection at weeks 0 and 4 and then once every 12 weeks exhibited rapid and sustained clinical response, as assessed by the Psoriasis Area and Severity Index, a validated efficacy tool for psoriasis. A Phase 3 study comparing ustekinumab with etanercept, a TNF antagonist, demonstrated that the efficacy of ustekinumab was superior to that of etanercept over a 12-week period in patients with moderate-to-severe psoriasis. In two phase 3 clinical studies, Phoenix I and Phoenix II, ustekinumab exhibited a half life of approximately 3 weeks. Immune response rates against ustekinumab ranged from 3 to 5%. In addition, reported adverse events were relatively mild, with the majority of events including susceptibility to mild infections such as nasopharyngitis and upper respiratory tract infection. Rates of infection were not higher in ustekinumab-treated patients when compared with placebo-treated patients over 12 weeks of therapy; nor were they increased in association with higher, relative to lower, ustekinumab doses. Also, rates of serious infections, cardiovascular events, injection site reactions, and malignancies were low. Taken together, the clinical observations of ustekinumab in psoriasis have supported its first-in-class status and confirmed the fundamental role of IL-12 and/or IL-23 in psoriasis pathogenesis.

SUMMARY OF THE INVENTION

In a first aspect, the invention concerns a method of treating an IL-12/23-related disease in a patient comprising subcutaneously administering an anti-IL-12 and/or anti-IL-23 antibody, e.g., an anti-IL-12/23p40 (IL-12/23p40) antibody, to the patient, wherein the anti-IL-12/23p40 antibody is administered at an initial dose, a dose 4 weeks thereafter, and at a dosing interval of once every 12 weeks and that interval (the maintenance interval) is increased 28 weeks after the initial dose. The increased dosing interval can be a set interval or customized based on when a patient experiences reappearance of the disease state after withdrawal of or increased interval for administration of the antibody therapy, e.g., in psoriasis a change in PGA and/or PASI scores. In one embodiment, after 28 weeks the dosing interval is increased from once every 12 weeks to once every 16, 20 or 24 weeks at 45 mg or 90 mg doses.

In an embodiment, the IL-12/23-related disease is selected from the group consisting of psoriasis, psoriatic arthritis, lupus, diabetes, Crohn's disease, ulcerative colitis and other inflammatory bowel diseases, sarcoidosis, ankylosing spondylitis (AS) and axial spondyloarthritis (nrAxSpA). In a preferred embodiment, the IL-12/23-related disease is psoriasis. In another embodiment, the IL-12/23-related disease is psoriatic arthritis.

The invention also concerns a method of treating psoriasis in a patient comprising subcutaneously administering the anti-IL-12/23p40 antibody ustekinumab (Stelara®) to the patient, wherein the ustekinumab is administered initially, 4 weeks after the initial dose, at a dosing interval of once every 12 weeks until 28 weeks after an initial dose and then is administered once every 16, 20 or 24 weeks.

In addition, the composition used in the method of the invention comprises a pharmaceutical composition comprising: an anti-IL-12/23p40 antibody in an amount from about 1.0 µg/ml to about 1000 mg/ml, specifically a 45 mg or 90 mg dose. In a preferred embodiment the anti-IL-12/23p40 antibody is ustekinumab (Stelara®). In another embodiment, the pharmaceutical composition comprises an isolated anti-IL-12/IL-23p40 antibody that binds a peptide chain comprising residues 1-88 of SEQ ID NO: 9; from about 0.27 to about 0.80 mg L-histidine per ml of the pharmaceutical composition; from about 0.69 to about 2.1 mg L-histidine monohydrochloride monohydrate per ml of the pharmaceutical composition; from about 0.02 to about 0.06 mg polysorbate 80 per ml of the pharmaceutical composition; and from about 65 to about 87 mg of sucrose per ml of the pharmaceutical composition; wherein the diluent is water at standard state.

In another aspect of the invention the pharmaceutical composition comprises an isolated anti-IL-12/IL-23p40 antibody having (i) the heavy chain CDR amino acid sequences of SEQ ID NO: 1, SEQ ID NO: 2, and SEQ ID NO: 3; and (ii) the light chain CDR amino acid sequences of SEQ ID NO: 4, SEQ ID NO: 5, and SEQ ID NO: 6; from about 0.27 to about 0.80 mg L-histidine per ml of the pharmaceutical composition; from about 0.69 to about 2.1 mg L-histidine monohydrochloride monohydrate per ml of the pharmaceutical composition; from about 0.02 to about 0.06 mg polysorbate 80 per ml of the pharmaceutical composition; and from about 65 to about 87 mg of sucrose per ml of the pharmaceutical composition; wherein the diluent is water at standard state.

Another aspect of the method of the invention comprises administering a pharmaceutical composition comprising an isolated anti-IL-12/IL-23p40 antibody having the heavy chain variable region amino acid sequence of SEQ ID NO: 7 and the light chain variable region amino acid sequence of SEQ ID NO: 8; from about 0.27 to about 0.80 mg L-histidine per ml of the pharmaceutical composition; from about 0.69 to about 2.1 mg L-histidine monohydrochloride monohydrate per ml of the pharmaceutical composition; from about 0.02 to about 0.06 mg polysorbate 80 per ml of the pharmaceutical composition; and from about 65 to about 87 mg of sucrose per ml of the pharmaceutical composition; wherein the diluent is water at standard state.

Another aspect of the method is administering a pharmaceutical composition comprising an isolated anti-IL-12/IL-23p40 antibody having (i) the heavy chain CDR amino acid sequences of SEQ ID NO: 1, SEQ ID NO: 2, and SEQ ID NO: 3; and (ii) the light chain CDR amino acid sequences of SEQ ID NO: 4, SEQ ID NO: 5, and SEQ ID NO: 6; about 0.53 mg L-histidine per ml of the pharmaceutical composition; about 1.37 mg L-histidine monohydrochloride monohydrate per ml of the pharmaceutical composition; about 0.04 mg polysorbate 80 per ml of the pharmaceutical composition; and about 76 mg of sucrose per ml of the pharmaceutical composition; wherein the diluent is water at standard state.

A further aspect of the method is administering a pharmaceutical composition comprising an isolated anti-IL-12/IL-23p40 antibody having the heavy chain variable region amino acid sequence of SEQ ID NO: 7 and the light chain variable region amino acid sequence of SEQ ID NO: 8 wherein the isolated antibody binds a peptide chain comprising residues 1-88 of SEQ ID NO: 9; about 0.53 mg L-histidine per ml of the pharmaceutical composition; about 1.37 mg L-histidine monohydrochloride monohydrate per ml of the pharmaceutical composition; about 0.04 mg polysorbate 80 per ml of the pharmaceutical composition; and about 76 mg of sucrose per ml of the pharmaceutical composition; wherein the diluent is water at standard state.

In another aspect of the method is administering a pharmaceutical composition comprising a binding compound that competes for binding with the above-described antibodies, optionally at residues 1-88 of SEQ ID NO: 9; from about 0.27 to about 0.80 mg L-histidine per ml of the pharmaceutical composition; from about 0.69 to about 2.1 mg L-histidine monohydrochloride monohydrate per ml of the pharmaceutical composition; from about 0.02 to about 0.06 mg polysorbate 80 per ml of the pharmaceutical composition; and from about 65 to about 87 mg of sucrose per ml of the pharmaceutical composition; wherein the diluent is water at standard state.

DETAILED DESCRIPTION OF THE PREFERRED EMBODIMENTS

Figure 1:
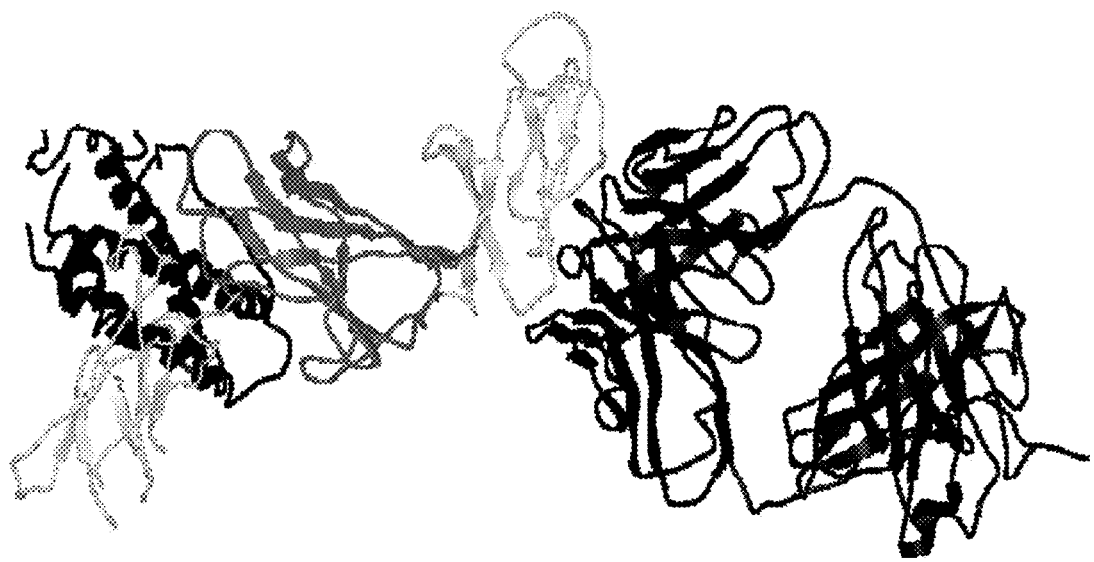
FIG. 1 shows the molecular structure of the bound complex of IL-12/p40 Fab in a ribbon representation.

As used herein the method of treatment of psoriasis comprises administering isolated, recombinant and/or synthetic anti-IL-12, IL-23 and IL12/23p40 human antibodies and diagnostic and therapeutic compositions, methods and devices.

As used herein, an "anti-IL-12 antibody," "anti-IL-23 antibody," "anti-IL-12/23p40 antibody," "IL-12/23p40 antibody," "antibody portion," or "antibody fragment" and/or "antibody variant" and the like include any protein or peptide containing molecule that comprises at least a portion of an immunoglobulin molecule, such as but not limited to, at least one complementarity determining region (CDR) of a heavy or light chain or a ligand binding portion thereof, a heavy chain or light chain variable region, a heavy chain or light chain constant region, a framework region, or any portion thereof, or at least one portion of an IL-12 and/or IL-23 receptor or binding protein, which can be incorporated into an antibody of the present invention. Such antibody optionally further affects a specific ligand, such as but not limited to, where such antibody modulates, decreases, increases, antagonizes, agonizes, mitigates, alleviates, blocks, inhibits, abrogates and/or interferes with at least one IL-12/23 activity or binding, or with IL-12/23 receptor activity or binding, in vitro, in situ and/or in vivo. As a non-limiting example, a suitable anti-IL-12/23p40 antibody, specified portion or variant of the present invention can bind at least one IL-12/23 molecule, or specified portions, variants or domains thereof. A suitable anti-IL-12/23p40 antibody, specified portion, or variant can also optionally affect at least one of IL-12/23 activity or function, such as but not limited to, RNA, DNA or protein synthesis, IL-12/23 release, IL-12/23 receptor signaling, membrane IL-12/23 cleavage, IL-12/23 activity, IL-12/23 production and/or synthesis.

The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to a mammalian IL-12/23. For example, antibody fragments capable of binding to IL-12/23 or portions thereof, including, but not limited to, Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the $C_H1$ domain and/or hinge region of the heavy chain. The various portions of antibodies can be joined together chemically by conventional techniques, or can be prepared as a contiguous protein using genetic engineering techniques.

As used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially non-immunogenic in humans, with only minor sequence changes or variations. A "human antibody" may also be an antibody that is derived from or closely matches human germline immunoglobulin sequences. Human antibodies may include amino acid residues not encoded by germline immunoglobulin sequences (e.g., mutations introduced by random or site-specific mutagenesis in vitro or by somatic mutation in vivo). Often, this means that the human antibody is substantially non-immunogenic in humans. Human antibodies have been classified into groupings based on their amino acid sequence similarities. Accordingly, using a sequence similarity search, an antibody with a similar linear sequence can be chosen as a template to create a human antibody. Similarly, antibodies designated primate (monkey, baboon, chimpanzee, etc.), rodent (mouse, rat, rabbit, guinea pig, hamster, and the like) and other mammals designate such species, sub-genus, genus, sub-family, and family specific antibodies. Further, chimeric antibodies can include any combination of the above. Such changes or variations optionally and preferably retain or reduce the immunogenicity in humans or other species relative to non-modified antibodies. Thus, a human antibody is distinct from a chimeric or humanized antibody.

It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Bispecific, heterospecific, heteroconjugate or similar antibodies can also be used that are monoclonal, preferably, human or humanized, antibodies that have binding specificities for at least two different antigens. In the present case, one of the binding specificities is for at least one IL-12/23 protein, the other one is for any other antigen. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed, e.g., in WO 93/08829, U.S. Pat. Nos. 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986), each entirely incorporated herein by reference.

Anti-IL-12/23p40 antibodies (also termed IL-12/23p40 antibodies) (or antibodies to IL-23) useful in the methods and compositions of the present invention can optionally be characterized by high affinity binding to IL-12/23p40 (or to IL-23) and, optionally and preferably, having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titres in the patient treated (less than about 300, preferably less than about 100 measured with a double antigen enzyme immunoassay) (Elliott et al., Lancet 344: 1125-1127 (1994), entirely incorporated herein by reference). "Low immunogenicity" can also be defined as the incidence of titrable levels of antibodies to the anti-IL-12 antibody in patients treated with anti-IL-12 antibody as occurring in less than 25% of patients treated, preferably, in less than 10% of patients treated with the recommended dose for the recommended course of therapy during the treatment period.

Utility

The isolated nucleic acids of the present invention can be used for production of at least one anti-IL-12/23p40 (or anti-IL-23) antibody or specified variant thereof, which can be used to measure or effect in an cell, tissue, organ or animal (including mammals and humans), to diagnose, monitor, modulate, treat, alleviate, help prevent the incidence of, or reduce the symptoms of, at least one IL-12/23 condition, selected from, but not limited to, at least one of an immune disorder or disease, a cardiovascular disorder or disease, an infectious, malignant, and/or neurologic disorder or disease, or other known or specified IL-12/23 related condition.

Such a method can comprise administering an effective amount of a composition or a pharmaceutical composition comprising at least one anti-IL-12/23p40 (or anti-IL-23) antibody to a cell, tissue, organ, animal or patient in need of such modulation, treatment, alleviation, prevention, or reduction in symptoms, effects or mechanisms. The effective amount can comprise an amount of about 0.001 to 500 mg/kg per single (e.g., bolus), multiple or continuous administration, or to achieve a serum concentration of 0.01-5000 µg/ml serum concentration per single, multiple, or continuous administration, or any effective range or value therein, as done and determined using known methods, as described herein or known in the relevant arts.

CITATIONS

All publications or patents cited herein, whether or not specifically designated, are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, NY (1987-2001); Sambrook, et al., Molecular Cloning: A Laboratory Manual, $2^{nd}$ Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, NY, (1997-2001).

Antibodies of the Present Invention—Production and Generation

At least one anti-IL-12/23p40 (or anti-IL-23) antibody used in the method of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, NY (1987-2001); Sambrook, et al., Molecular Cloning: A Laboratory Manual, $2^{nd}$ Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, NY, (1997-2001), each entirely incorporated herein by reference.

A preferred anti-IL-12/23p40 antibody is ustekinumab (Stelara®) having the heavy chain variable region amino acid sequence of SEQ ID NO: 7 and the light chain variable region amino acid sequence of SEQ ID NO: 8 and having the heavy chain CDR amino acid sequences of SEQ ID NO: 1, SEQ ID NO: 2, and SEQ ID NO: 3; and the light chain CDR amino acid sequences of SEQ ID NO: 4, SEQ ID NO: 5, and SEQ ID NO: 6. A preferred anti-IL-23 antibody (binding specifically to IL-23 and not IL-12) is guselkumab (also referred to as CNTO1959 that comprises the variable region sequences of SEQ ID NOS: 106 and 116 in U.S. Pat. No. 7,935,344, the entire contents of which are incorporated herein by reference) and other antibodies described in U.S. Pat. No. 7,935,344.

Human antibodies that are specific for human IL-12/23p40 or IL-23 proteins or fragments thereof can be raised against an appropriate immunogenic antigen, such as an isolated IL-12/23p40 protein, IL-23 protein and/or a portion thereof (including synthetic molecules, such as synthetic peptides). Other specific or general mammalian antibodies can be similarly raised. Preparation of immunogenic antigens, and monoclonal antibody production can be performed using any suitable technique.

In one approach, a hybridoma is produced by fusing a suitable immortal cell line (e.g., a myeloma cell line, such as, but not limited to, Sp2/0, Sp2/0-AG14, NS0, NS1, NS2, AE-1, L.5, L243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMALWA, NEURO 2A, or the like, or heteromylomas, fusion products thereof, or any cell or fusion cell derived therefrom, or any other suitable cell line as known in the art) (see, e.g., www.atcc.org, www.lifetech.com., and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Antibody producing cells can also be obtained from the peripheral blood or, preferably, the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsreid/Planegg, DE; Biovation, Aberdeen, Scotland, UK; BioInvent, Lund, Sweden; Dyax Corp., Enzon, Affymax/Biosite; Xoma, Berkeley, Calif.; Ixsys. See, e.g., EP 368,684, PCT/GB91/01134; PCT/GB92/01755; PCT/GB92/002240; PCT/GB92/00883; PCT/GB93/00605; U.S. Ser. No. 08/350,260 (May 12, 1994); PCT/GB94/01422; PCT/GB94/02662; PCT/GB97/01835; (CAT/MRC); WO90/14443; WO90/14424; WO90/14430; PCT/US94/1234; WO92/18619; WO96/07754; (Scripps); WO96/13583, WO97/08320 (MorphoSys); WO95/16027 (BioInvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or proteins—U.S. Pat. Nos. 5,723,323, 5,763,192, 5,814,476, 5,817,483, 5,824,514, 5,976,862, WO 86/05803, EP 590 689 (Ixsys, predecessor of Applied Molecular Evolution (AME), each entirely incorporated herein by reference)) or that rely upon immunization of transgenic animals (e.g., SCID mice, Nguyen et al., Microbiol. Immunol. 41:901-907 (1997); Sandhu et al., Crit. Rev. Biotechnol. 16:95-118 (1996); Eren et al., Immunol. 93:154-161 (1998), each entirely incorporated by reference as well as related patents and applications) that are capable of producing a repertoire of human antibodies, as known in the art and/or as described herein. Such techniques, include, but are not limited to, ribosome display (Hanes et al., Proc. Natl. Acad. Sci. USA, 94:4937-4942 (May 1997); Hanes et al., Proc. Natl. Acad. Sci. USA, 95:14130-14135 (November 1998)); single cell antibody producing technologies (e.g., selected lymphocyte antibody method ("SLAM") (U.S. Pat. No. 5,627,052, Wen et al., J. Immunol. 17:887-892 (1987); Babcook et al., Proc. Natl. Acad. Sci. USA 93:7843-7848 (1996)); gel microdroplet and flow cytometry (Powell et al., Biotechnol. 8:333-337 (1990); One Cell Systems, Cambridge, Mass.; Gray et al., J. Imm. Meth. 182:155-163 (1995); Kenny et al., Bio/Technol. 13:787-790 (1995)); B-cell selection (Steenbakkers et al., Molec. Biol. Reports 19:125-134 (1994); Jonak et al., Progress Biotech, Vol. 5, In Vitro Immunization in Hybridoma Technology, Borrebaeck, ed., Elsevier Science Publishers B.V., Amsterdam, Netherlands (1988)).

Methods for engineering or humanizing non-human or human antibodies can also be used and are well known in the art. Generally, a humanized or engineered antibody has one or more amino acid residues from a source that is non-human, e.g., but not limited to, mouse, rat, rabbit, non-human primate or other mammal. These non-human amino acid residues are replaced by residues often referred to as "import" residues, which are typically taken from an "import" variable, constant or other domain of a known human sequence.

Known human Ig sequences are disclosed, e.g., www.ncbi.nlm.nih.gov/entrez/query.fcgi; www.ncbi.nih.gov/igblast; www.atcc.org/phage/hdb.html; www.mrc-cpe.cam.ac.uk/ALIGNMENTS.php; www.kabatdatabase.com/top.html; ftp.ncbi.nih.gov/repository/kabat; www.sciquest.com; www.abcam.com; www.antibodyresource.com/onlinecomp.html; www.public.iastate.edu/~pedro/research_tools.html; www.whfreeman.com/immunology/CH05/kuby05.htm; www.hhmi.org/grants/lectures/1996/vlab; www.path.cam.ac.uk/~mrc7/mikeimages.html; mcb.harvard.edu/BioLinks/Immunology.html; www.immunogylink.com; pathbox.wustl.edu/~hcenter/index.html; www.appliedbiosystems.com; www.nal.usda.gov/awic/pubs/antibody; www.m.ehime-u.ac.jp/~yasuhito/Elisa.html; www.biodesign.com; www.cancerresearchuk.org; www.biotech.ufl.edu; www.isac-net.org; baserv.uci.kun.nl/~jraats/links1.html; www.recab.uni-hd.de/immuno.bme.nwu.edu; www.mrc-cpe.cam.ac.uk; www.ibt.unam.mx/vir/V_mice.html; www.bioinf.org.uk/abs; antibody.bath.ac.uk; www.unizh.ch; www.cryst.bbk.ac.uk/~ubcg07s; www.nimr.mrc.ac.uk/CC/ccaewg/ccaewg.html; www.path.cam.ac.uk/~mrc7/humanisation/TAHHP.html; www.ibt.unam.mx/vir/structure/stat_aim.html; www.biosci.missouri.edu/smithgp/index.html; www.jerini.de; Kabat et al., Sequences of Proteins of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing antigen binding. Accordingly, part or all of the non-human or human CDR sequences are maintained while the non-human sequences of the variable and constant regions may be replaced with human or other amino acids.

Antibodies can also optionally be humanized or human antibodies engineered with retention of high affinity for the antigen and other favorable biological properties. To achieve this goal, humanized (or human) antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, framework (FR) residues can be selected and combined from the consensus and import sequences so that the desired antibody characteristic, such as increased affinity for the target antigen(s), is achieved.

In addition, the human IL-12/23p40 (or anti-IL-23) antibody used in the method of the present invention may comprise a human germline light chain framework. In particular embodiments, the light chain germline sequence is selected from human VK sequences including, but not limited to, A1, A10, A11, A14, A17, A18, A19, A2, A20, A23, A26, A27, A3, A30, A5, A7, B2, B3, L1, L10, L11, L12, L14, L15, L16, L18, L19, L2, L20, L22, L23, L24, L25, L4/18a, L5, L6, L8, L9, O1, O11, O12, O14, O18, O2, O4, and O8. In certain embodiments, this light chain human germline framework is selected from V1-11, V1-13, V1-16, V1-17, V1-18, V1-19, V1-2, V1-20, V1-22, V1-3, V1-4, V1-5, V1-7, V1-9, V2-1, V2-11, V2-13, V2-14, V2-15, V2-17, V2-19, V2-6, V2-7, V2-8, V3-2, V3-3, V3-4, V4-1, V4-2, V4-3, V4-4, V4-6, V5-1, V5-2, V5-4, and V5-6.

In other embodiments, the human IL-12/23p40 (or anti-IL-23) antibody used in the method of the present invention may comprise a human germline heavy chain framework. In particular embodiments, this heavy chain human germline framework is selected from VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81.

In particular embodiments, the light chain variable region and/or heavy chain variable region comprises a framework region or at least a portion of a framework region (e.g., containing 2 or 3 subregions, such as FR2 and FR3). In certain embodiments, at least FRL1, FRL2, FRL3, or FRL4 is fully human. In other embodiments, at least FRH1, FRH2, FRH3, or FRH4 is fully human. In some embodiments, at least FRL1, FRL2, FRL3, or FRL4 is a germline sequence (e.g., human germline) or comprises human consensus sequences for the particular framework (readily available at the sources of known human Ig sequences described above). In other embodiments, at least FRH1, FRH2, FRH3, or FRH4 is a germline sequence (e.g., human germline) or comprises human consensus sequences for the particular framework. In preferred embodiments, the framework region is a fully human framework region.

Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766886, 5714352, 6204023, 6180370, 5693762, 5530101, 5585089, 5225539; 4816567, PCT/: US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, included references cited therein.

In certain embodiments, the antibody comprises an altered (e.g., mutated) Fc region. For example, in some embodiments, the Fc region has been altered to reduce or enhance the effector functions of the antibody. In some embodiments, the Fc region is an isotype selected from IgM, IgA, IgG, IgE, or other isotype. Alternatively or additionally, it may be useful to combine amino acid modifications with one or more further amino acid modifications that alter C1q binding and/or the complement dependent cytotoxicity function of the Fc region of an IL-12 binding molecule. The starting polypeptide of particular interest may be one that binds to C q and displays complement dependent cytotoxicity (CDC). Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO0042072, which is hereby incorporated by reference.

As disclosed above, one can design an Fc region of the human IL-12/23p40 (or anti-IL-23) antibody of the present invention with altered effector function, e.g., by modifying C1q binding and/or FcγR binding and thereby changing complement dependent cytotoxicity (CDC) activity and/or antibody-dependent cell-mediated cytotoxicity (ADCC) activity. "Effector functions" are responsible for activating or diminishing a biological activity (e.g., in a subject). Examples of effector functions include, but are not limited to: C1q binding; CDC; Fc receptor binding; ADCC; phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of the human IL-12/23p40 (or anti-IL-23) antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

Fc mutations can also be introduced in engineer to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, J. Biol. Chem. 276:6591-6604).

Another type of amino acid substitution serves to alter the glycosylation pattern of the Fc region of the human IL-12/23p40 (or anti-IL-23) antibody. Glycosylation of an Fc region is typically either N-linked or O-linked. N-linked refers to the attachment of the carbohydrate moiety to the side chain of an asparagine residue. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation sites that are not present in the polypeptide. Addition of glycosylation sites to the Fc region of a human IL-12/23p40 (or anti-IL-23) antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the human IL-12/23p40 (or anti-IL-23) antibody of the present invention is expressed in cells that express beta (1,4)-N-acetylglucosaminyltransferase III (GnT III), such that GnT III adds GlcNAc to the human IL-12 antibody. Methods for producing antibodies in such a fashion are provided in WO/9954342, WO/03011878, patent publication 20030003097A1, and Umana et al., Nature Biotechnology, 17:176-180, February 1999; all of which are herein specifically incorporated by reference in their entireties.

The anti-IL-12/23p40 (or anti-IL-23) antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-IL-12/23p40 (or anti-IL-23) antibody can be isolated from such animals and immortalized using suitable methods, such as the methods described herein.

Transgenic mice that can produce a repertoire of human antibodies that bind to human antigens can be produced by known methods (e.g., but not limited to, U.S. Pat. Nos. 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. Nature 368:856-859 (1994), Taylor et al., Int. Immunol. 6(4)579-591 (1994), Green et al, Nature Genetics 7:13-21 (1994), Mendez et al., Nature Genetics 15:146-156 (1997), Taylor et al., Nucleic Acids Research 20(23):6287-6295 (1992), Tuaillon et al., Proc Natl Acad Sci USA 90(8)3720-3724 (1993), Lonberg et al., Int Rev Immunol 13(1):65-93 (1995) and Fishwald et al., Nat Biotechnol 14(7):845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Screening antibodies for specific binding to similar proteins or fragments can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278.

Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643,768. Peptide display libraries, vector, and screening kits are commercially available from such suppliers as Invitrogen (Carlsbad, Calif.), and Cambridge antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, 5427908, 5580717, assigned to Affymax; 5885793, assigned to Cambridge antibody Technologies; 5750373, assigned to Genentech, 5618920, 5595898, 5576195, 5698435, 5693493, 5698417, assigned to Xoma, Colligan, supra; Ausubel, supra; or Sambrook, supra, each of the above patents and publications entirely incorporated herein by reference.

Antibodies used in the method of the present invention can also be prepared using at least one anti-IL-12/23p40 (or anti-IL-23) antibody encoding nucleic acid to provide transgenic animals or mammals, such as goats, cows, horses, sheep, rabbits, and the like, that produce such antibodies in their milk. Such animals can be provided using known methods. See, e.g., but not limited to, U.S. Pat. Nos. 5,827, 690; 5,849,992; 4,873,316; 5,849,992; 5,994,616; 5,565, 362; 5,304,489, and the like, each of which is entirely incorporated herein by reference.

Antibodies used in the method of the present invention can additionally be prepared using at least one anti-IL-12/23p40 (or anti-IL-23) antibody encoding nucleic acid to provide transgenic plants and cultured plant cells (e.g., but not limited to, tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101-109 (1998) and references cited therein. Thus, antibodies of the present invention can also be produced using transgenic plants, according to known methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109:341-6 (1995); Whitelam et al., Biochem. Soc. Trans. 22:940-944 (1994); and references cited therein. Each of the above references is entirely incorporated herein by reference.

The antibodies used in the method of the invention can bind human IL-12/23p40 (or IL-23) with a wide range of affinities ($K_D$). In a preferred embodiment, a human mAb can optionally bind human IL-12/23p40 (or IL-23) with high affinity. For example, a human mAb can bind human IL-12/23p40 (or IL-23) with a $K_D$ equal to or less than about $10^{-7}$ M, such as but not limited to, 0.1-9.9 (or any range or value therein)$\times 10^{-7}$, $10^{-8}$, $10^{-9}$, $10^{-10}$, $10^{-11}$, $10^{-12}$, $10^{-13}$ or any range or value therein.

The affinity or avidity of an antibody for an antigen can be determined experimentally using any suitable method. (See, for example, Berzofsky, et al., "Antibody-Antigen Interactions," In *Fundamental Immunology*, Paul, W. E., Ed., Raven Press: New York, N.Y. (1984); Kuby, Janis *Immunology*, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

Nucleic Acid Molecules

Using the information provided herein, for example, the nucleotide sequences encoding at least 70-100% of the contiguous amino acids of at least one of the light or heavy chain variable or CDR regions of SEQ ID NOS: 1, 2, 3, 4, 5, 6, 7, 8, among other sequences disclosed herein, specified fragments, variants or consensus sequences thereof, or a deposited vector comprising at least one of these sequences, a nucleic acid molecule of the present invention encoding at least one anti-IL-12 antibody can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules used in the method of the present invention can include nucleic acid molecules comprising an open reading frame (ORF), optionally, with one or more introns, e.g., but not limited to, at least one specified portion of at least one CDR, such as CDR1, CDR2 and/or CDR3 of at least one heavy chain (e.g., SEQ ID NOS:1-3) or light chain (e.g., SEQ ID NOS:4-6); nucleic acid molecules comprising the coding sequence for an anti-IL-12/23p40 antibody or variable region (e.g., light and heavy chain variable regions of SEQ ID NOS:7 and 8); and nucleic acid molecules which comprise a nucleotide sequence substantially different from those described above but which, due to the degeneracy of the genetic code, still encode at least one anti-IL-12/23p40 (or anti-IL-23) antibody as described herein and/or as known in the art. Of course, the genetic code is well known in the art. Thus, it would be routine for one skilled in the art to generate such degenerate nucleic acid variants that code for specific anti-IL-12/23p40 (or anti-IL-23) antibodies used in the method of the present invention. See, e.g., Ausubel, et al., supra, and such nucleic acid variants are included in the present invention. Non-limiting examples of isolated nucleic acid molecules include nucleic acids encoding HC CDR1, HC CDR2, HC CDR3, LC CDR1, LC CDR2, and LC CDR3, respectively.

As indicated herein, nucleic acid molecules which comprise a nucleic acid encoding an anti-IL-12/23p40 (or anti-IL-23) antibody can include, but are not limited to, those encoding the amino acid sequence of an antibody fragment, by itself; the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example, ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

Polynucleotides Selectively Hybridizing to a Polynucleotide as Described Herein

The method of the present invention uses isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably, at least 85% or 90% full-length sequences, and, more preferably, at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides will encode at least a portion of an antibody. The polynucleotides embrace nucleic acid sequences that can be employed for selective hybridization to a polynucleotide encoding an antibody of the present invention. See, e.g., Ausubel, supra; Colligan, supra, each entirely incorporated herein by reference.

Construction of Nucleic Acids

The isolated nucleic acids can be made using (a) recombinant methods, (b) synthetic techniques, (c) purification techniques, and/or (d) combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention, excluding the coding sequence, is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

Recombinant Methods for Constructing Nucleic Acids

The isolated nucleic acid compositions, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, are well known to those of ordinary skill in the art. (See, e.g., Ausubel, supra; or Sambrook, supra)

Nucleic Acid Screening and Isolation Methods

A cDNA or genomic library can be screened using a probe based upon the sequence of a polynucleotide used in the method of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent, such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides used in the method of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The isolated nucleic acids used in the method of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The present invention uses recombinant expression cassettes comprising a nucleic acid. A nucleic acid sequence, for example, a cDNA or a genomic sequence encoding an antibody used in the method of the present invention, can be used to construct a recombinant expression cassette that can be introduced into at least one desired host cell. A recombinant expression cassette will typically comprise a polynucleotide operably linked to transcriptional initiation regulatory sequences that will direct the transcription of the polynucleotide in the intended host cell. Both heterologous and non-heterologous (i.e., endogenous) promoters can be employed to direct expression of the nucleic acids.

In some embodiments, isolated nucleic acids that serve as promoter, enhancer, or other elements can be introduced in the appropriate position (upstream, downstream or in the intron) of a non-heterologous form of a polynucleotide of the present invention so as to up or down regulate expression of a polynucleotide. For example, endogenous promoters can be altered in vivo or in vitro by mutation, deletion and/or substitution.

Vectors and Host Cells

The present invention also relates to vectors that include isolated nucleic acid molecules, host cells that are genetically engineered with the recombinant vectors, and the production of at least one anti-IL-12/23p40 (or anti-IL-23) antibody by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but are not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in *E. coli* and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one antibody used in the method of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein used in the method of the present invention. Alternatively, nucleic acids can be expressed in a host cell by turning on (by manipulation) in a host cell that contains endogenous DNA encoding an antibody. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www.atcc.org). Preferred host cells include cells of lymphoid origin, such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or a SP2/0-Agl4 cell.

Expression vectors for these cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Purification of an Antibody

An anti-IL-12/23-p40 (or anti-IL-23) antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, NY, (1997-2001), e.g., Chapters 1, 4, 6, 8, 9, 10, each entirely incorporated herein by reference.

Antibodies used in the method of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Anti-IL-12/IL-23p40 Antibodies.

An anti-IL-12/23p40 (or anti-IL-23) antibody according to the present invention includes any protein or peptide containing molecule that comprises at least a portion of an immunoglobulin molecule, such as but not limited to, at least one ligand binding portion (LBP), such as but not limited to, a complementarity determining region (CDR) of a heavy or light chain or a ligand binding portion thereof, a heavy chain or light chain variable region, a framework region (e.g., FR1, FR2, FR3, FR4 or fragment thereof, further optionally comprising at least one substitution, insertion or deletion), a heavy chain or light chain constant region, (e.g., comprising at least one $C_H1$, hinge1, hinge2, hinge3, hinge4, $C_H2$, or $C_H3$ or fragment thereof, further optionally comprising at least one substitution, insertion or deletion), or any portion thereof, that can be incorporated into an antibody. An antibody can include or be derived from any mammal, such as but not limited to, a human, a mouse, a rabbit, a rat, a rodent, a primate, or any combination thereof, and the like.

The isolated antibodies used in the method of the present invention comprise the antibody amino acid sequences disclosed herein encoded by any suitable polynucleotide, or any isolated or prepared antibody. Preferably, the human antibody or antigen-binding fragment binds human IL-12/23 or IL-23 and, thereby, partially or substantially neutralizes at least one biological activity of the protein. An antibody, or specified portion or variant thereof, that partially or preferably substantially neutralizes at least one biological activity of at least one IL-12 or IL-23 protein or fragment can bind the protein or fragment and thereby inhibit activities mediated through the binding of IL-12 or IL-23 to the IL-12 or IL-23 receptor or through other IL-12-dependent or mediated mechanisms. As used herein, the term "neutralizing antibody" refers to an antibody that can inhibit an IL-12 or IL-23-dependent activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an anti-IL-12/23p40 antibody to inhibit an IL-12/23-dependent activity is preferably assessed by at least one suitable IL-12/23 protein or receptor assay, as described herein and/or as known in the art. A human antibody can be of any class (IgG, IgA, IgM, IgE, IgD, etc.) or isotype and can comprise a kappa or lambda light chain. In one embodiment, the human antibody comprises an IgG heavy chain or defined fragment, for example, at least one of isotypes, IgG1, IgG2, IgG3 or IgG4 (e.g., γ1, γ2, γ3, γ4). Antibodies of this type can be prepared by employing a transgenic mouse or other transgenic non-human mammal comprising at least one human light chain (e.g., IgG, IgA, and IgM) transgenes as described herein and/or as known in the art. In another embodiment, the anti-human IL-12/23p40 (or anti-IL-23) human antibody comprises an IgG1 heavy chain and an IgG1 light chain.

An antibody binds at least one specified epitope specific to at least one IL-12/23 protein, subunit, fragment, portion or any combination thereof. The at least one epitope can comprise at least one antibody binding region that comprises at least one portion of the protein, which epitope is preferably comprised of at least one extracellular, soluble, hydrophillic, external or cytoplasmic portion of the protein. The at least one specified epitope can comprise any combination of at least one amino acid sequence of at least 1-3 amino acids to the entire specified portion of contiguous amino acids of SEQ ID NO:9, for example, amino acid residues 15, 17-21, 23, 40-43, 45-47, 54-56 and 58-62.

Generally, the human antibody or antigen-binding fragment will comprise an antigen-binding region that comprises at least one human complementarity determining region (CDR1, CDR2 and CDR3) or variant of at least one heavy chain variable region and at least one human complementarity determining region (CDR1, CDR2 and CDR3) or variant of at least one light chain variable region. The CDR sequences may be derived from human germline sequences or closely match the germline sequences. For example, the CDRs from a synthetic library derived from the original non-human CDRs can be used. These CDRs may be formed by incorporation of conservative substitutions from the original non-human sequence. As a non-limiting example, the antibody or antigen-binding portion or variant can comprise at least one of the heavy chain CDR3 having an amino acid sequence selected from the group consisting of SEQ ID NOS: 1-3, and/or a light chain CDR3 having an amino acid sequence selected from the group consisting of SEQ ID NOS:4-6. In a particular embodiment, the antibody or antigen-binding fragment can have an antigen-binding region that comprises at least a portion of at least one heavy chain CDR (i.e., CDR1, CDR2 and/or CDR3) having the amino acid sequence of the corresponding CDRs 1, 2, and/or 3 (e.g., SEQ ID NOS: 1, 2, and/or 3). In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3.

Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

The anti-IL-12/23p40 (or anti-IL-23) antibody can comprise at least one of a heavy or light chain variable region having a defined amino acid sequence. For example, in a preferred embodiment, the anti-IL-12/23p40 antibody comprises at least one of at least one heavy chain variable region, optionally having the amino acid sequence of SEQ ID NO:7 and/or at least one light chain variable region, optionally having the amino acid sequence of SEQ ID NO:8.

Antibodies that bind to human IL-12/23 and that comprise a defined heavy or light chain variable region can be prepared using suitable methods, such as phage display (Katsube, Y., et al., *Int J Mol. Med,* 1(5):863-868 (1998)) or methods that employ transgenic animals, as known in the art and/or as described herein. For example, a transgenic mouse, comprising a functionally rearranged human immunoglobulin heavy chain transgene and a transgene comprising DNA from a human immunoglobulin light chain locus that can undergo functional rearrangement, can be immunized with human IL-12/23 or a fragment thereof to elicit the production of antibodies. If desired, the antibody producing cells can be isolated and hybridomas or other immortalized antibody-producing cells can be prepared as described herein and/or as known in the art. Alternatively, the antibody, specified portion or variant can be expressed using the encoding nucleic acid or portion thereof in a suitable host cell.

The invention also relates to antibodies, antigen-binding fragments, immunoglobulin chains and CDRs comprising amino acids in a sequence that is substantially the same as an amino acid sequence described herein. Preferably, such antibodies or antigen-binding fragments and antibodies comprising such chains or CDRs can bind human IL-12/23 with high affinity (e.g., $K_D$ less than or equal to about $10^{-9}$ M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include, without limitation, replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Amino Acid Codes

The amino acids that make up anti-IL-12/23p40 (or anti-IL-23) antibodies of the present invention are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994):

| SINGLE LETTER CODE | THREE LETTER CODE | NAME | THREE NUCLEOTIDE CODON(S) |
|---|---|---|---|
| A | Ala | Alanine | GCA, GCC, GCG, GCU |
| C | Cys | Cysteine | UGC, UGU |
| D | Asp | Aspartic acid | GAC, GAU |
| E | Glu | Glutamic acid | GAA, GAG |
| F | Phe | Phenylanine | UUC, UUU |
| G | Gly | Glycine | GGA, GGC, GGG, GGU |
| H | His | Histidine | CAC, CAU |
| I | Ile | Isoleucine | AUA, AUC, AUU |
| K | Lys | Lysine | AAA, AAG |
| L | Leu | Leucine | UUA, UUG, CUA, CUC, CUG, CUU |

-continued

| SINGLE LETTER CODE | THREE LETTER CODE | NAME | THREE NUCLEOTIDE CODON(S) |
|---|---|---|---|
| M | Met | Methionine | AUG |
| N | Asn | Asparagine | AAC, AAU |
| P | Pro | Proline | CCA, CCC, CCG, CCU |
| Q | Gln | Glutamine | CAA, CAG |
| R | Arg | Arginine | AGA, AGG, CGA, CGC, CGG, CGU |
| S | Ser | Serine | AGC, AGU, UCA, UCC, UCG, UCU |
| T | Thr | Threonine | ACA, ACC, ACG, ACU |
| V | Val | Valine | GUA, GUC, GUG, GUU |
| W | Trp | Tryptophan | UGG |
| Y | Tyr | Tyrosine | UAC, UAU |

An anti-IL-12/23p40 (or anti-IL-23) antibody used in the method of the present invention can include one or more amino acid substitutions, deletions or additions, either from natural mutations or human manipulation, as specified herein.

The number of amino acid substitutions a skilled artisan would make depends on many factors, including those described above. Generally speaking, the number of amino acid substitutions, insertions or deletions for any given anti-IL-12/23p40 (or anti-IL-23) antibody, fragment or variant will not be more than 40, 30, 20, 19, 18, 17, 16, 15, 14, 13, 12, 11, 10, 9, 8, 7, 6, 5, 4, 3, 2, 1, such as 1-30 or any range or value therein, as specified herein.

Amino acids in an anti-IL-12/23p40 (or anti-IL-23) antibody that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to, at least one IL-12 or IL-23 neutralizing activity. Sites that are critical for antibody binding can also be identified by structural analysis, such as crystallization, nuclear magnetic resonance or photoaffinity labeling (Smith, et al., J. Mol. Biol. 224:899-904 (1992) and de Vos, et al., Science 255:306-312 (1992)). The residues on the IL-12/23p40 antibody involved in IL-12 binding have been identified based upon the co-crystal structure of the IL-12/23p40 antibody and IL-12 p40 antigen. These are shown in Table 5 below.

Anti-IL-12/23p40 antibodies can include, but are not limited to, at least one portion, sequence or combination selected from 5 to all of the contiguous amino acids of at least one of SEQ ID NOS:1, 2, 3, 4, 5, 6.

IL-12/23p40 antibodies or specified portions or variants can include, but are not limited to, at least one portion, sequence or combination selected from at least 3-5 contiguous amino acids of SEQ ID NO: 1, 5-17 contiguous amino acids of SEQ ID NO:2, 5-10 contiguous amino acids of SEQ ID NO:3, 5-11 contiguous amino acids of SEQ ID NO:4, 5-7 contiguous amino acids of SEQ ID NO:5; 5-9 contiguous amino acids of SEQ ID NO:6; Leu21, Lys76, Met83, Ser85 of SEQ ID NO:7.

An anti-IL-12/23p40 antibody can further optionally comprise a polypeptide of at least one of 70-100% of 5, 17, 10, 11, 7, 9, 119, or 108 contiguous amino acids of at least one of SEQ ID NOS:1, 2, 3, 4, 5, 6, 7 or 8. In one embodiment, the amino acid sequence of an immunoglobulin chain, or portion thereof (e.g., variable region, CDR) has about 70-100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of the corresponding chain of at least one of SEQ ID NOS: 1, 2, 3, 4, 5, 6, 7 or 8. For example, the amino acid sequence of a light chain variable region can be compared with the sequence of SEQ ID NOS: 4, 5, 6, or 8, or the amino acid sequence of a heavy chain CDR3 can be compared with SEQ ID NOS: 1, 2, 3, or 7. Preferably, 70-100% amino acid identity (i.e., 90, 91, 92, 93, 94, 95, 96, 97, 98, 99, 100 or any range or value therein) is determined using a suitable computer algorithm, as known in the art.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" and "similarity" can be readily calculated by known methods, including, but not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., Siam J. Applied Math., 48:1073 (1988). In addition, values for percentage identity can be obtained from amino acid and nucleotide sequence alignments generated using the default settings for the AlignX component of Vector NTI Suite 8.0 (Informax, Frederick, Md.).

Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215:403-410 (1990)). The BLAST X program is publicly available from NCBI and other sources (BLAST Manual, Altschul, S., et al., NCBINLM NIH Bethesda, Md. 20894: Altschul, S., et al., J. Mol. Biol. 215:403-410 (1990). The well-known Smith Waterman algorithm may also be used to determine identity.

Preferred parameters for polypeptide sequence comparison include the following:
(1) Algorithm: Needleman and Wunsch, J. Mol Biol. 48:443-453 (1970) Comparison matrix: BLOSSUM62 from Hentikoff and Hentikoff, Proc. Natl. Acad. Sci, USA. 89:10915-10919 (1992)
Gap Penalty: 12
Gap Length Penalty: 4
A program useful with these parameters is publicly available as the "gap" program from Genetics Computer Group, Madison Wis. The aforementioned parameters are the default parameters for peptide sequence comparisons (along with no penalty for end gaps).

Preferred parameters for polynucleotide comparison include the following:
(1) Algorithm: Needleman and Wunsch, J. Mol Biol. 48:443-453 (1970)
Comparison matrix: matches=+10, mismatch=0
Gap Penalty: 50
Gap Length Penalty: 3
Available as: The "gap" program from Genetics Computer Group, Madison Wis. These are the default parameters for nucleic acid sequence comparisons.

By way of example, a polynucleotide sequence may be identical to another sequence, that is 100% identical, or it may include up to a certain integer number of nucleotide alterations as compared to the reference sequence. Such alterations are selected from the group consisting of at least one nucleotide deletion, substitution, including transition and transversion, or insertion, and wherein the alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the sequence by the numerical percent of the respective percent identity (divided by 100) and subtracting that product from the total number of nucleotides in the sequence, or:

$n_n \ltorsim x_n - (x_n \cdot y)$, wherein $n_n$ is the number of nucleotide alterations, $x_n$ is the total number of nucleotides in sequence, and y is, for instance, 0.70 for 70%, 0.80 for 80%, 0.85 for 85%, 0.90 for 90%, 0.95 for 95%, etc., and wherein any non-integer product of $x_n$ and y is rounded down to the nearest integer prior to subtracting from $x_n$.

Alterations of a polynucleotide sequence encoding the polypeptide of SEQ ID NO: 7 may create nonsense, missense or frameshift mutations in this coding sequence and thereby alter the polypeptide encoded by the polynucleotide following such alterations. Similarly, a polypeptide sequence may be identical to the reference sequence of SEQ ID NO: 7, that is be 100% identical, or it may include up to a certain integer number of amino acid alterations as compared to the reference sequence such that the percentage identity is less than 100%. Such alterations are selected from the group consisting of at least one amino acid deletion, substitution, including conservative and non-conservative substitution, or insertion, and wherein the alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO: 7 by the numerical percent of the respective percent identity (divided by 100) and then subtracting that product from the total number of amino acids in SEQ ID NO: 7, or:

$n_a \ltorsim x_a - (x_a \cdot y)$, wherein $n_a$ is the number of amino acid alterations, $x_a$ is the total number of amino acids in SEQ ID NO: 7, and y is, for instance 0.70 for 70%, 0.80 for 80%, 0.85 for 85% etc., and wherein any non-integer produce of $x_a$ and y is rounded down to the nearest integer prior to subtracting it from $x_a$.

Exemplary heavy chain and light chain variable regions sequences and portions thereof are provided in SEQ ID NOS: 1-8. The antibodies of the present invention, or specified variants thereof, can comprise any number of contiguous amino acid residues from an antibody of the present invention, wherein that number is selected from the group of integers consisting of from 10-100% of the number of contiguous residues in an anti-IL-12 antibody. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, or 5.

As those of skill will appreciate, the present invention includes at least one biologically active antibody of the present invention. Biologically active antibodies have a specific activity at least 20%, 30%, or 40%, and, preferably, at least 50%, 60%, or 70%, and, most preferably, at least 80%, 90%, or 95%-100% or more (including, without limitation, up to 10 times the specific activity) of that of the native (non-synthetic), endogenous or related and known antibody. Methods of assaying and quantifying measures of enzymatic activity and substrate specificity are well known to those of skill in the art.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example, $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N, N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-Δ9-octadecanoate ($C_{18}$, oleate), all cis-Δ5,8,11,14-eicosatetraenoate ($C_{20}$, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably, one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups, such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., *Bioconjugate Techniques*, Academic Press: San Diego, Calif. (1996)). An activating group can be bonded directly to the organic group (e.g., hydrophilic polymer, fatty acid, fatty acid ester), or through a linker moiety, for example, a divalent C1-C12 group wherein one or more carbon atoms can be replaced by a heteroatom, such as oxygen, nitrogen or sulfur. Suitable linker moieties include, for example, tetraethylene glycol, —$(CH_2)_3$—, —NH—$(CH_2)_6$—NH—, —$(CH_2)_2$—NH— and —$CH_2$—O—$CH_2$—$CH_2$—O—$CH_2$—$CH_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate, as described, or can be reacted with maleic anhydride and the resulting product cyclized to produce an activated maleimido derivative of the fatty acid. (See, for example, Thompson, et al., WO 92/16221, the entire teachings of which are incorporated herein by reference.)

The modified antibodies can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention.

Modified human antibodies and antigen-binding fragments comprising an organic moiety that is bonded to specific sites of an antibody of the present invention can be prepared using suitable methods, such as reverse proteolysis (Fisch et al., *Bioconjugate Chem.*, 3:147-153 (1992); Werlen et al., *Bioconjugate Chem.*, 5:411-417 (1994); Kumaran et al., *Protein Sci.* 6(10):2233-2241 (1997); Itoh et al., *Bioorg. Chem.*, 24(1): 59-68 (1996); Capellas et al., *Biotechnol. Bioeng.*, 56(4):456-463 (1997)), and the methods described in Hermanson, G. T., *Bioconjugate Techniques*, Academic Press: San Diego, Calif. (1996).

The method of the present invention also uses an anti-IL-12/23p40 antibody composition comprising at least one, at least two, at least three, at least four, at least five, at least six or more anti-IL-12/23p40 antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the anti-IL-12/23p40 antibody amino acid sequence selected from the group consisting of 70-100% of the contiguous amino acids of SEQ ID NOS: 7 or 8, or specified fragments, domains or variants thereof. Preferred anti-IL-12/23p40 antibody compositions include at least one or two full length, fragments, domains or variants as at least one CDR or LBP containing portions of the anti-IL-12/23p40 antibody sequence described herein, for example, 70-100% of SEQ ID NOS: 1-6, 7, or 8, or specified fragments, domains or variants thereof. Further preferred compositions comprise, for example, 40-99% of at least one of 70-100% of SEQ ID NOS: 1-6, 7, or 8, etc., or specified fragments, domains or variants thereof. Such composition percentages are by weight, volume, concentration, molarity, or molality as liquid or dry solutions, mixtures, suspension, emulsions, particles, powder, or colloids, as known in the art or as described herein.

Antibody Compositions Comprising Further Therapeutically Active Ingredients

The antibody compositions used in the method of the invention can optionally further comprise an effective amount of at least one compound or protein selected from at least one of an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplastic, an immunomodulation drug, an ophthalmic, otic or nasal drug, a topical drug, a nutritional drug or the like. Such drugs are well known in the art, including formulations, indications, dosing and administration for each presented herein (see, e.g., Nursing 2001 Handbook of Drugs, 21$^{st}$ edition, Springhouse Corp., Springhouse, P A, 2001; Health Professional's Drug Guide 2001, ed., Shannon, Wilson, Stang, Prentice-Hall, Inc, Upper Saddle River, N.J.; Pharmcotherapy Handbook, Wells et al., ed., Appleton & Lange, Stamford, Conn., each entirely incorporated herein by reference).

By way of example of the drugs that can be combined with the antibodies for the method of the present invention, the anti-infective drug can be at least one selected from amebicides or at least one antiprotozoals, anthelmintics, antifungals, antimalarials, antituberculotics or at least one antileprotics, aminoglycosides, penicillins, cephalosporins, tetracyclines, sulfonamides, fluoroquinolones, antivirals, macrolide anti-infectives, and miscellaneous anti-infectives. The hormonal drug can be at least one selected from corticosteroids, androgens or at least one anabolic steroid, estrogen or at least one progestin, gonadotropin, antidiabetic drug or at least one glucagon, thyroid hormone, thyroid hormone antagonist, pituitary hormone, and parathyroid-like drug. The at least one cephalosporin can be at least one selected from cefaclor, cefadroxil, cefazolin sodium, cefdinir, cefepime hydrochloride, cefixime, cefmetazole sodium, cefonicid sodium, cefoperazone sodium, cefotaxime sodium, cefotetan disodium, cefoxitin sodium, cefpodoxime proxetil, cefprozil, ceftazidime, ceftibuten, ceftizoxime sodium, ceftriaxone sodium, cefuroxime axetil, cefuroxime sodium, cephalexin hydrochloride, cephalexin monohydrate, cephradine, and loracarbef.

The at least one corticosteroid can be at least one selected from betamethasone, betamethasone acetate or betamethasone sodium phosphate, betamethasone sodium phosphate, cortisone acetate, dexamethasone, dexamethasone acetate, dexamethasone sodium phosphate, fludrocortisone acetate, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, prednisolone, prednisolone acetate, prednisolone sodium phosphate, prednisolone tebutate, prednisone, triamcinolone, triamcinolone acetonide, and triamcinolone diacetate. The at least one androgen or anabolic steroid can be at least one selected from danazol, fluoxymesterone, methyltestosterone, nandrolone decanoate, nandrolone phenpropionate, testosterone, testosterone cypionate, testosterone enanthate, testosterone propionate, and testosterone transdermal system.

The at least one immunosuppressant can be at least one selected from azathioprine, basiliximab, cyclosporine, daclizumab, lymphocyte immune globulin, muromonab-CD3, mycophenolate mofetil, mycophenolate mofetil hydrochloride, sirolimus, and tacrolimus.

The at least one local anti-infective can be at least one selected from acyclovir, amphotericin B, azelaic acid cream, bacitracin, butoconazole nitrate, clindamycin phosphate, clotrimazole, econazole nitrate, erythromycin, gentamicin sulfate, ketoconazole, mafenide acetate, metronidazole (topical), miconazole nitrate, mupirocin, naftifine hydrochloride, neomycin sulfate, nitrofurazone, nystatin, silver sulfadiazine, terbinafine hydrochloride, terconazole, tetracycline hydrochloride, tioconazole, and tolnaftate. The at least one scabicide or pediculicide can be at least one selected from crotamiton, lindane, permethrin, and pyrethrins.

The at least one topical corticosteroid can be at least one selected from betamethasone dipropionate, betamethasone valerate, clobetasol propionate, desonide, desoximetasone, dexamethasone, dexamethasone sodium phosphate, diflorasone diacetate, fluocinolone acetonide, fluocinonide, flurandrenolide, fluticasone propionate, halcionide, hydrocortisone, hydrocortisone acetate, hydrocortisone butyrate, hydrocortisone valerate, mometasone furoate, and triamcinolone acetonide. (See, e.g., pp. 1098-1136 of Nursing 2001 Drug Handbook.) Anti-IL-12/23p40 (or anti-IL-23) antibody compositions can further comprise at least one of any suitable and effective amount of a composition or pharmaceutical composition comprising at least one anti-IL-12/23p40 (or anti-IL-23) antibody contacted or administered to a cell, tissue, organ, animal or patient in need of such modulation, treatment or therapy, optionally further comprising at least one selected from at least one TNF antagonist (e.g., but not limited to a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, eternacept, CDP-571, CDP-870, afelimomab, lenercept, and the like), an antirheumatic (e.g., methotrexate, auranofin, aurothioglucose, azathioprine, etanercept, gold sodium thiomalate, hydroxychloroquine sulfate, leflunomide, sulfasalzine), an immunization, an immunoglobulin, an immunosuppressive (e.g., basiliximab, cyclosporine, daclizumab), a cytokine or a cytokine antagonist. Non-limiting examples of such cytokines include, but are not limited to, any of IL-1 to IL-23 et al. (e.g., IL-1, IL-2, etc.). Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Anti-IL-12/23p40 antibody compounds, compositions or combinations used in the method of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., Remington's Pharmaceutical Sciences, $18^{th}$ Edition, Mack Publishing Co. (Easton, Pa.) 1990. Pharmaceutically acceptable carriers can be routinely selected that are suitable for the mode of administration, solubility and/or stability of the anti-IL-12/23p40 antibody, fragment or variant composition as well known in the art or as described herein.

Pharmaceutical excipients and additives useful in the present composition include, but are not limited to, proteins, peptides, amino acids, lipids, and carbohydrates (e.g., sugars, including monosaccharides, di-, tri-, tetra-, and oligosaccharides; derivatized sugars, such as alditols, aldonic acids, esterified sugars and the like; and polysaccharides or sugar polymers), which can be present singly or in combination, comprising alone or in combination 1-99.99% by weight or volume. Exemplary protein excipients include serum albumin, such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-IL-12/23p40 antibody (or anti-IL-23) compositions can also include a buffer or a pH adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts, such as citrate.

Additionally, anti-IL-12/23p40 (or anti-IL-23) antibody compositions can include polymeric excipients/additives, such as polyvinylpyrrolidones, ficolls (a polymeric sugar), dextrates (e.g., cyclodextrins, such as 2-hydroxypropyl-3-cyclodextrin), polyethylene glycols, flavoring agents, antimicrobial agents, sweeteners, antioxidants, antistatic agents, surfactants (e.g., polysorbates, such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the anti-IL-12/23p40 (or anti-IL-23) antibody, portion or variant compositions according to the invention are known in the art, e.g., as listed in "Remington: The Science & Practice of Pharmacy," $19^{th}$ ed., Williams & Williams, (1995), and in the "Physician's Desk Reference," $52^{nd}$ ed., Medical Economics, Montvale, N.J. (1998), the disclosures of which are entirely incorporated herein by reference. Preferred carrier or excipient materials are carbohydrates (e.g., saccharides and alditols) and buffers (e.g., citrate) or polymeric agents. An exemplary carrier molecule is the mucopolysaccharide, hyaluronic acid, which may be useful for intraarticular delivery.

Formulations

As noted above, the invention provides for stable formulations, which preferably comprise a phosphate buffer with saline or a chosen salt, as well as preserved solutions and formulations containing a preservative as well as multi-use preserved formulations suitable for pharmaceutical or veterinary use, comprising at least one anti-IL-12/23p40 (or anti-IL-23) antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the method of the invention uses an article of manufacture, comprising packaging material and at least one vial comprising a solution of at least one anti-IL-12/23p40 (or anti-IL-23) antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further uses an article of manufacture, comprising packaging material, a first vial comprising lyophilized anti-IL-12/23p40 (or anti-IL-23) antibody, and a second vial comprising an aqueous diluent of prescribed buffer or preservative, wherein said packaging material comprises a label that instructs a patient to reconstitute the anti-IL-12/23p40 (or anti-IL-23) antibody in the aqueous diluent to form a solution that can be held over a period of twenty-four hours or greater.

The anti-IL-12/23p40 (or anti-IL-23) antibody used in accordance with the present invention can be produced by recombinant means, including from mammalian cell or transgenic preparations, or can be purified from other biological sources, as described herein or as known in the art.

The range of the anti-IL-12/23p40 (or anti-IL-23) antibody includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an antimicrobial effect. Such concentrations are dependent on the preservative selected and are readily determined by the skilled artisan.

Other excipients, e.g., isotonicity agents, buffers, antioxidants, and preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably, the formulations of the present invention have a pH between about 6.8 and about 7.8. Preferred buffers include phosphate buffers, most preferably, sodium phosphate, particularly, phosphate buffered saline (PB S).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants, such as polysorbate 20 or 80 or poloxamer 184 or 188, Pluronic® polyls, other block co-polymers, and chelators, such as EDTA and EGTA, can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations can be prepared by a process which comprises mixing at least one anti-IL-12/23p40 (or anti-IL-23) antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-IL-12/23p40 (or anti-IL-23) antibody and preservative in an aqueous diluent is carried out using conventional dissolution and mixing procedures. To prepare a suitable formulation, for example, a measured amount of at least one anti-IL-12/23p40 (or anti-IL-23) antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The formulations can be provided to patients as clear solutions or as dual vials comprising a vial of lyophilized anti-IL-12/23p40 (or anti-IL-23) antibody that is reconstituted with a second vial containing water, a preservative and/or excipients, preferably, a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present articles of manufacture are useful for administration over a period ranging from immediate to twenty-four hours or greater. Accordingly, the presently claimed articles of manufacture offer significant advantages to the patient. Formulations of the invention can optionally be safely stored at temperatures of from about 2° C. to about 40° C. and retain the biologically activity of the protein for extended periods of time, thus allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of anti-IL-12/23p40 (or anti-IL-23) antibody can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and, optionally, a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one anti-IL-12/23p40 (or anti-IL-23) antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one anti-IL-12/23p40 (or anti-IL-23) antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising single vial systems include pen-injector devices for delivery of a solution, such as BD Pens, BD Autojector®, Humaject®, NovoPen®, B-D®Pen, AutoPen®, and OptiPen®, GenotropinPen®, Genotronorm Pen®, Humatro Pen®, Reco-Pen®, Roferon Pen®, Biojector®, Iject®, J-tip Needle-Free Injector®, Intraject®, Medi-Ject®, Smartject® e.g., as made or developed by Becton Dickensen (Franklin Lakes, N.J., www.bectondickenson.com), Disetronic (Burgdorf, Switzerland, www.disetronic.com; Bioject, Portland, Oreg. (www.bioject.com); National Medical Products, Weston Medical (Peterborough, UK, www.weston-medical.com), Medi-Ject Corp (Minneapolis, Minn., www.mediject.com), and similarly suitable devices. Recognized devices comprising a dual vial system include those pen-injector systems for reconstituting a lyophilized drug in a cartridge for delivery of the reconstituted solution, such as the HumatroPen®. Examples of other devices suitable include pre-filled syringes, auto-injectors, needle free injectors, and needle free IV infusion sets.

The products may include packaging material. The packaging material provides, in addition to the information required by the regulatory agencies, the conditions under which the product can be used. The packaging material of the present invention provides instructions to the patient, as applicable, to reconstitute the at least one anti-IL-12/23p40 (or anti-IL-23) antibody in the aqueous diluent to form a solution and to use the solution over a period of 2-24 hours or greater for the two vial, wet/dry, product. For the single vial, solution product, pre-filled syringe or auto-injector, the label indicates that such solution can be used over a period of 2-24 hours or greater. The products are useful for human pharmaceutical product use.

The formulations used in the method of the present invention can be prepared by a process that comprises mixing an anti-IL-12/23p40 (or anti-IL-23) antibody and a selected buffer, preferably, a phosphate buffer containing saline or a chosen salt. Mixing the anti-IL-12/23p40 (or anti-IL-23) antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The method of the invention provides pharmaceutical compositions comprising various formulations useful and acceptable for administration to a human or animal patient. Such pharmaceutical compositions are prepared using water at "standard state" as the diluent and routine methods well known to those of ordinary skill in the art. For example, buffering components such as histidine and histidine monohydrochloride hydrate, may be provided first followed by the addition of an appropriate, non-final volume of water diluent, sucrose and polysorbate 80 at "standard state." Isolated antibody may then be added. Last, the volume of the pharmaceutical composition is adjusted to the desired final volume under "standard state" conditions using water as the diluent. Those skilled in the art will recognize a number of other methods suitable for the preparation of the pharmaceutical compositions.

The pharmaceutical compositions may be aqueous solutions or suspensions comprising the indicated mass of each constituent per unit of water volume or having an indicated pH at "standard state." As used herein, the term "standard state" means a temperature of 25° C.+/−2° C. and a pressure of 1 atmosphere. The term "standard state" is not used in the art to refer to a single art recognized set of temperatures or pressure, but is instead a reference state that specifies temperatures and pressure to be used to describe a solution or suspension with a particular composition under the reference "standard state" conditions. This is because the volume of a solution is, in part, a function of temperature and pressure. Those skilled in the art will recognize that pharmaceutical compositions equivalent to those disclosed here can be produced at other temperatures and pressures. Whether such pharmaceutical compositions are equivalent to those disclosed here should be determined under the "standard state" conditions defined above (e.g. 25° C.+/−2° C. and a pressure of 1 atmosphere).

Importantly, such pharmaceutical compositions may contain component masses "about" a certain value (e.g. "about 0.53 mg L-histidine") per unit volume of the pharmaceutical composition or have pH values about a certain value. A component mass present in a pharmaceutical composition or pH value is "about" a given numerical value if the isolated antibody present in the pharmaceutical composition is able to bind a peptide chain comprising residues 1-88 of SEQ ID NO: 9 while the isolated antibody is present in the pharmaceutical composition or after the isolated antibody has been removed from the pharmaceutical composition (e.g., by dilution). Stated differently, a value, such as a component mass value or pH value, is "about" a given numerical value when the binding activity of the isolated antibody is maintained and detectable after placing the isolated antibody in the pharmaceutical composition.

Competition binding analysis is performed to determine if the IL-12/23p40 (or anti-IL-23) mAbs bind to similar or different epitopes and/or compete with each other. Abs are individually coated on ELISA plates. Competing mAbs are added, followed by the addition of biotinylated hrIL-12/23p40. For positive control, the same mAb for coating may be used as the competing mAb ("self-competition"). IL-12/23p40 binding is detected using streptavidin. These results demonstrate whether the mAbs recognize similar or partially overlapping epitopes on IL-12/23p40.

One aspect of the method of the invention administers to a patient a pharmaceutical composition comprising an isolated antibody that binds a peptide chain comprising residues 1-88 of SEQ ID NO: 9; from about 0.27 to about 0.80 mg L-histidine per ml of the pharmaceutical composition; from about 0.69 to about 2.1 mg L-histidine monohydrochloride monohydrate per ml of the pharmaceutical composition; from about 0.02 to about 0.06 mg polysorbate 80 per ml of the pharmaceutical composition; and from about 65 to about 87 mg of sucrose per ml of the pharmaceutical composition; wherein the diluent is water at standard state.

Another aspect of the invention comprises administering a pharmaceutical composition comprising an isolated antibody having (i) the heavy chain CDR amino acid sequences of SEQ ID NO: 1, SEQ ID NO: 2, and SEQ ID NO: 3; and (ii) the light chain CDR amino acid sequences of SEQ ID NO: 4, SEQ ID NO: 5, and SEQ ID NO: 6 wherein the isolated antibody binds a peptide chain comprising residues 1-88 of SEQ ID NO: 9; from about 0.27 to about 0.80 mg L-histidine per ml of the pharmaceutical composition; from about 0.69 to about 2.1 mg L-histidine monohydrochloride monohydrate per ml of the pharmaceutical composition; from about 0.02 to about 0.06 mg polysorbate 80 per ml of the pharmaceutical composition; and from about 65 to about 87 mg of sucrose per ml of the pharmaceutical composition; wherein the diluent is water at standard state.

Another aspect of the method of the invention is administering to a patient a pharmaceutical composition comprising an isolated anti-IL-12/23p40 antibody having the heavy chain amino acid sequence of SEQ ID NO: 7 and the light chain amino acid sequence of SEQ ID NO: 8 wherein the isolated antibody binds a peptide chain comprising residues 1-88 of SEQ ID NO: 9; from about 0.27 to about 0.80 mg L-histidine per ml of the pharmaceutical composition; from about 0.69 to about 2.1 mg L-histidine monohydrochloride monohydrate per ml of the pharmaceutical composition; from about 0.02 to about 0.06 mg polysorbate 80 per ml of the pharmaceutical composition; and from about 65 to about 87 mg of sucrose per ml of the pharmaceutical composition; wherein the diluent is water at standard state.

In one embodiment of the pharmaceutical compositions, the isolated antibody concentration is from about 77 to about 104 mg per ml of the pharmaceutical composition. In another embodiment of the pharmaceutical compositions the pH is from about 5.5 to about 6.5.

Another aspect of the method of the invention administers to a patient a pharmaceutical composition comprising an isolated anti-IL-12/23p40 antibody having (i) the heavy chain CDR amino acid sequences of SEQ ID NO: 1, SEQ ID NO: 2, and SEQ ID NO: 3; and (ii) the light chain CDR amino acid sequences of SEQ ID NO: 4, SEQ ID NO: 5, and SEQ ID NO: 6 wherein the isolated antibody binds a peptide chain comprising residues 1-88 of SEQ ID NO: 9; about 0.53 mg L-histidine per ml of the pharmaceutical composition; about 1.37 mg L-histidine monohydrochloride monohydrate per ml of the pharmaceutical composition; about 0.04 mg polysorbate 80 per ml of the pharmaceutical composition; and about 76 mg of sucrose per ml of the pharmaceutical composition; wherein the diluent is water at standard state.

A further aspect of the method of the invention administers to a patient a pharmaceutical composition comprising an isolated anti-IL-12/23p40 antibody having the heavy chain amino acid sequence of SEQ ID NO: 7 and the light chain amino acid sequence of SEQ ID NO: 8 wherein the isolated antibody binds a peptide chain comprising residues 1-88 of SEQ ID NO: 9; about 0.53 mg L-histidine per ml of the pharmaceutical composition; about 1.37 mg L-histidine monohydrochloride monohydrate per ml of the pharmaceutical composition; about 0.04 mg polysorbate 80 per ml of the pharmaceutical composition; and about 76 mg of sucrose per ml of the pharmaceutical composition; wherein the diluent is water at standard state.

In one embodiment, the isolated antibody concentration is about 90 mg per ml of the pharmaceutical composition. In another embodiment of these pharmaceutical compositions the pH is about 6.0. Another aspect of the invention is a method using a pharmaceutical composition comprising an antibody that competes for binding with an anti-IL-12/23p40 antibody as recited herein, e.g., binds a peptide chain comprising residues 1-88 of SEQ ID NO: 9; from about 0.27 to about 0.80 mg L-histidine per ml of the pharmaceutical composition; from about 0.69 to about 2.1 mg L-histidine monohydrochloride monohydrate per ml of the pharmaceutical composition; from about 0.02 to about 0.06 mg polysorbate 80 per ml of the pharmaceutical composition; and from about 65 to about 87 mg of sucrose per ml of the pharmaceutical composition; wherein the diluent is water at standard state.

The stable or preserved formulations can be provided to patients as clear solutions or as dual vials comprising a vial of lyophilized at least one anti-IL-12/23p40 antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

Other formulations or methods of stabilizing the anti-IL-12/23p40 (or anti-IL-23) antibody may result in other than a clear solution of lyophilized powder comprising the antibody. Among non-clear solutions are formulations comprising particulate suspensions, said particulates being a composition containing the anti-IL-12/23p40 (or anti-IL-23) antibody in a structure of variable dimension and known variously as a microsphere, microparticle, nanoparticle, nanosphere, or liposome. Such relatively homogenous, essentially spherical, particulate formulations containing an active agent can be formed by contacting an aqueous phase containing the active agent and a polymer and a nonaqueous phase followed by evaporation of the nonaqueous phase to cause the coalescence of particles from the aqueous phase as taught in U.S. Pat. No. 4,589,330. Porous microparticles can be prepared using a first phase containing active agent and a polymer dispersed in a continuous solvent and removing said solvent from the suspension by freeze-drying or dilution-extraction-precipitation as taught in U.S. Pat. No. 4,818,542.

Preferred polymers for such preparations are natural or synthetic copolymers or polymers selected from the group consisting of gelatin agar, starch, arabinogalactan, albumin, collagen, polyglycolic acid, polylactic aced, glycolide-L(−) lactide poly(episilon-caprolactone, poly(epsilon-caprolactone-CO-lactic acid), poly(epsilon-caprolactone-CO-glycolic acid), poly(B-hydroxy butyric acid), polyethylene oxide, polyethylene, poly(alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly preferred polymers are polyesters, such as polyglycolic acid, polylactic aced, glycolide-L(−) lactide poly(episilon-caprolactone, poly(epsilon-caprolactone-CO-lactic acid), and poly(epsilon-caprolactone-CO-glycolic acid. Solvents useful for dissolving the polymer and/or the active include: water, hexafluoroisopropanol, methylenechloride, tetrahydrofuran, hexane, benzene, or hexafluoroacetone sesquihydrate. The process of dispersing the active containing phase with a second phase may include pressure forcing said first phase through an orifice in a nozzle to affect droplet formation.

Dry powder formulations may result from processes other than lyophilization, such as by spray drying or solvent extraction by evaporation or by precipitation of a crystalline composition followed by one or more steps to remove aqueous or nonaqueous solvent. Preparation of a spray-dried antibody preparation is taught in U.S. Pat. No. 6,019,968. The antibody-based dry powder compositions may be produced by spray drying solutions or slurries of the antibody and, optionally, excipients, in a solvent under conditions to provide a respirable dry powder. Solvents may include polar compounds, such as water and ethanol, which may be readily dried. Antibody stability may be enhanced by performing the spray drying procedures in the absence of oxygen, such as under a nitrogen blanket or by using nitrogen as the drying gas. Another relatively dry formulation is a dispersion of a plurality of perforated microstructures dispersed in a suspension medium that typically comprises a hydrofluoroalkane propellant as taught in WO 9916419. The stabilized dispersions may be administered to the lung of a patient using a metered dose inhaler. Equipment useful in the commercial manufacture of spray dried medicaments are manufactured by Buchi Ltd. or Niro Corp.

An anti-IL-12/23p40 (or anti-IL-23) antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications

The present invention also provides a method for modulating or treating at least one IL-12/23 related disease, in a cell, tissue, organ, animal, or patient, as known in the art or as described herein, using at least one IL-12/23p40 (or anti-IL-23) antibody of the present invention, e.g., administering or contacting the cell, tissue, organ, animal, or patient with a therapeutic effective amount of IL-12/23p40 (or anti-IL-23) antibody. The present invention also provides a method for modulating or treating at least one IL-12/23 related disease, in a cell, tissue, organ, animal, or patient including, but not limited to, at least one of obesity, an immune related disease, a cardiovascular disease, an infectious disease, a malignant disease or a neurologic disease.

The present invention also provides a method for modulating or treating at least one IL-12/23 related immune related disease, in a cell, tissue, organ, animal, or patient including, but not limited to, at least one of psoriasis, psoriatic arthritis, rheumatoid arthritis, juvenile rheumatoid arthritis, systemic onset juvenile rheumatoid arthritis, ankylosing spondylitis, gastric ulcer, seronegative arthropathies, osteoarthritis, osteolysis, aseptic loosening of orthopedic implants, inflammatory bowel disease, ulcerative colitis, systemic lupus erythematosus, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitivity reactions, allergic rhinitis, hay fever, perennial rhinitis, conjunctivitis, endometriosis, asthma, urticaria, systemic anaphalaxis, dermatitis, pernicious anemia, hemolytic disease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynaud's disease, type B insulin-resistant diabetes, asthma, myasthenia gravis, antibody-meditated cytotoxicity, type III hypersensitivity reactions, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited to, asthenia, anemia, cachexia, and the like), chronic salicylate intoxication, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference. Such a method can optionally comprise administering an effective amount of a composition or pharmaceutical composition comprising at least one TNF antibody or specified portion or variant to a cell, tissue, organ, animal or patient in need of such modulation, treatment or therapy. See, e.g., the Merck Manual, 16$^{th}$ Edition, Merck & Company, Rahway, N.J. (1992).

The present invention also provides a method for modulating or treating psoriasis, psoriatic arthritis, Crohn's disease, other inflammatory bowel diseases, lupus, sarcoidosis, AS or nrAxSpA, among the other diseases listed above as IL-12/23 related, in a cell, tissue, organ, animal, or patient including, but not limited to, at least one of immune related disease, cardiovascular disease, infectious, malignant and/or neurologic disease. Such a method can optionally comprise administering an effective amount of at least one composition or pharmaceutical composition comprising an anti-IL- 12/23p40 (or anti-IL-23) antibody to a cell, tissue, organ, animal or patient in need of such modulation, treatment or therapy.

Any method of the present invention can comprise administering an effective amount of a composition or pharmaceutical composition comprising an anti-IL-12/23p40 (or anti-IL-23) antibody to a cell, tissue, organ, animal or patient in need of such modulation, treatment or therapy. Such a method can optionally further comprise co-administration or combination therapy for treating such diseases or disorders, wherein the administering of said at least one anti-IL-12/23p40 (or anti-IL-23) antibody, specified portion or variant thereof, further comprises administering, before concurrently, and/or after, at least one selected from at least one TNF antagonist (e.g., but not limited to, a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, eternacept (Enbrel™), adalimumab (Humira™), CDP-571, CDP-870, afelimomab, lenercept, and the like), an antirheumatic (e.g., methotrexate, auranofin, aurothioglucose, azathioprine, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, C A (2000); Nursing 2001 Handbook of Drugs, $21^{st}$ edition, Springhouse Corp., Springhouse, P A, 2001; Health Professional's Drug Guide 2001, ed., Shannon, Wilson, Stang, Prentice-Hall, Inc, Upper Saddle River, N.J., each of which references are entirely incorporated herein by reference.

Therapeutic Treatments

Typically, treatment of pathologic conditions is affected by administering an effective amount or dosage of an anti-IL-12/23p40 (or anti-IL-23) antibody composition that total, on average, a range from at least about 0.01 to 500 milligrams of an anti-IL-12/23p40 (or anti-IL-23) antibody per kilogram of patient per dose, and, preferably, from at least about 0.1 to 100 milligrams antibody/kilogram of patient per single or multiple administration, depending upon the specific activity of the active agent contained in the composition. Alternatively, the effective serum concentration can comprise 0.1-5000 µg/ml serum concentration per single or multiple administration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5., 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and, preferably, 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or, alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or, alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.001 milligram to about 500 milligrams of active ingredient per unit or container. In these pharmaceutical compositions the active ingredient will ordinarily be present in an amount of about 0.5-99.999% by weight based on the total weight of the composition.

For parenteral administration, the antibody can be formulated as a solution, suspension, emulsion, particle, powder, or lyophilized powder in association, or separately provided, with a pharmaceutically acceptable parenteral vehicle. Examples of such vehicles are water, saline, Ringer's solution, dextrose solution, and 1-10% human serum albumin. Liposomes and nonaqueous vehicles, such as fixed oils, can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Alternative Administration

Many known and developed modes can be used according to the present invention for administering pharmaceutically effective amounts of an anti-IL-12/23p40 (or anti-IL-23) antibody. While pulmonary administration is used in the following description, other modes of administration can be used according to the present invention with suitable results. IL-12/23p40 (or anti-IL-23) antibodies of the present invention can be delivered in a carrier, as a solution, emulsion, colloid, or suspension, or as a dry powder, using any of a variety of devices and methods suitable for administration by inhalation or other modes described here within or known in the art.

Parenteral Formulations and Administration

Formulations for parenteral administration can contain as common excipients sterile water or saline, polyalkylene glycols, such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent, such as aqueous solution, a sterile injectable solution or suspension in a solvent. As the usable vehicle or solvent, water, Ringer's solution, isotonic saline, etc. are allowed; as an ordinary solvent or suspending solvent, sterile involatile oil can be used. For these purposes, any kind of involatile oil and fatty acid can be used, including natural or synthetic or semisynthetic fatty oils or fatty acids; natural or synthetic or semi-synthetic mono- or di- or tri-glycerides. Parental administration is known in the art and includes, but is not limited to, conventional means of injections, a gas pressured needleless injection device as described in U.S. Pat. No. 5,851,198, and a laser perforator device as described in U.S. Pat. No. 5,839,446 entirely incorporated herein by reference.

Alternative Delivery

The invention further relates to the administration of an anti-IL-12/23p40 (or anti-IL-23) antibody by parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal means. An anti-IL-12/23p40 (or anti-IL-23) antibody composition can be prepared for use for parenteral (subcutaneous, intramuscular or intravenous) or any other administration particularly in the form of liquid solutions or suspensions; for use in vaginal or rectal administration particularly in semisolid forms, such as, but not limited to, creams and suppositories; for buccal, or sublingual administration, such as, but not limited to, in the form of tablets or capsules; or intranasally, such as, but not limited to, the form of powders, nasal drops or aerosols or certain agents; or transdermally, such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement;" Hsieh, D. S., Eds., pp. 59-90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways, such as electroporation, or to increase the mobility of charged drugs through the skin, such as iontophoresis, or application of ultrasound, such as sonophoresis (U.S. Pat. Nos. 4,309,989 and 4,767,402) (the above publications and patents being entirely incorporated herein by reference).

Having generally described the invention, the same will be more readily understood by reference to the following Examples, which are provided by way of illustration and are not intended as limiting. Further details of the invention are illustrated by the following non-limiting Examples. The disclosures of all citations in the specification are expressly incorporated herein by reference.

Example 1: Cloning and Expression of IL-12 Antibody in Mammalian Cells

A typical mammalian expression vector contains at least one promoter element, which mediates the initiation of transcription of mRNA, the antibody coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors, such as pIRES1neo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109). Mammalian host cells that could be used include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells. Alternatively, the gene can be expressed in stable cell lines that contain the gene integrated into a chromosome. The co-transfection with a selectable marker, such as dhfr, gpt, neomycin, or hygromycin, allows the identification and isolation of the transfected cells.

The transfected gene can also be amplified to express large amounts of the encoded antibody. The DHFR (dihydrofolate reductase) marker is useful to develop cell lines that carry several hundred or even several thousand copies of the gene of interest. Another useful selection marker is the enzyme glutamine synthase (GS) (Murphy, et al., Biochem. J. 227:277-279 (1991); Bebbington, et al., Bio/Technology 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of antibodies.

The expression vectors pC1 and pC4 contain the strong promoter (LTR) of the Rous Sarcoma Virus (Cullen, et al., Molec. Cell. Biol. 5:438-447 (1985)) plus a fragment of the CMV-enhancer (Boshart, et al., Cell 41:521-530 (1985)). Multiple cloning sites, e.g., with the restriction enzyme cleavage sites BamHI, XbaI and Asp718, facilitate the cloning of the gene of interest. The vectors contain in addition to the 3' intron, the polyadenylation and termination signal of the rat preproinsulin gene.

Cloning and Expression in CHO Cells.

The vector pC4 is used for the expression of IL-12/23p40 antibody. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (e.g., alpha minus MEM, Life Technologies, Gaithersburg, Md.) supplemented with the chemotherapeutic agent methotrexate. The amplification of the DHFR genes in cells resistant to methotrexate (MTX) has been well documented (see, e.g., F. W. Alt, et al., J. Biol. Chem. 253:1357-1370 (1978); J. L. Hamlin and C. Ma, Biochem. et Biophys. Acta 1097:107-143 (1990); and M. J. Page and M. A. Sydenham, Biotechnology 9:64-68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach can be used to develop cell lines carrying more than 1,000 copies of the amplified gene(s). Subsequently, when the methotrexate is withdrawn, cell lines are obtained that contain the amplified gene integrated into one or more chromosome(s) of the host cell.

High efficiency promoters other than the strong promoter of the long terminal repeat (LTR) of the Rous Sarcoma Virus can also be used for the expression, e.g., the human b-actin promoter, the SV40 early or late promoters or the long terminal repeats from other retroviruses, e.g., HIV and HTLVI. Clontech's Tet-Off and Tet-On gene expression systems and similar systems can be used to express the IL-12 in a regulated way in mammalian cells (M. Gossen, and H. Bujard, Proc. Natl. Acad. Sci. USA 89: 5547-5551 (1992)). For the polyadenylation of the mRNA, other signals, e.g., from the human growth hormone or globin genes, can be used as well. Stable cell lines carrying a gene of interest integrated into the chromosomes can also be selected upon co-transfection with a selectable marker, such as gpt, G418 or hygromycin. It is advantageous to use more than one selectable marker in the beginning, e.g., G418 plus methotrexate. The plasmid pC4 is digested with restriction enzymes and then dephosphorylated using calf intestinal phosphatase by procedures known in the art. The vector is then isolated from a 1% agarose gel.

The DNA sequence encoding the complete IL-12/23p40 antibody is used, corresponding to HC and LC CDR regions of an IL-12/23p40 antibody of the present invention, respectively, according to known method steps. Isolated nucleic acid encoding a suitable human constant region (i.e., HC and LC regions) is also used in this construct.

The isolated variable and constant region encoding DNA and the dephosphorylated vector are then ligated with T4 DNA ligase. E. coli HB101 or XL-1 Blue cells are then transformed and bacteria are identified that contain the fragment inserted into plasmid pC4 using, for instance, restriction enzyme analysis.

Chinese hamster ovary (CHO) cells lacking an active DHFR gene are used for transfection. 5 micrograms of the expression plasmid pC4 is cotransfected with 0.5 micrograms of the plasmid pSV2-neo using lipofectin. The plasmid pSV2neo contains a dominant selectable marker, the neo gene from Tn5 encoding an enzyme that confers resistance to a group of antibiotics including G418. The cells are seeded in alpha minus MEM supplemented with 1 microgram/ml G418. After 2 days, the cells are trypsinized and seeded in hybridoma cloning plates (Greiner, Germany) in alpha minus MEM supplemented with 10, 25, or 50 ng/ml of methotrexate plus 1 microgram/ml G418. After about 10-14 days, single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 mM, 2 mM, 5 mM, 10 mM, 20 mM). The same procedure is repeated until clones are obtained that grow at a concentration of 100-200 mM. Expression of the desired gene product is analyzed, for instance, by SDS-PAGE and Western blot or by reverse phase HPLC analysis.

Example 2: Comparison of the Therapeutic Efficacy of Anti-IL-12p35 and Anti-IL-12/23p40 Antibodies in Murine Experimental Autoimmune Encephalomyelitis (EAE)

Summary

This set of studies was performed to investigate the therapeutic efficacy of IL-12 or IL-12/IL-23 specific neutralization in a mouse model for multiple sclerosis, experimental autoimmune encephalomyelitis (EAE). Neutralizing rat anti-mouse monoclonal antibodies (mAbs) specific for the p35 subunit of IL-12 or the p40 subunit that is shared between IL-12 and IL-23 were administered either prior to disease induction, prior to disease onset, or after disease was ongoing. In all cases, only anti-p40 demonstrated therapeutic potential. These data suggest that IL-23 is the predominant contributor to disease pathogenesis in this autoimmune model.

Abbreviations
IL Interleukin
mAb Monoclonal antibody
EAE Experimental autoimmune encephalomyelitis
Th T helper cell
IFNγ Interferon gamma
cs Clinical score
MBP Myelin basic protein
PK Pharmacokinetics Introduction Biologically active IL-12 exists as a heterodimer comprised of 2 covalently linked subunits of 35 (p35) and 40 (p40) kilo Daltons. Several lines of evidence have demonstrated that IL-12 can induce robust Th1 immune responses that are characterized by production of IFN☐ and IL-2 from $CD4^+$ T cells. Inappropriate Th1 responses, and thus IL-12 expression, are believed to correlate with many immune-mediated diseases, such as multiple sclerosis, rheumatoid arthritis, inflammatory bowel disease, insulin-dependent diabetes mellitus, and uveitis. In animal models, IL-12 neutralization was shown to ameliorate immune-mediated disease. However, these studies neutralized IL-12 through its p40 subunit. The recent description of IL-23 (1), a heterodimeric cytokine that shares the p40 subunit, made it important to determine whether previous findings were due to IL-12 or IL-23 activity. Therefore, p35 and p40 specific neutralization were compared in a mouse model of autoimmunity, experimental autoimmune encephalomyelitis (EAE). Neutralizing antibodies specific for IL-12p35 had no effect on EAE progression. In contrast, neutralization of both IL-12 and IL-23 with an anti-p40 mAb suppressed clinical signs of EAE, whether antibody was administered before or after Th1 differentiation. This data suggests that the activity of anti-p40 treatment in EAE is based solely on neutralization of IL-23.

Methods and Materials

Mice

Female C3H/HEB/FEJ mice (Jackson Laboratories, Bar Harbor, Me.) were used in pharmacokinetic analyses. For EAE studies, female B10.PL (H-$2^a$) mice were purchased from the Jackson Laboratories, and were used between 6-8 weeks of age. All animals were maintained according to IACUC guidelines under approved protocols.

Antibodies

C17.8 (rat anti-mouse IL-12/IL-23p40, IgG2a), and C18.2 (rat anti mouse IL-12p35, IgG2a) hybridomas provided by Dr. Giorgio Trinchieri and the Wistar Institute (Philadelphia, Pa.). Ascites was generated at Harlan Bioproducts (Indianapolis, Ind.) and purified by protein G affinity.

Serum PK of Rat Anti-Mouse Antibodies

Female C3H/HEB/FEJ mice, approximately 20-25 grams, were individually weighed and treated with a single 5 mg/kg intraperitoneal dose of $^{125}$I labeled antibody (C17.8, C18.2), with a constant dose volume/mouse of 10 mL/kg. Retro-orbital bleeds were taken from anesthetized mice at 30 minutes, 6 and 24 hours, 4, 7, 11 and 18 days. Blood samples were allowed to stand at room temperature for at least 30 minutes, but no longer than 1 hour, and were then centrifuged at approximately 2,500-3,500 rpm for 10-15 minutes. Approximately 50 uL aliquots of each serum sample were counted for $^{125}$I using a LKB Compugamma 1282 counter (Wallac, Gaithersburg, Md.). 10 mL aliquots of the injectates were also counted. The average fraction of injected counts at each time point was calculated and multiplied by the total mg of antibody injected to determine the total mg remaining in the serum at each time point. Data is shown as the mean mg of mAb in the sera+/−s.d. with 5-10 animals in each group.

EAE Induction and Scoring

For EAE induction, female B10.PL mice were injected subcutaneously over four sites on the back with a total of 100 μl of CFA (containing 200 μg Mycobacterium tuberculosis Jamaica strain) combined with 200 μg guinea pig-MBP (Sigma). Mice also received 200 ng pertussis toxin (List Biological, Campbell, Calif.) i.p. in 0.2 ml PBS at the time of immunization and 48 hours later. Mice received i.p. injections of C17.8 (anti-IL-12p40) or C18.2 (anti-IL-12p35) monoclonal antibodies diluted to 100 mg/kg (C18.2) or 20 mg/kg (C17.8) in PBS, on indicated days. Control mice received PBS or Rat IgG (Biosource) at 20 mg/kg in PBS.

Animals that demonstrated clinical signs (cs) were scored as follows: limp tail or waddling gait with tail tonicity 1, waddling gait with limp tail (ataxia) 2, ataxia with partial limb paralysis 2.5, full paralysis of one limb 3, full paralysis of one limb with partial paralysis of second limb 3.5, full paralysis of two limbs 4, moribund 4.5, death 5. Animals that scored a 5 were not included in the mean daily cs analysis for the rest of the experiment. Daily cs are averaged for the group, and mean incidence, day of onset, highest acute cs, cumulative cs, cs/day, number of relapses and relapse severity±sem are described. Mean cumulative cs per group was calculated by averaging the sum of daily clinical scores for individual animals. Cs/day was calculated by dividing the cumulative cs by the number of days the animal remained in the study. To determine the mean day of onset, animals not developing EAE were not included in the analysis. To determine the mean highest cs, mice not developing EAE were assigned a value of "0" and included in the analysis. Relapses were defined by a full point drop in clinical score sustained for at least 2 observed days followed by a full point increase in clinical score sustained for at least 2 observed days.

Results and Discussion

Anti-p35 and Anti-p40 Antibodies have Identical Pharmacokinetics

To establish the clearance rates of anti-p40 and anti-p35 antibodies, normal mice were injected with a single 5 mg/kg dose of $^{125}$I labeled antibodies and circulating levels were measured for 11 days post antibody administration. Anti-p35 and anti-p40 had overlapping pharmacokinetics, demonstrating that clearance rates are identical in normal mice (2). The expected clearance rate of each mAb is approximately 7-10 days. Although this is a single dose PK study, these data support once weekly dosing for in vivo studies.

Only Anti-p40 Treatment Prior to EAE Induction is Protective

To determine the relative roles of IL-12 and IL-23 in immune-mediated diseases, we utilized a murine model for multiple sclerosis, relapsing experimental autoimmune encephalomyelitis (EAE). Upon EAE induction with myelin basic protein (MBP) in adjuvant, B10.PL mice typically exhibit an initial episode of paralysis (acute disease), then recover either partially or completely and progress through multiple relapses and/or chronic EAE. It has long been assumed that EAE is dependent upon IL-12 expression since IL-12 is believed to be a primary mediator of Th0 to Th1 differentiation. However, to distinguish the potential role of IL-23 in EAE induction, neutralizing concentrations of anti-p40 (IL-12 and IL-23) or anti-p35 (IL-12 only) antibodies were established one day prior to immunization for EAE (Day −1). Onset of disease can vary between animals; therefore, treatment was repeated 7 and 14 days later to ensure that anti-p35 and IL-p40 antibodies were present during Th1 differentiation. Several in vitro neutralization studies have demonstrated that the anti-40 mAb is 5 times more effective in neutralizing IL-12 than the anti-p35 mAb (data not shown). Therefore, the dose of anti-p35 mAb was adjusted to be 5 fold higher than anti-p40 in all EAE experiments. In two separate experiments, mice treated with Rat IgG isotype control antibody (20 mg/kg) or anti-p35 (100 mg/kg) did not demonstrate protection from disease. It is important to note that peripheral administration of a non-specific control antibody (Rat IgG) did not alter the clinical course of disease when compared to non-treated mice with EAE. In both studies, mice treated with anti-p40 mAb (20 mg/kg) exhibited nearly complete inhibition of EAE clinical signs. Remarkably, suppression of disease extended beyond the expected rate of antibody clearance through 70 days post EAE induction. In each experiment, only one animal treated with anti-p40 exhibited two consecutive days of EAE clinical signs, and each demonstrated a late onset and significantly lower acute clinical scores, cumulative clinical scores, and no relapses in disease (Table 1). These results demonstrate that neutralization of IL-12 and IL-23 through the shared p40 subunit provided nearly complete protection from EAE. In contrast, specific neutralization of IL-12 only via anti-p35 was ineffective. These data strongly suggest that EAE is not mediated by IL-12.

Only Anti-p40 Treatment Just Prior to Disease Onset is Protective

Although prophylactic treatment completely protected mice from EAE, it remained to be determined if IL-12 specific neutralization would be protective once the Th1 population was established in vivo. Therefore, in a separate set of experiments, mice were treated with either a control antibody (Rat IgG), anti-p35, or anti-p40 monoclonal antibodies ten days after EAE induction, but prior to disease onset. Since typical immune responses occur within 7 days, this time point should reflect the effects of anti-IL-12 or anti-IL-23 mAbs on differentiated Th1 cells. EAE onset can vary between animals, therefore treatment was repeated 7 and 14 days later to ensure that anti-p35 and anti-p40 antibodies were present during the onset of disease. In two separate experiments, mice treated with isotype control antibody (20 mg/kg) or anti-p35 (100 mg/kg) were not protected from disease, when compared to untreated EAE mice. However, mice treated with anti-p40 mAb (20 mg/kg) were significantly protected from EAE. As shown in the previously described studies, disease suppression was observed well beyond the time required for clearance of peripherally administered antibody through day 70 post EAE induction. Considering that antibody was not administered until after Th1 differentiation (day 10), it was not surprising that disease incidence, day of onset, and the highest clinical score during acute EAE were not different in any group (Table 2). However, in both experiments, mice receiving anti-p40 exhibited significantly lower cumulative clinical scores, clinical scores per day, and relapse severity.

Only Anti-p40 Treatment During Established EAE is Protective

The most difficult, but clinically relevant, hurdle for any therapy is to suppress established disease. Therefore another set of experiments was performed in which mice were immunized for EAE, then divided into treatment groups once disease was ongoing. Approximately 30 days post EAE induction, mice had progressed through the acute phase of disease. At this time, animals were divided into groups with comparable cumulative and daily clinical scores. Treatment was repeated 7 and 14 days later to ensure that antibodies were available in neutralizing concentrations during the transition from acute to chronic or remitting-relapsing disease. Only anti-p40 treatment (20 mg/kg) ameliorated disease when compared to either isotype control antibody (20 mg/kg) or anti-p35 (100 mg/kg) treated animals. Disease suppression was observed through day 80 post EAE induction. In both experiments, analysis from the first day of treatment through day 80 demonstrated that mice receiving anti-p40 exhibited lower cumulative clinical scores, clinical scores per day, and the least highest clinical score post treatment. These data suggest that not only is IL-23 likely to mediate Th1 differentiation (Table 1) and EAE induction (Table 2), but IL-23 also contributes to the effector phase of chronic immune-mediated (e.g., autoimmune) responses (Table 3). Therefore, anti-p40 treatment can offer therapy at any time in the progression of immune-mediated diseases.

Conclusions

The understanding of the role of IL-12 in immune function has been based on studies of the p40 subunit of IL-12. Therefore, a side-by-side comparison of neutralization of the IL-12 specific p35 subunit versus the p40 subunit shared between IL-12 and IL-23 was conducted in an animal model of autoimmune disease. Neutralization via anti-p40 significantly inhibited EAE when mAb was administered at any time point. However, IL-12 specific neutralization was completely ineffective. Therefore, our data shows that IL-12 does not contribute to this autoimmune model and that IL-23 is expected be the more prominent mediator of autoimmune T cell responses.

Example 3: p40 Neutralizing Epitope

Summary

The epitope for a neutralizing antibody (IL-12/23p40 mAb) against human p40 subunit of IL-12 and IL-23 was determined based on the crystal structure of the Fab/IL-12 complex. The epitope is located on the D1 domain (residues 1-88) of the p40 subunit of human IL-12. This region is distant from the p40/p35 interface and is expected to be also available on the p40 subunit of IL-23. The residues involved in antigen-antibody binding are discontinuous (Table 4) and comprise a unique conformational epitope. Antibodies against this epitope or portions of it and neighboring regions will lead to blockage of IL-12 and IL-23 functions mediated through this part of p40 subunit.

Introduction

A fully human monoclonal antibody (p40 mAb) directed against human IL-12/23p40 has been shown to be a potent neutralizer of IL-12 and IL-23 function. It has been shown that the p40 mAb binds to the p40 subunit and blocks the binding of both cytokines to their receptors. Because the p40 subunit is shared between IL-12 and IL-23, the detailed interactions between IL-12 and the p40 mAb define an important common neutralizing epitope, which may in turn shed some light on the cytokine-receptor interactions.

Epitope Determination Based on p40 Fab/IL-12 Crystal Structure

The IL-12/IL-23p40 mAb was produced from a mammalian cell line in culture and purified by protein A column. The IL-12/IL-23p40 mAb (70 mg) was digested with papain (0.25 units of papain per milligram of IgG) in activation buffer (0.03M sodium phosphate, 0.15M NaCl, 0.01M EDTA, 0.0072M L-cysteine, pH 7.0) at 37° C. for 2 hours. Digestion was monitored by Surface-Enhanced Laser desorption ionization (SELDI) mass spectrometry. Iodoacetamide (0.5M) was used to stop the digestion. Fc was removed by immobilized protein G. The p40 Fab was further purified by gel filtration on a Superdex 200 16/60 column. A total of 44 mg purified p40 Fab was obtained and its purity analyzed by SDS-PAGE.

Recombinant human IL-12 was produced in culture from a stably transfected cell line over-expressing the p40 and p35 subunits and purified with a p40 mAb affinity column. The protein fractions were collected and dialyzed into 10 mM Tris, 100 mM NaCl, pH 7.4 and concentrated to 2.5 mg/ml. IL-12 was deglycosylated by incubating with several combinations of deglycosylation enzymes (PNGase F, Sialadase, Endo-O-glycosydase, α-, β-galactosidase, α-mannosidase, fucosidase [about 5mU-10U/100 ug protein]) for 3 days at 37° C. under argon.

Deglycosylated IL-12 was mixed with an excess of the p40 Fab. The IL-12/p40 Fab complex was purified by size exclusion chromatography in 10 mM Tris, 50 mM NaCl, pH 7.4. The isolated complex was concentrated to approximately 4 mg/ml. The IL-12/p40 Fab complex was crystallized using the sitting drop vapor diffusion method by combining the above protein complex solution in 1:1 volume ratio with a reservoir solution of 50 mM Tris, pH 7.0, 16% PEG 3350. Cubic, pyramidal or rod shaped crystals of typically 50-150 μm in size appear within two weeks at 16° C.

The crystals were harvested, and soaked in the mother liquor plus 30% ethylene glycol and flash frozen in liquid nitrogen for X-ray data collection. The best data set was collected (360 degrees, 0.5 degree/frame, 10 second exposure per frame) to a diffraction limit of 2.8 Å at Advanced Photon Source (APS), Argonne National Laboratory, (Axas-ComCat). The diffraction data were processed with Denzo and ScalePack. (Otwinowski & Minor, Methods Enzymol. 276: 307-326) The space group for this crystal form is $P2_12_12_1$ with cell dimensions of a=116.8 Å, b=55.77 Å, c=182.96 Å, and a=(3=y=90°. There are 27,141 independent reflections and the data was ~90% complete at 3.0 Å (I/sigma=5.2, $R_{sym}$=9%.).

The crystal structure was solved by molecular replacement as implemented in CNX (Accelrys, CA). The search models were the published IL-12 structure (PDB code 1F45) for IL-12 and a homology model for p40 based upon a Fab crystal structure (PDB code 1VGE). The molecular models for IL-12 and the p40 Fab were visually inspected and manually adjusted using XtalView. The structure refinement was carried out with the CNX. The molecular models were validated with InsightII (Accelrys, CA). The molecular structure of the bound complex of IL-12/p40 Fab is shown in FIG. 1 in a ribbon representation.

Figure 2:
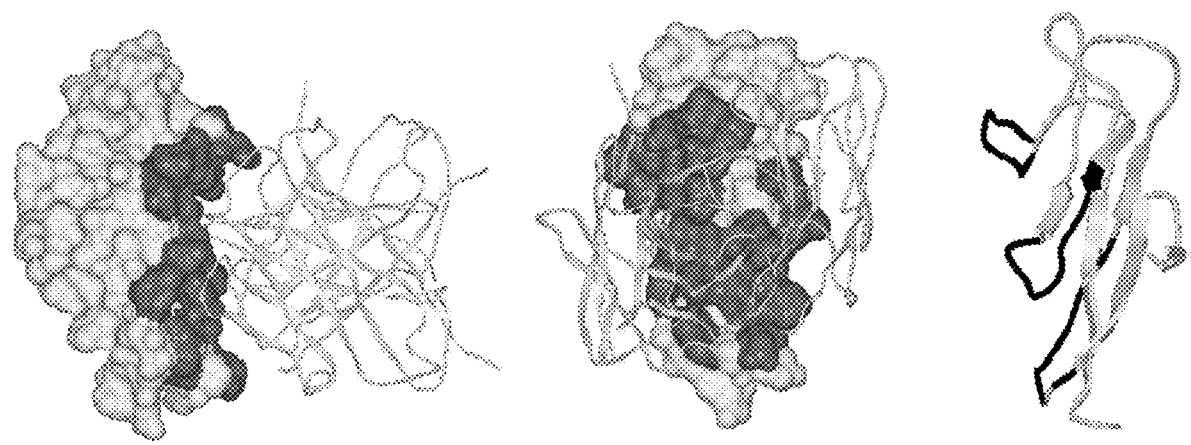
FIG. 2 shows the p40 mAb binding site (epitope) represented on the molecular surface in surface and ribbons representations. The D1 domain and Fv are isolated out of the complex structure for clarity. For the D1 domain of p40, the molecular surface is shown. The Fv part of the Fab is shown in ribbons. Left panel: view down the antibody binding site, i.e., the epitope. Middle panel: view ~90° from view in left panel. Right panel: Ribbon representation of the residues of the epitope.

The p40 mAb binding site (p40 epitope) on the molecular surface in surface and ribbons representations is shown in FIG. 2. The binding epitope residues are defined as any surface exposed p40 residues (relative solvent accessibility of 0.1 or greater) with any atoms within 4 Å of any atoms of the antibody, according to a generally accepted convention. The surface accessibilities were calculated by ICM (Molsoft, CA) using the default parameters. Residues comprising the p40 mAb binding epitope on IL-12 p40 are listed in Table 4, along with their surface exposed areas (sf) and relative accessibilities (sf ratio). The definition of exposed surface area of an amino acid residue within the context of protein has been well accepted in the field. In particular, a water molecule with a radius of 1.4 A is rolled along the surface of a protein and the amount of area obtained by this calculation for a specific residue is assigned to the expoed surface area of that residue. The total surface area for an amino acid in fully extended conformation is also available. The surface accessibility (sf ratio) is then the ratio of the exposed surface area over the standard surface area. These two values together give us ideas whether a residue is exposed on the protein surface.

It is clear from Table 4 and FIG. 2 (right panel) that the binding site on p40 is discontinuous and constitutes a large number of surface exposed residues that are distributed over an irregular surface. The antibody-antigen interaction buries a total of 1758 Å$^2$ of accessible surface on IL-12 and p40 mAb. The interactions appear to be dominated by three salt bridges: R59(H)-E59(p40), R98(H)-E45(p40) and R99(H)-D62(p40). Also, there are contributions to the antibody-antigen interaction that are due to hydrophobic or Van der Waals forces.

The residues on the IL-12p40 antibody involved in IL-12 binding identified based upon the co-crystal structure herein are shown in Table 5 below. All surface exposed residues of the anti-p40 antibody with any atoms within 4 A of the p40 subunit are considered part of these binding residues. Conservative changes to any one or more of these residues may produce mutant antibodies that are of similar potency. Examples of such conservative substitutions include, without limitation, R59K, R98K and R99K in VH (e.g., SEQ ID NO:7) and DIE in VL (e.g., SEQ ID NO:8).

Also, saturation mutagenesis at each position shown in Table 5 can be performed (e.g., changing the wild type (WT) amino acid sequence to any other amino acid, possibly with the exception of Cysteine) to identify mutations causing the resulting antibody to have increased, decreased or substantially similar activity (e.g., binding). Binding of the resulting antibody to the p40 subunit can be tested pursuant to any suitable binding assay. Saturation mutagenesis can be used, for example, to create a more or less potent antibody or an equally potent antibody having different properties, i.e., properties other than potency resulting from a change in the variable region sequence (e.g., size or other structural changes to the variable region).

The saturation mutagenesis can also be performed using more than one substitution, for example, two, three, or more positions for each experiment. This can be done as individual clones or libraries followed by selection or screening in an appropriate format, such as phage display. Furthermore, individual or combination mutations at the positions in Table 5 that are desirable to regulate activity can be combined to create additional combination mutants of similar or better potency.

Advantage

The p40 mAb binding site is distant from the p40/p35 association site (FIG. 1). The p19 subunit of IL-23 is evolutionarily related to p35 of IL-12 with significant sequence homology. It is likely that p19 associates with p40 in a fashion similar to p35. Therefore, the p40 mAb binding region is also distant from the p40/p19 interaction in IL-23. The epitope identified in the present invention is equally available in both IL-12 and IL-23; accordingly, it is not surprising that p40 mAb can actively block the functions of both cytokines.

IL-12 (p40/p35) and IL-23 (p40/p19) interact with their respective receptors (IL-12Rβ1/β2 and IL-12Rβ1/IL-23R) in a similar fashion. They induce similar signaling cascades. The details of the cytokine-receptor interactions, however, are not clearly defined at the molecular level. The newly defined p40 mAb epitope could represent a biologically important site for the interactions between the IL-12 family of cytokines with their shared receptor, IL-12Rβ1. Therefore, the epitope is an important target for the therapeutic intervention using monoclonal antibodies, peptides, recombinant proteins, small molecules and other natural or synthetic agents.

Example 4: Epitope mapping of p40 mAb on IL-12p40 using mutational analysis

Summary

ELISA binding of IL-12p40 mutants with IL-12/IL-23p40 mAb was carried out to verify the binding epitope. Based on the crystal structure of p40 Fab/IL-12 complex, 7 single mutants and 2 double mutants were generated. The mutated residues are located in the p40 Fab contact region in the domain I (D1) of p40 subunit. The relative binding affinity showed that three negatively-charged residues, E45, E59 and D62, contribute significantly to binding interactions with p40 mAb. The other residues, M23, L40 and S43, have less but appreciable contribution. This mutational analysis confirms that p40 mAb recognizes domain I of p40 subunit and residues E45, E59, D62, M23, L40, and S43 are part of the binding epitope.

Materials and Methods

Seven human p40 single mutants, M23T, L40T, S43R, E45A, E45R, E59R, and D62R, and two double mutants, S43R/E45A and S43R/E45R, are used in the studies. The wide-type human p40, WT hu-p40, was used as the control. The p40 mutants were transiently expressed in HEK293E cells. The supernatants were used for binding assays.

In brief, MSD high bind plates (Meso Scale Discovery, MD) were coated with 5 µl of a capture monoclonal antibody (5 µg/ml) at room temperature for 1 hour. The capture monoclonal antibody recognizes p40 subunit but does not compete with p40 mAb. One-hundred and fifty (150) µl of 5% MSD Blocker A buffer was added to each well and incubated for 1 hr at room temperature. Plates were washed three times with 0.1 M HEPES buffer (pH 7.4). These protein-charged ELISA plates were incubated with 25 µl of different transiently expressed p40 mutant supernatants (1:10 dilution with 0.1 M HEPES buffer, pH 7.4) for 1 hr at room temperature. The plates were washed three times with 0.1 M HEPES buffer (pH 7.4). Twenty-five (25) µl of different concentrations of MSD Sulfo-TAG labeled p40 mAb, ranging from 0 to 20 µg/ml, were dispensed to micro-wells. After incubation for 2 hrs shaking at room temperature, plates were washed 3 times with 0.1 M HEPES buffer (pH 7.4). One hundred and fifty (150) µl of diluted MSD Read Buffer T was dispensed into each well and the plates were analyzed with a SECTOR imager (MSD).

Results

Figure 3:
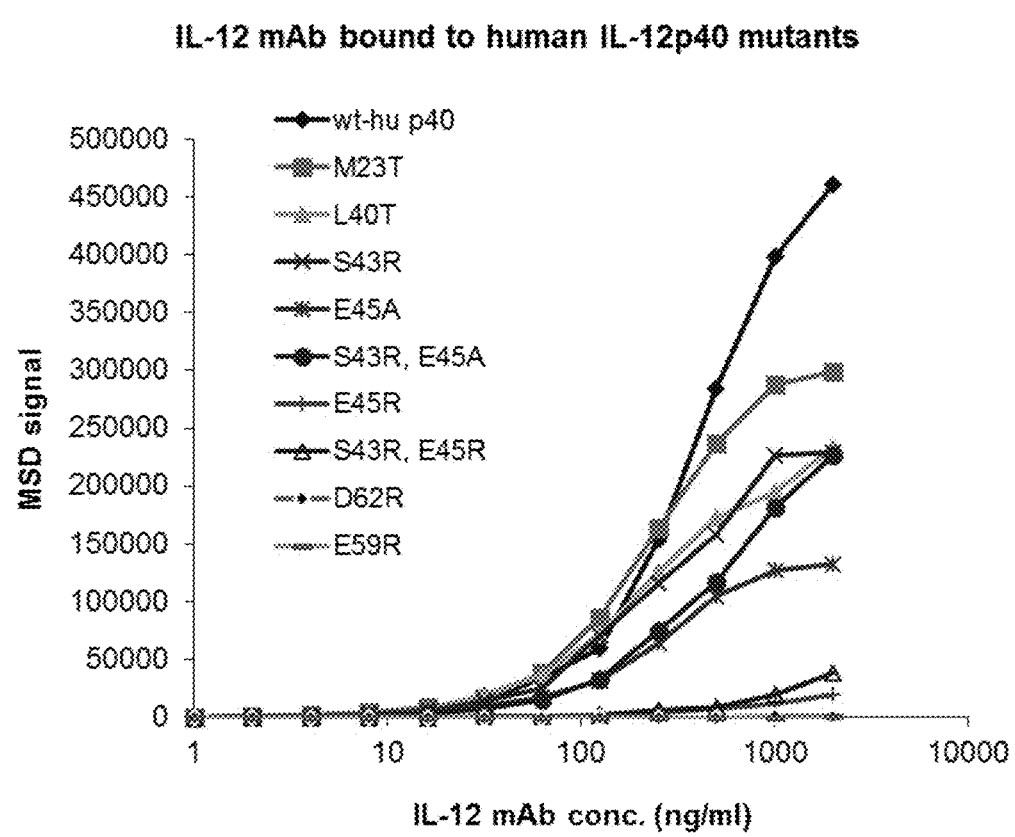
FIG. 3 shows the results of an ELISA evaluation of the IL-12 p40 antibody bound to various p40 single mutants.
Figure 4:
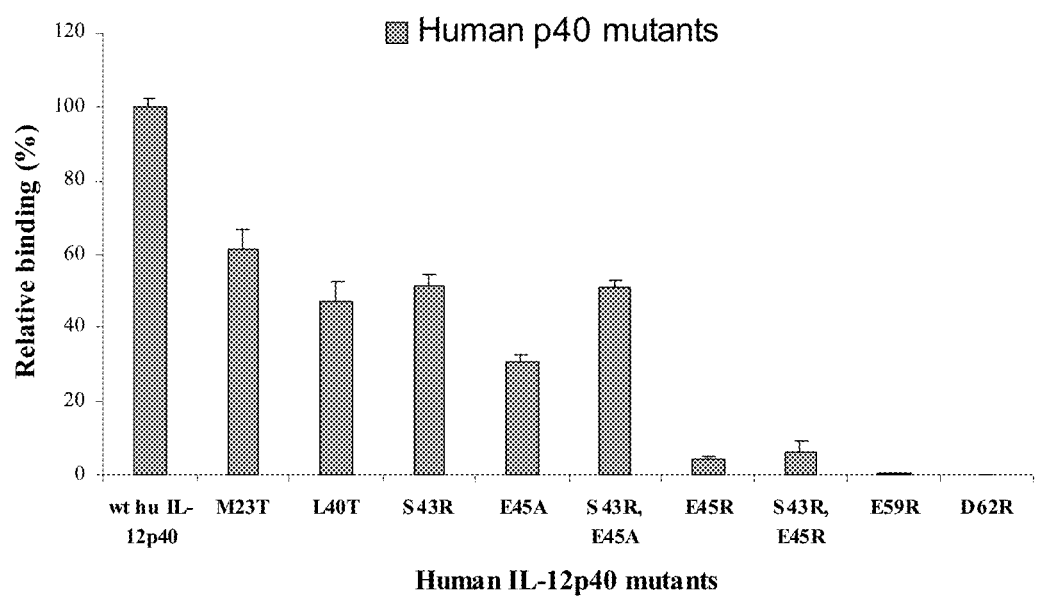
FIG. 4 shows the relative binding affinity of the p40 mAb to different p40 muteins.
Figure 5:
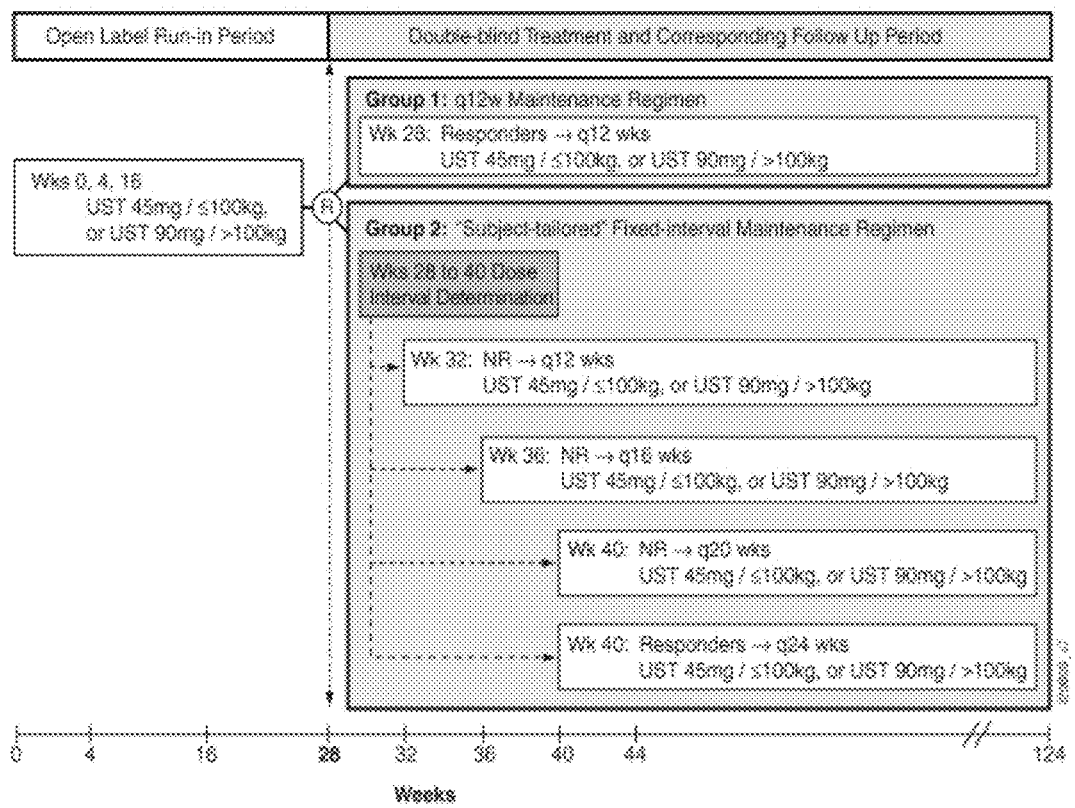
FIG. 5 shows a Study Schema of Ustekinumab in a Phase 3b, randomized, double-blind, active treatment-controlled, multicenter study with a 4-week screening period, an open-label run-in period from Week 0 to Week 28, a double-blind treatment period from Weeks 28 to Week 104, a post-treatment period through 116, and a safety follow-up via contact by telephone or an onsite visit at Week 124.

As shown in FIG. 3, E45R, E59R, and D62R each reduced the mutein p40 binding affinity to p40 mAb significantly, compared to the wild type p40. E45A had significant but less dramatic effect on the binding compared to E45R. M23T, L40T and S43R each had moderate effect upon binding.

The relative binding affinity of IL-12/IL-23p40 mAb to different mutant proteins was further analyzed by a capture assay. As shown in FIG. 4, E45R, E59R and D62R each nearly completely abolished antigen binding. The other mutations, M23T, L40T and S43R, in the interface, each reduced binding by approximately 40%. E45A reduced binding by about 70%.

It will be clear that the invention can be practiced otherwise than as particularly described in the foregoing description and examples. Numerous modifications and variations of the present invention are possible in light of the above teachings and, therefore, are within the scope of the appended claims.

TABLE 1

EAE clinical scores with IL-12 and IL-23 neutralization initiated on day −1 (prior to Th1 differentiation).

| Group | Incidence | Mortality | Day of onset | Highest acute cs[a] | Cumul cs[b] | Cs/day | No. of relapses | Relapse severity |
|---|---|---|---|---|---|---|---|---|
| P-2001-060 | | | | | | | | |
| Rat IgG | 13/13 | 4/13 | 30.5 ± 3.2 | 3.6 ± 0.3 | 71.4 ± 14.1 | 1.2 ± 0.2 | 1.3 ± 0.2 | 3.6 ± 0.2 |
| Anti-p35 | 11/13 | 8/13 | 29.6 ± 3.4 | 3.5 ± 0.5 | 45.5 ± 11.5 | 0.8 ± 0.2 | 1.2 ± 0.1 | 4.0 ± 0.3 |
| Anti-p40 | 1/13 | 0/13 | 40.0 | 0.1 | 1.2 ± 0.5 | 0.0 ± 0.0 | 0.0 ± 0.0 | 0.0 ± 0.0 |
| P-2001-079 | | | | | | | | |
| No treatment | 6/7 | 0/7 | 24.7 ± 2.7 | 3.2 ± 0.6 | 110.4 ± 20.4 | 1.7 ± 0.3 | 1.0 ± 0.4 | 3.8 ± 0.1 |
| Rat IgG | 9/9 | 2/9 | 29.1 ± 2.9 | 3.8 ± 0.2 | 90.6 ± 10.1 | 1.5 ± 0.1 | 0.3 ± 0.2 | 4.7 ± 0.3 |
| Anti-p35 | 10/10 | 1/10 | 30.0 ± 2.6 | 3.9 ± 0.2 | 94.9 ± 17.8 | 1.4 ± 0.2 | 0.7 ± 0.3 | 3.9 ± 0.2 |
| Anti-p40 | 1/10 | 0/10 | 61.0 | 0.3 | 1.6 ± 1.1 | 0.0 ± 0.0 | 0.0 ± 0.0 | 0.0 ± 0.0 |

[a]clinical score (cs)
[b]cumulative cs
Mice were treated as described and clinical scores were analyzed from day 0 through 70 days post EAE induction. Data is shown as the mean per group ± s.e.m.

TABLE 2

EAE clinical scores with IL-12 and IL-23 neutralization initiated on day 10 (after Th1 differentiation).

| Group | Incidence | Mortality | Day of onset | Highest acute cs[a] | Cumul cs[b] | Cs/day | # relapses | Relapse severity |
|---|---|---|---|---|---|---|---|---|
| P-2001-037 | | | | | | | | |
| No treatment | 7/8 | 0/8 | 30.6 ± 2.7 | 3.2 ± 0.5 | 51.5 ± 14.4 | 0.8 ± 0.2 | 0.3 ± 0.2 | 3.3 ± 0.8 |
| Rat IgG | 9/10 | 0/10 | 25.9 ± 2.7 | 2.7 ± 0.5 | 74.7 ± 15.8 | 1.2 ± 0.2 | 0.6 ± 0.2 | 3.7 ± 0.4 |
| Anti-p35 | 9/10 | 0/10 | 25.8 ± 2.6 | 2.5 ± 0.4 | 58.8 ± 15.6 | 1.0 ± 0.2 | 0.7 ± 0.3 | 3.2 ± 0.3 |
| Anti-p40 | 6/7 | 0/7 | 34.7 ± 6.3 | 1.6 ± 0.5 | 14.9 ± 7.5 | 0.2 ± 0.1 | 0.3 ± 0.2 | 1.5 ± 0.5 |
| P-2001-053 | | | | | | | | |
| No treatment | 8/9 | 2/9 | 15.8 ± 2.2 | 2.1 ± 0.6 | 56.4 ± 19.1 | 0.9 ± 0.3 | 0.6 ± 0.3 | 3.3 ± 0.5 |
| Rat IgG | 9/10 | 4/10 | 20.0 ± 2.5 | 3.8 ± 0.5 | 70.1 ± 17.7 | 1.3 ± 0.2 | 0.3 ± 0.2 | 4.2 ± 0.4 |
| Anti-p35 | 10/10 | 1/10 | 16.5 ± 1.1 | 3.2 ± 0.3 | 93.8 ± 15.7 | 1.4 ± 0.2 | 0.8 ± 0.2 | 3.2 ± 0.3 |
| Anti-p40 | 10/10 | 2/10 | 13.6 ± 1.1 | 2.7 ± 0.5 | 23.2 ± 7.9 | 0.4 ± 0.1 | 0.4 ± 0.3 | 2.0 ± 0.4 |

[a]clinical score (cs)
[b]cumulative cs
Mice were treated on days 10, 17, and 24 and clinical scores were analyzed from day 0 through 70 days post EAE induction. Data is shown as the mean per group ± s.e.m.

TABLE 3

EAE clinical scores with IL-12 and IL-23 neutralization initiated on day 30 (during established EAE). From first treatment through 80 days post EAE induction

| Group | Pre-Tx[a] | Mortality | Cumul cs[b] | Cs/day | Highest cs | Lowest cs | # relapses | Relapse severity |
|---|---|---|---|---|---|---|---|---|
| P-2002-01 | | | | | | | | |
| No treatment | 2.7 ± 0.6 | 1/5 | 132.9 ± 29.3 | 3.3 ± 0.3 | 4.1 ± 0.2 | 2.4 ± 0.5 | 0.6 ± 0.4 | 3.7 ± 0.0 |
| Anti-p35 | 2.3 ± 0.7 | 1/5 | 135.9 ± 16.5 | 2.7 ± 0.3 | 3.8 ± 0.4 | 1.8 ± 0.3 | 2.0 ± 0.4 | 3.7 ± 0.3 |
| Anti-p40 | 2.0 ± 0.2 | 1/6 | 75.6 ± 16.1 | 1.9 ± 0.3 | 2.8 ± 0.5 | 1.0 ± 0.4 | 0.7 ± 0.3 | 2.5 ± 1.0 |
| P-2002-093 | | | | | | | | |
| Rat IgG | 1.7 ± 0.8 | 1/5 | 87.7 ± 16.4 | 2.1 ± 0.2 | 3.7 ± 0.4 | 1.2 ± 0.5 | 1.5 ± 0.5 | 3.8 ± 1.0 |
| Anti-p35 | 1.9 ± 0.7 | 1/5 | 98.2 ± 9.7 | 2.2 ± 0.1 | 3.7 ± 0.4 | 1.4 ± 0.4 | 1.5 ± 0.3 | 3.3 ± 0.2 |
| Anti-p40 | 2.4 ± 0.8 | 0/5 | 71.7 ± 21.6 | 1.5 ± 0.4 | 2.9 ± 0.6 | 0.8 ± 0.5 | 1.3 ± 0.3 | 2.7 ± 0.6 |

[a] mean clinical score per group on the first day of treatment (Tx)
[b] clinical score (cs)

TABLE 4

Residues contributing to the p40 mAb binding epitope on IL-12/p40

| Number | Residue | sf | Sf Ratio |
|---|---|---|---|
| 15 | Trp | 94.2 | 0.36 |
| 17 | Pro | 69.3 | 0.46 |
| 18 | Asp | 132.9 | 0.86 |
| 19 | Ala | 27.7 | 0.22 |
| 20 | Pro | 131.5 | 0.88 |
| 21 | Gly | 18.7 | 0.21 |
| 23 | Met | 142.4 | 0.66 |
| 40 | Leu | 32.7 | 0.16 |
| 41 | Asp | 69 | 0.45 |
| 42 | Gln | 145.8 | 0.77 |
| 43 | Ser | 58.2 | 0.46 |
| 45 | Glu | 139.2 | 0.74 |
| 46 | Val | 95.8 | 0.57 |
| 47 | Leu | 95 | 0.48 |
| 54 | Thr | 77.2 | 0.51 |
| 55 | Ile | 32.7 | 0.17 |
| 56 | Gln | 111 | 0.58 |
| 58 | Lys | 69.2 | 0.32 |
| 59 | Glu | 83.2 | 0.44 |
| 60 | Phe | 113.3 | 0.51 |
| 61 | Gly | 68.2 | 0.77 |
| 62 | Asp | 41.3 | 0.27 |

TABLE 5

Residues on p40 mAb involved in binding to IL-2/p40 epitope

| Heavy chain residues | 1. Light chain residues |
|---|---|
| S28 | D1 |
| T31 | S30 |
| Y32 | W32 |
| W33 | Y49 |
| D57 | S56 |
| R59 | N92 |
| R98 | I93 |
| R99 | Y94 |
| R100 | |
| P101 | |
| G102 | |
| Q103 | |

Example 5: Results of Clinical Trials Using Increased Dosing Intervals

Ustekinumab was studied in a Phase 3b, randomized, double-blind, active treatment-controlled, multicenter study with a 4-week screening period, an open-label run-in period from Week 0 to Week 28, a double-blind treatment period from Weeks 28 to Week 104, a post-treatment period through 116, and a safety follow-up via contact by telephone or an onsite visit at Week 124 (see FIG. 5: Study Schema). The study was titled "Phase 3b, Randomized, Double-blind, Active-controlled, Multicenter Study to Evaluate a "Subject-tailored" Maintenance Dosing Approach in Subjects with Moderate-to-Severe Plaque Psoriasis (PSTELLAR)" under Protocol Number CNTO1275PSO3009. In FIG. 5, NR=nonresponder at a given timepoint; R=randomization of responders [defined as a PGA of <2] at Week 28 (subjects who are nonresponders [defined as a PGA of >2] at Week 28 will be discontinued from receiving further study agent injections, will be followed for safety for at least 20 weeks after their last study agent injection, and then will be withdrawn from the study); UST=ustekinumab; Wk(s)= Weeks.

All subjects enrolled were exposed to ustekinumab. At each injection visit prior to Week 28, subjects with baseline weight of ≤100 kg received one injection (ustekinumab 45 mg) and those with baseline weight >100 kg received 2 injections (ustekinumab 45 mg+ustekinumab 45 mg). At each injection visit from Week 28 to Week 104, subjects with baseline weight of ≤100 kg received one injection (ustekinumab 45 mg or placebo) and those with baseline weight >100 kg received 2 injections (ustekinumab 45 mg+ustekinumab 45 mg or placebo+placebo) depending on treatment group assignment and injection visit (see Table 7: Schedule for Study Agent Administration). The weight-based dose of study agent determined at baseline was utilized throughout the study. At Week 28, responders, defined as those subjects with a PGA of cleared (0) or minimal (1) were randomized with a 4 to 1 ratio into 2 groups, while non-responders (PGA score >2) discontinued from the study altogether.

Group 1 (n=76): Beginning at Week 28, subjects received fixed-interval maintenance dosing of ustekinumab q12w through the end of the study (i.e., Weeks 28, 40, 52, 64, 76, 88, and 100).

Group 2 (n=302): Beginning at Week 28, subjects received a tailored interval maintenance dosing. Using placebo injections, the period between study drug injections were extended in order to define their individually-tailored maintenance dosing interval. The study drug dosing interval for each subject was determined by assessing for maintenance of response without receiving a study drug injection at increments of 4 weeks until loss of PGA response was observed. At that point, subjects then assumed a study drug dosing interval defined by the longest interval for which a PGA response had been maintained (i.e., 4 weeks shorter than the time point at which loss of response was noted) or a maximal dosing interval of 24 weeks if response was maintained through the 24 weeks. Therefore, four different dose intervals were explored among subjects in Group 2, with respective treatment groups designated as Groups 2a, 2b, 2c and 2d:

a. With first loss of response (PGA score of ≥2) 16 weeks after the Week 16 injection (Week 32 visit), subjects would then receive ustekinumab q12w starting at Week 32 through Week 104 dosing visits (i.e., Weeks 32, 44, 56, 68, 80, 92, and 104).

b. With first loss of response (PGA score of ≥2) 20 weeks after the Week 16 injection (Week 36 visit), subjects would then receive ustekinumab q16w starting at Week 36 through Week 104 dosing visits (i.e., Weeks 36, 52, 68, 84, and 100).

c. With first loss of response (PGA score of ≥2) 24 weeks after the Week 16 injection (Week 40 visit), subjects would then receive ustekinumab q20w starting at Week 40 through Week 104 dosing visits (i.e., Weeks 40, 60, 80, and 100).

d. With no loss of response (PGA score of <2) 24 weeks after the Week 16 injection (Week 40 visit), subjects would then receive ustekinumab q24w starting at Week 40 through Week 104 dosing visits (i.e., Weeks 40, 64, and 88).

During the double-blind treatment period, subjects in Groups 1 and 2 received placebo injections as necessary to maintain the blind with regard to dosing interval. Subjects in Group 2 were to receive at least 3 cycles of subject-tailored Interval maintenance dosing during the randomized study period (see Table 7: Schedule for Study Administration).

Randomization: At Week 28, subjects with static PGA score of cleared (0) or minimal (1) were randomized in a 1:4 ratio to either Group 1 (the approved q12w maintenance regimen) or Group 2 ("subject-tailored" interval maintenance regimen) by using the randomly permuted blocks. The randomization was stratified by subject body weight at baseline [≤100 kg vs >100 kg] and PGA score [0 or 1] at Week 28.

Treatment duration/Trial duration: Subjects were dosed with study agent from Week 0 through Week 104. Subjects were then followed for at least an additional 20 weeks, with a final study visit at Week 124.

Primary analysis set for efficacy: The primary efficacy analysis was based on all subjects who were randomized to one of two treatment regimens (Group 1 or Group 2) at Week 28.

Primary efficacy variable/Primary time point: The primary endpoint is the number of visits at which subjects achieved a static PGA score of cleared (0) or minimal (1) between Week 88 and Week 112 (evaluation interval) for subjects randomized at Week 28. Assessment visits were conducted every 4 weeks during the evaluation interval.

Major secondary efficacy variables:
The proportion of subjects with a static PGA score of cleared (0) or minimal (1) and its 95% confidence interval by visit from Week 28 to Week 112 for subjects randomized at Week 28.

The number of visits for which subjects achieved a PASI 75 response between Week 88 and Week 112 for subjects randomized at Week 28.

The proportion of subjects with a PASI 75 response and its 95% confidence interval by visit from Week 28 to Week 112 for subjects randomized at Week 28.

Expected effect size and planned sample size: Based on data from PHOENIX 1 and PHOENIX 2, it was anticipated that approximately 35% of 500 enrolled subjects would be ineligible for randomization at Week 28 because of study discontinuation prior to Week 28 or the lack of a PGA score of cleared (0) or minimal (1) response at Week 28. The anticipated 325 subjects eligible for randomization at Week 28 in a 1:4 ratio would provide approximately 65 subjects in Group 1 (q12w maintenance dosing) and approximately 260 subjects in Group 2 (subject-tailored maintenance dosing).

The study was designed to estimate the response rates for 2 ustekinumab maintenance groups in greater than 300 subjects. A total of approximately 325 randomized subjects would provide a 95% confidence interval of 64.9% to 85.9% around a response of 75% in Group 1 (n=65; q12w maintenance dosing) and a 95% confidence interval of 54.0% to 66.0% around a response of 60% in Group 2 (n=260; subject-tailored maintenance dosing) during the evaluation period between Weeks 88 and 112.

Primary Objective:
The primary objective of this study was to assess the effect of extending maintenance dosing intervals beyond every 12 weeks (q12w) on the clinical efficacy of ustekinumab.

Topline Results Summary
CNTO1275PSO3009 is a Phase 3b, randomized, double-blind, active treatment-controlled, multicenter trial in adult subjects ≥18 to ≤80 years of age with moderate to severe plaque psoriasis, defined by PGA ≥3 and BSA involvement of at least 10%, who were candidates for phototherapy or systemic treatment of psoriasis.

The study began with its first subject screened on Mar. 8, 2012. A total of 611 subjects were screened, of which 478 subjects were enrolled into the study, and 378 subjects were randomized at Week 28 into the two treatment groups, one receiving the fixed q12 week interval maintenance regimen (Group 1) and the other receiving a subject-tailored maintenance dose interval regimen (Group 2). The study was conducted at 42 sites in USA. The final database lock includes data through Week 124 for all enrolled subjects. The first subject was dosed on Mar. 22, 2012. The first subject was randomized on Oct. 4, 2012 and the last subject was randomized on Sep. 16, 2013.

A total of 611 subjects were screened and 478 subjects were ultimately enrolled into the study. A total of 378 responders (PGA 0/1) were randomized at Week 28 (80% randomization rate). This randomization rate was higher than expected, which could be, in part, due to the subjective nature of the PGA scoring at Week 28. This final database lock included data through Week 124 for all enrolled subjects.

Distribution of Subjects by Treatment Groups and Subject Evaluability

A total of 478 subjects were enrolled and treated with ustekinumab through the open-label period, Week 0-28 run-in period, using the approved US weight-based dosing guidelines (ustekinumab 45 mg, n=308; ustekinumab 90 mg, n=170). A total of 378 subjects were randomized into 2 groups at Week 28: a fixed-interval every 12 week maintenance dosing group (Group 1) and a subject-tailored interval maintenance dosing group (Group 2). Using a 1:4 randomization ratio, a total of 76 subjects were randomized into Group 1 and 302 subjects were randomized into Group 2. The distribution of patients in Group 2 receiving maintenance dosing for each of the 4 potential dosing intervals was: q12w, n=84; q16w, n=61; q20w, n=51; and q24w, n=84.

Subject Demographics

Among overall enrolled subjects, the majority were white (84.9%), 63.0% were male and the median age was 46 years. Among all randomized subjects, most were white (76.7% for Group 1 and 89.4% for Group 2) and male (57.9% for Group 1 and 63.6% for Group 2). The median age was 42 years for Group 1 and 46 years for Group 2.

Subject Disease Characteristics

Among overall enrolled subjects, at baseline the median duration of psoriasis was 13.3 years, the median percent of body surface area (BSA) involved was 19.0%, the median PASI score was 16.0. A total of 35.8% of subjects presented with a PGA ≥4 consistent with severe disease; therefore, the majority of the subjects had moderate disease as defined by baseline PGA score of 3. Baseline disease characteristics of randomized subjects in Groups 1 and 2 were generally comparable, and were similar to those of the overall enrolled population. However subjects in Group 1, on average, had longer duration of disease (17.5 years) and higher baseline BSA of involved skin (21.0%) compared to subjects in Group 2 (11.8 years and 17.0% BSA, respectively).

Subject Psoriasis Medication History

Among overall enrolled subjects, 32.4% previously received phototherapy, 35.4% previously received conventional systemic therapy (including PUVA, methotrexate, acitretin, cyclosporine, mycophenolate mofetil) and 31.0% previously received biologic therapy. Generally, similar proportions were observed among subjects randomized to Groups 1 and 2. Among overall enrolled subjects, 69.0% were naïve to prior biologic use. Prior use of conventional systemic agents was slightly higher among subjects in Group 1 39.5% compared to Group 2 (31.1%). A higher proportion of subjects in Group 2 (74.5%) were naïve to prior biologic use compared to Group 1 (64.5%).

Discontinuation of Study Agent

During the open-label period (Week 0 through Week 28), 20.9% (100/478) of enrolled subjects discontinued use of study agent. Generally, similar proportions of subjects discontinued study agent in the 45 mg group (19.8%) and in the 90 mg group (22.9%). The most common reason for discontinuation was failure to achieve a static PGA score of cleared (0) or minimal (1) at Week 28 [12.1% (58/478)] to be eligible advance to the randomized portion of the study. During the randomized dosing period (Week 28 through Week 104), 22.2% (84/378) of randomized subjects discontinued study agent. The most common reason for discontinuation of study agent was loss to follow-up (7.9%) among Group 1 subjects and adverse event (5.0%) or withdrawal of consent (5.0%) among Group 2 subjects.

During the randomized treatment period (Week 28 to Week 104), 22.2% (84/378) of randomized subjects discontinued the study agent. Rates of discontinuation were similar between Groups 1 and 2 (Table 8). The most common reason for discontinuation of study agent among subjects in Group 1 was loss to follow-up (7.9%), and adverse event (5.0%) or withdrawal of consent (5.0%) among subjects in Group 2.

Efficacy Findings:

Primary Endpoint—

Group 2 had fewer visits (mean difference of −0.46) at which subjects had a PGA score of cleared (0) or minimal (1) (PGA 0/1) during the Week 88 and Week 112 evaluation interval compared to Group 1 (on average, Group 1 had 4.5 visits with PGA 0/1, and Group 2 had 4.1 visits with PGA 0/1).

Of note, during this interval Group 1 (55.3%) showed a higher proportion of subjects with a PGA score of 0/1 at all 7 visits during the evaluation interval compared to Group 2 (38.1%).

Secondary Endpoints—

Group 2 had fewer visits (mean difference of −0.32) at which subjects had a PASI 75 between Week 88 and Week 112 compared to Group 1 (on average, Group 1 had 5.8 visits with PASI 75, and Group 2 had 5.4 visits with PASI 75). The number of visits at which subjects had a PASI 75 response during the evaluation interval was similar for Groups 1 (69.7%) and Group 2 (66.9%).

Responses over time after randomization:

PGA 0/1 response rates decreased for both Groups 1 and 2 during the dose interval determination period (Week 28 to Week 40). As expected, a greater decrease was observed for Group 2 compared to Group 1, as defining subject-tailored dosing intervals was based on worsening of disease for Group 2 subjects. After Week 40, the PGA response rates for both groups were generally maintained through Week 112. Response rates at most visits were slightly higher for Group 1 compared to Group 2.

In general, patterns for PASI 75 responses reflected those for PGA responses from Week 28 through Week 112.

The proportions of subjects achieving PGA of cleared (0), PASI 90 or PASI 100 responses through Week 112 were generally higher for Group 1 compared to Group 2. The magnitude of the difference between the Groups 1 and 2 was greater for these endpoints compared to PGA 0/1 and PASI 75 endpoints.

Safety Findings:

For the randomized study population of 378 subjects, from Week 28 through Week 124:

The proportion of subjects experiencing 1 or more AEs was comparable between the two treatment groups (72.4%% in Group 1 and 72.8% in Group 2).

AEs were most frequently reported for the infections and infestations system organ class (SOC) for both Group 1 (46.1%) and Group 2 (48.7%; 48.1% for Groups 1 and 2 combined); the most common AEs in this SOC were URTI (27.6% in Group 1 and 19.5% in Group 2) and nasopharyngitis (9.2% in Group 1 and 13.2% in Group 2).

The proportions of subjects with one or more serious adverse events (SAEs) were 9.2% for Group 1 and 7.0% for Group 2.

The proportions of subjects who discontinued study agent due to one or more AEs (DCAE) were 6.6% for Group 1, and 5.6% for Group 2.

The proportions of subjects with one or more infections were comparable between the two groups (48.7% in Group 1 and 45.7% in Group 2). The most common infections in the combined group were URTI (27.6% in Group 1 and 19.5% in Group 2) and nasopharyngitis (9.2% in Group 1 and 13.2% in Group 2).

No serious infections were reported for subjects in Group 1; serious infections were reported for 3 subjects Group 2.

There were two investigator-reported major adverse cardiovascular events (MACE): 1 myocardial infarction (in a subject receiving 90 mg in Group 2 at a dosing interval of q24 weeks) and 1 stroke (in a subject receiving 45 mg in Group 2 at a dosing interval of q24 weeks).

Of the 378 randomized subjects there were 10 reported with at least one malignancy: 6 subjects with non-melanoma skin cancers (NMSC) and another 4 subjects with other malignancies.

No injection site reactions (ISRs) were reported among subjects in Group 1. In Group 2, 2.0% of placebo injections and 0.4% of 45 mg injections were associated with ISRs; all were of mild intensity.

Markedly abnormal changes in blood hematology and chemistry laboratory values were uncommon.

For the overall study population of 478 subjects enrolled at Week 0, through Week 124:

There were two deaths reported during the study. 1 death due to natural causes, and the other due to acute myeloid leukemia (AML). Neither death was reported during the open-label period (Week 0 through Week 28).

Through Week 124, there were 39 subjects (8.2% of the overall enrolled population) who experienced one or more SAEs.

Serious infection was reported for 7 subjects (1.5%).

No opportunistic infections or cases of active TB were reported.

Through Week 124, 7.3% of subjects among overall enrolled subjects discontinued study agent due to 1 or more AEs.

No possible anaphylactic or possible serum sickness-like reactions associated with ustekinumab were reported during the study.

A total of 12 enrolled subjects (2.5%) reported one or more malignancies (including NMSC and other malignancies): 5 subjects with BCC, 4 subjects with cutaneous SCC, 6 subjects with other malignancies There were 3 MACE reported in 3 subjects (0.6%): 2 with myocardial infarction and 1 with stroke.

Conclusions:

Efficacy was generally better maintained among Week 28 responders randomized to a fixed interval maintenance dosing (q12w) compared to those randomized to a subject-tailored interval maintenance dosing (q12w, q16w, q20, or q24w) especially for higher level efficacy endpoints (PGA 0, PASI 90, or PASI 100).

No new Safety signals were observed during the study period, and safety findings were similar between the two randomized groups.

Other analyses to better profile subjects in Group 2 who sustained response with longer dosing intervals through RNA and DNA analyses are on-going.

Extent of Exposure

A summary of the cumulative dose of ustekinumab received among randomized subjects from Week 28 through Week 124 is provided. The average number of study drug administrations was as expected for each treatment regimen and time period (6.1 for Group 1 and 4.1 for Group 2).

Primary Endpoint Analysis

Primary Endpoint

The primary endpoint for this study is the number of visits for which subjects had a static PGA score of cleared (0) or minimal (1) between Week 88 and Week 112 (the evaluation interval) for subjects randomized at Week 28 into Groups 1 and 2.

The evaluation interval included a total of 7 visits conducted every 4 weeks. The mean (95% confidence interval) number of visits for which subjects had a static PGA score of cleared (0) or minimal (1) during the evaluation interval was computed for Group 1 and Group 2. Under the assumption of normal distributions, the 95% confidence interval of the difference in means for the primary endpoint was provided.

The number of visits at which subjects achieved a PGA score of (0) or minimal (1) between Week 88 and Week 112 is summarized in Table 9 below.

Group 2 had fewer visits (mean difference of −0.46) at which subjects had a PGA score of cleared (0) or minimal (1) during the evaluation interval compared to Group 1. In addition, Group 1 (55.3%) showed a higher proportion of subjects with a PGA score of cleared (0) or minimal (1) at all 7 visits during the evaluation interval compared to Group 2 (38.1%). During this interval, it is interesting to note that Group 1 (55.3%) showed a higher proportion of subjects with a PGA score of 0/1 at all 7 visits during the evaluation interval compared to Group 2 (38.1%). Further, the proportions of subjects with no visits with a PGA response of cleared (0) or minimal (1) during the evaluation interval was similar for Group 1 (22.4%) and Group 2 (24.2%).

Subgroup Analysis

In general, there was not a substantial difference in the number of visits at which subjects achieved a static PGA score of cleared (0) or minimal (1) (PGA 0/1) during the evaluation interval among various analyzed subgroups of Groups 1 and 2. The subgroups are baseline demographic characteristics, baseline disease characteristics, and psoriasis medication history. Modest variability was observed in the number of visits for which subjects achieve PGA 0/1 between Week 88 and Week 112 across some subgroups; the observed variability could be due to the limited sample size within each subgroup.

Major Secondary Endpoint(s) Analysis

Major secondary analyses for the proportions (95% confidence interval) of subjects with a PGA score of cleared (0) or minimal (1) or a PASI 75 response over time were based on efficacy evaluable subjects randomized at Week 28 according to their assigned treatment groups, regardless of the actual treatment received. For the major secondary endpoint of the number of visits for which subjects achieve a PASI 75 response during the Week 88 to Week 112 evaluation interval, the same missing data handling rules applied to the primary analysis were also used, such that all randomized subjects were included in the analysis.

Figure 6:
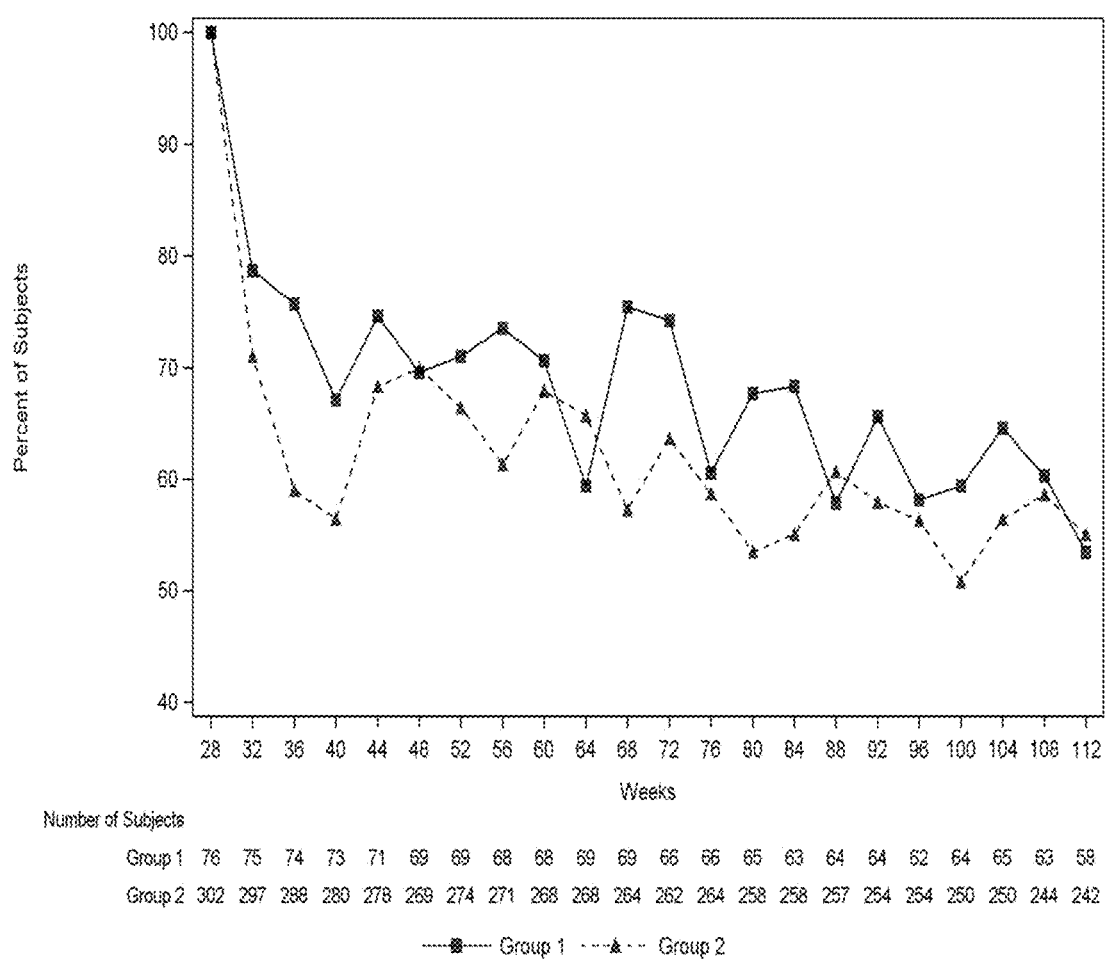
FIG. 6 shows the percent of subjects achieving a PGA Score of Cleared (0) or Minimal (1) from Week 28 through Week 112 by Visit in Study CNTO1275PSO3009.

PGA Score of Cleared (0) or Minimal (1) Responses from Week 28 Through Week 112 in the Randomized Subjects Population The PGA responses of cleared (0) or minimal (1) over time from Week 28 through Week 112 for Groups 1 and 2 are summarized in FIG. 6. PGA 0/1 response rates decreased for both groups during the dose interval determination period (Week 28 through Week 40), (FIG. 6; data on file). As expected, a greater decrease was observed for Group 2 compared to Group 1, as defining subject-tailored dosing intervals was based on worsening of disease for Group 2 subjects. At Week 40, the proportions of subjects achieving a PGA 0/1 were 67.1% for Group 1 and 56.4% for Group 2. After Week 40, some periodicity of responses based on variations at time points between q12 week injections, as seen in prior ustekinumab clinical trials, was observed more notably for Group 1, However, response rates, in general, were maintained at q12 week "trough" visits (e.g., Week 40, 52, 64, etc.), at which the next injection of ustekinumab would be due. Response rates for Group 2 were also generally maintained over time through Week 112. Response rates at most visits were slightly higher for Group 1 compared to Group 2 (FIG. 6).

The Number of Visits for which Subjects Achieved a PASI 75 Response Between Week 88 and Week 112 for Subjects Randomized at Week 28.

The number of visits during the evaluation interval at which subjects had a PASI 75 response is summarized in Table 10 below. Similar to corresponding analyses based on PGA responses, Group 2 had slightly fewer visits at which subjects had a PASI 75 response compared to Groups 1 (mean difference of −0.32 visits); on average, Group 1 had 5.8 visits with PASI 75, and Group 2 had 5.4 visits with PASI 75. Moreover, similar proportions of patients with a PASI 75 response between Groups 1 (69.7%) and Group 2 (66.9%) were observed for each potential number of visits with a response (ranging from 0 to 7).

Similar results for number of visits at which subjects had a PASI 75 response during the evaluation interval were observed for the subgroup analyses.

The Proportion of Subjects with a PASI 75 Response by Visit from Week 28 to Week 112 for Subjects Randomized at Week 28

Figure 7:
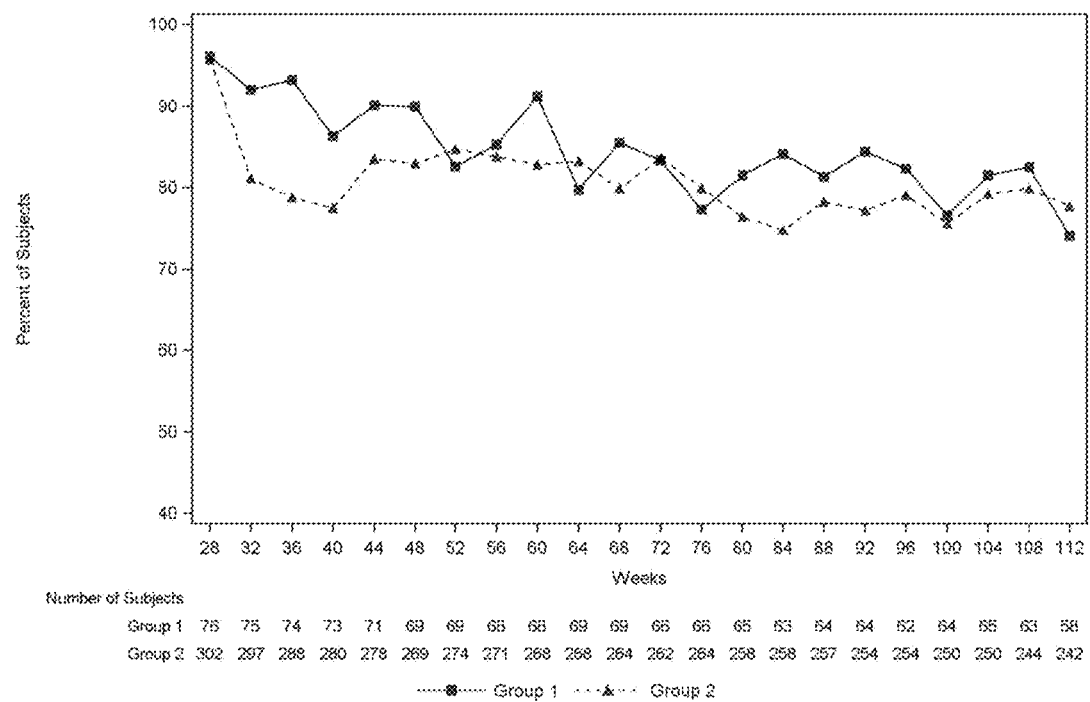
FIG. 7 shows percent of subjects achieving a PASI 75 Response from Week 28 through Week 112 by Visit in Study CNTO1275PSO3009.

PASI 75 response rates over time from Week 28 through Week 112 are summarized in FIG. 7. In general, the pattern of the PASI 75 responses over time from Week 28 through Week 112 parallels findings for PGA 0/1 responses (FIG. 6; data on file). However, the decrease in PASI 75 response rates in the Week 28 to Week 40 dose interval determination period is less compared to what was observed for PGA responses in this interval. After Week 40, the response rates for Group 1 and Group 2 were generally maintained through Week 112. The response rates of Group 1 at most visits were slightly higher for Group 1 compared to Group 2 from Week 44 through week 112. A pattern of q12 week periodicity for PASI 75 responses that was more pronounced for Group 1, similar to what was observed for PGA 0/1 responses, was noted. Since the PASI measure incorporates both body surface area and qualitative (erythema, scale, induration) elements, it may serve as a more consistent representation of overall disease burden over time compared to PGA alone which accounts only for qualitative features of psoriasis.

Other Secondary PGA Response Endpoints

PGA Score of Cleared (0) and PGA Score of Mild or Better (≤2) from Week 28 Through Week 112 for Subjects Randomized at Week 28

Figure 8:
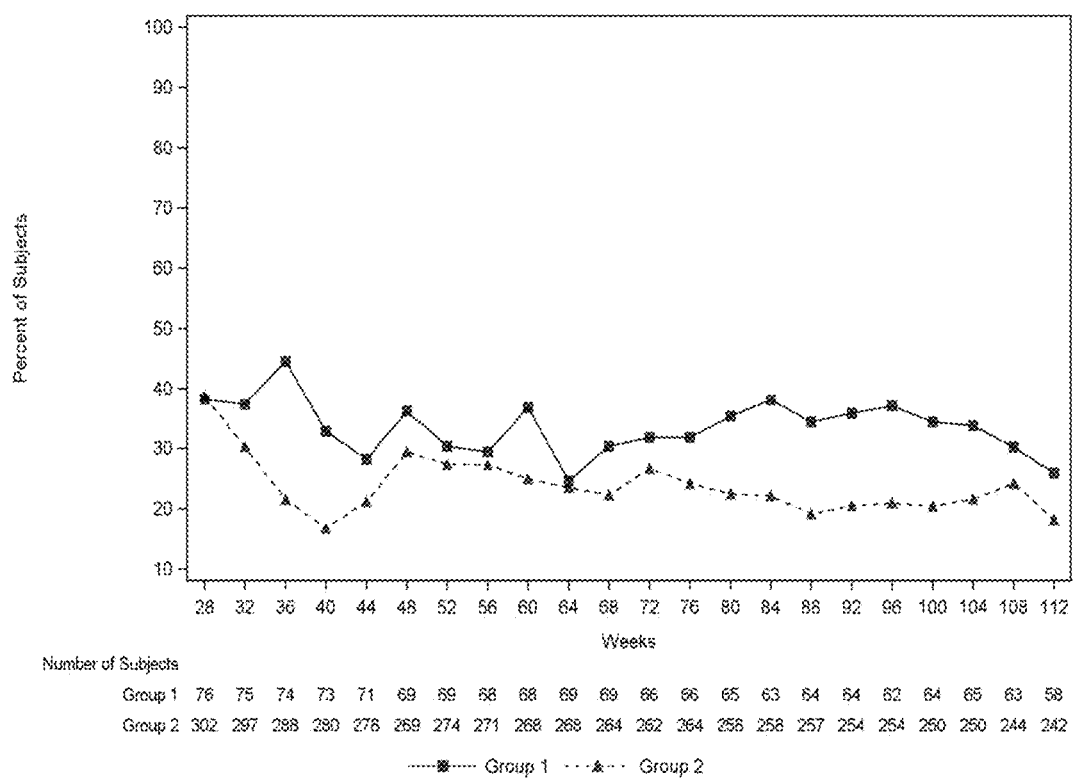
FIG. 8 shows PGA responses of cleared (0) over time from Week 28 through Week 112.

PGA responses of cleared (0) over time from Week 28 through Week 112 are summarized in FIG. 8. Separation between response curves for Group 1 (ustekinumab q12w maintenance regimen) and Group 2 (ustekinumab subject-tailored interval maintenance regimen) was apparent as early as the first post randomization visit (Week 32) and the response rates for Group 1 were consistently higher than those of Group 2 over time. Differences in PGA 0 responses between the two groups were more pronounced than those for either PGA 0/1 or PASI 75 responses, especially at later time points. The PGA scores of mild or better (PGA ≤2) over time from Week 28 through Week 112 were comparable for both groups and generally stable over time.

PGA Responses from Week 28 Through Week 112 for Subjects in the Subject-Tailored Interval Maintenance Regimen (Group 2)

The PGA scores of cleared (0), PGA scores of cleared (0) or minimal (1), and PGA responses of mild or better (≤2) from Week 28 through Week 112 were evaluated for Group 2 (data on file). For PGA responses of cleared (0) and cleared or minimal (0 or 1), as expected, subjects in the Group 2 q20 week and q24 week arms performed better than subjects in the Group 2 q12 week and q16 week arms. In addition, findings indicate that over 25% of initial responders randomized to Group 2 ultimately extended their dosing interval to q24 weeks and that most of these subjects maintained response over time.

Other Secondary PASI Response Endpoints

PASI Responses from Week 28 Through Week 112 for Subjects in the Subject-Tailored Interval Maintenance Regimen (Group 2)

The PASI 50, PASI 75, PASI 90 and PASI 100 over time from Week 28 through Week 112 for Group 2 are evaluated here (data on file). For PASI 75, PASI 90 and PASI 100, as expected, subjects in Group 2's q24w dosing regimen were observed to have better response than subjects in other groups in Group 2.

The Number of Visits for which Subjects had a PASI 75 Response Between Week 88 and Week 112 for Subjects in the Subject-Tailored Interval Maintenance Regimen (Group 2)

Results for the number of visits at which Group 2 subjects had a PASI 75 response between Week 28 and Week 112 are summarized in Table 11 below. The mean number of visits at which subjects had a PASI 75 response from Week 88 through Week 112 increased in parallel with length of dosing interval.

PASI 90 Responses from Week 28 Through Week 112 for Subjects Randomized at Week 28

Figure 9:
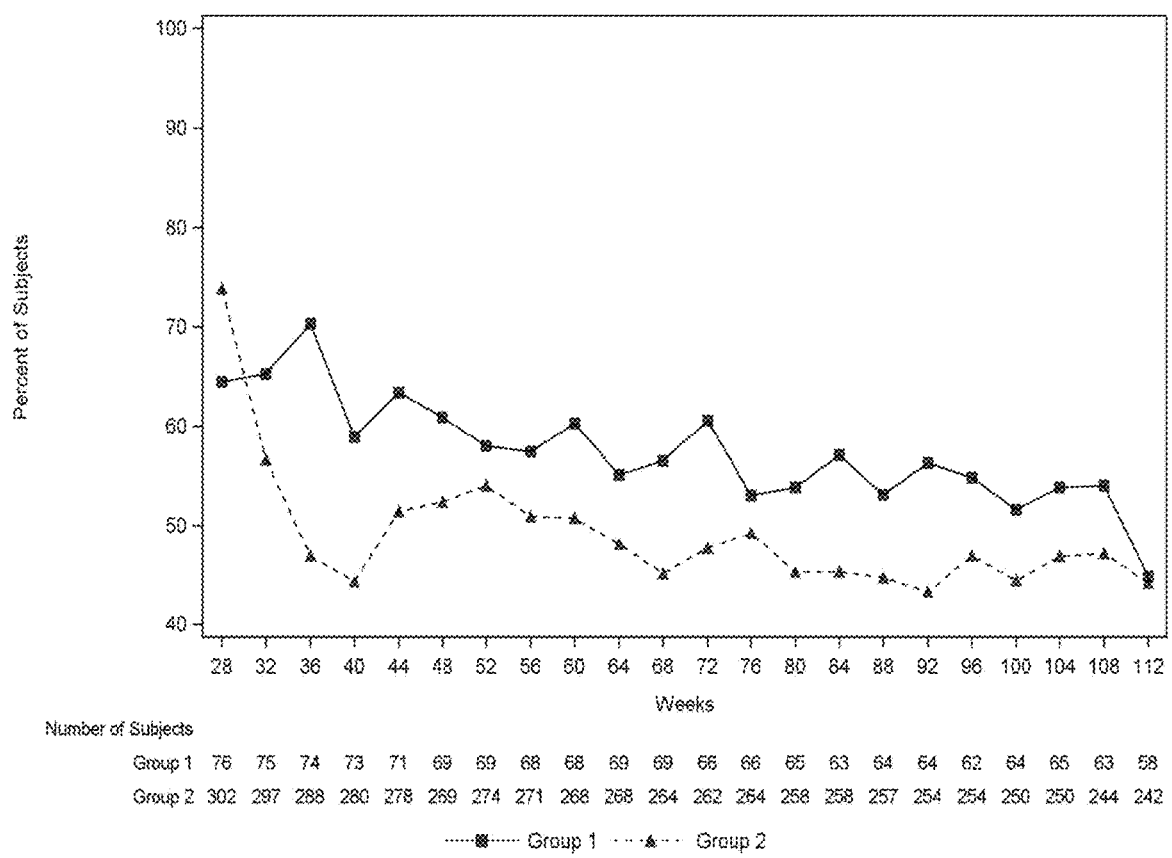
FIG. 9 shows the percent of subjects achieving a PASI 90 Response from Week 28 through Week 112 by Visit in Study CNTO1275PSO3009.

PASI 90 response rates from Week 28 through Week 112 are summarized in FIG. 9 (data on file). Separation between the response curves for Group 1 (ustekinumab q12w maintenance regimen) and Group 2 (ustekinumab subject-tailored interval maintenance regimen) were also observed starting at the first post randomization visit (Week 32) and maintained through Week 108 (FIG. 9). The proportion of subjects achieving and maintaining a PASI 90 response was higher for Group 1 compared to Group 2. The separation between the PASI 90 response curves for Groups 1 and 2 Group 2 is more pronounced compared to findings for PGA 0/1 and PASI 75 response curves.

Safety

Safety evaluations focus on the double-blinded portion of the study extending from Week 28 through Week 124 as comparisons between randomized treatment groups can be made. Supportive data through Week 124 are also presented. Table 12 below provides an overview of the key safety results from 28 through Week 124.

All Adverse Events

For treated subjects randomized at Week 28, from Week 28 through Week 124:
  The proportions of subjects experiencing 1 or more AEs were similar for Group 1 (72.4%) and Group 2 (72.8%); see Table 12 (data on file). AEs were most frequently reported for the infections and infestations system organ class (SOC) for both Group 1 (46.1%) and Group 2 (48.7%; 48.1% for Groups 1 and 2 combined).
  The most common AEs in this SOC were URTI (27.6% in Group 1 and 19.5% in Group 2) and nasopharyngitis (9.2% in Group 1 and 13.2% in Group 2).

For overall enrolled subjects, from Week 0 through Week 124:
  Overall, 72.6% of subjects experienced 1 or more AEs. Similarly, AEs were most commonly reported for the infections and infestations SOC (49.8%), with URTI (19.9%) and nasopharyngitis (13.8%) representing the most commonly reported AEs.

Deaths, Other Serious Adverse Events, and Other Significant Adverse Events

Deaths

There were two deaths through Week 124. One subject (Ser. No. 00/009,010) was reported to have died of natural causes. This subject had been treated with ustekinumab 90 mg and was randomized to Group 1 fixed interval q12 week treatment arm.

The other subject (Ser. No. 00/029,005) died of acute myeloid leukemia (AML). This subject had elevated platelet counts prior to enrollment and AML was diagnosed 2 years after the first study dose. This subject had been receiving ustekinumab 90 mg and was in the Group 2 subject-tailored q12 week treatment arm.

Other Serious Adverse Events

The proportions of treated subjects randomized at Week 28 who experienced one or more serious adverse events (SAEs) through Week 124 were low for both Group 1 (9.2%) and Group 2 (7.0%) (Table 5). No particular pattern of SAEs was observed and most SAEs were reported as single and isolated events. Among overall enrolled subjects 8.2% (39/478) experienced 1 or more SAEs from Week 0 through Week 124 (data on file).

Adverse Events that Resulted in Study Agent Discontinuation

Among treated randomized subjects, the proportions of subjects who discontinued study agent between Week 28 and Week 124 due to one or more AEs (DCAE) were low (6.6% for Group 1, 5.6% for Group 2) [see Table 12]. No pattern of AEs leading to discontinuation was observed and most were reported as single events.

Among overall enrolled subjects, 7.3% discontinued study agent due to 1 or more AEs between Week 0 and Week 124 (data on file).

Infections, Serious Infections and Infections Requiring Treatment

Among treated randomized subjects, comparable proportions of subjects in Groups 1 and 2 (48.7% and 45.7%, respectively; Table 5) experienced one or more infections from Week 28 through Week 124. The most common infections were URTI (27.6% of subjects in Group 1 and 19.5% in Group 2) and nasopharyngitis (9.2% of subjects in Group 1 and 13.2% in Group 2).

There were no serious infections reported in Group 1, and 3 serious infections were reported among Group 2 subjects (Table 12). Reported serious infections included 1 case of bacterial infection, 1 case of cystitis, and 1 case of urinary tract infection.

Infections requiring oral or parenteral antimicrobial treatment were reported in 18 of 76 (23.7%) Group 1 subjects and 70 of 302 (23.2%) Group 2 subjects (see Table 12). Overall, URTI was the most frequent type of infection that required treatment (5.3% in Group 1; 5.0% in Group 2).

Among overall enrolled subjects, 47.3% experienced 1 or more infections between Week 0 and Week 124 (data on file). The most commonly reported infections were URTI (19.9%) and nasopharyngitis (11.7%). The proportion of subjects with one or more serious infections was 1.5% (data on file). No cases of active TB or opportunistic infection were reported through Week 124.

Injection Site Reactions

From Week 28 through Week 124, no injection site reactions (ISRs) were reported among Group 1 subjects for either placebo or 45 mg injections. Among Group 2 subjects, 6 ISRs related to administration of placebo (2.0%) and 1 ISR from an injection of ustekinumab 45 (0.4%) were observed. All reported ISRs were of mild severity (data on file).

Possible Anaphylactic or Possible Serum Sickness-Like Reactions Associated with Ustekinumab No subjects experienced a possible anaphylactic reaction or possible serum sickness-like reaction associated with administration of study agent through Week 124.

Malignancies

Among treated randomized subjects, 10 reported at least one malignancy between Week 28 and Week 124 (Table 12). Six of 378 (1.6%) subjects had a non-melanoma skin cancer (NMSC), including 2 of 76 (2.6%) Group 1 subjects and 4 of 302 Group 2 subjects (1.3%).

Four of 378 (1.1%) treated randomized subjects reported other types of malignancies. One of 76 (1.3%) Group 1 subjects had a transitional cell bladder carcinoma (45 mg dosing). Three of 302 (1.0%) Group 2 subjects had a malignancy, including 1 case each of pancreatic carcinoma (45 mg dosing), acute myeloid leukemia (90 mg dosing), and chronic myeloid leukemia (90 mg dosing).

Among overall enrolled subjects, malignancies (including NMSC and other malignancies) 2.5% (12/478) reported a malignancy between Week 0 and Week 124. Three cases of NMSC and 2 other malignancies (1 colon cancer (90 mg dosing) and 1 prostate cancer (90 mg dosing) were reported in addition to those described above among treated randomized subjects.

Cardiovascular Events

Two investigator-reported MACE were observed among treated randomized patients from Week 28 through Week 124. One Group 2 subject (Subject 001050002) receiving ustekinumab 90 mg in the q24 week interval arm had a myocardial infarction (and 1 Group 2 subject (Subject 001027002) receiving ustekinumab 45 mg also in the q24 week interval arm had a stroke. One additional investigator-reported MACE, a myocardial infarction in a subject receiving ustekinumab 45 mg (Subject 001029007), occurred prior to Week 28.

Laboratory Measurements

Markedly abnormal changes in hematology laboratory values were observed in some subjects, but rates of markedly abnormal labs were generally low and comparable between Groups 1 and 2 from Week 28 through Week 124 (data on file). The most common reported markedly abnormal change in hematology lab values was decreased lymphocytes (5.3% [20/378]). Markedly abnormal hematology lab values occurring on more than 1 occasion were observed only in Group 2, and included elevated WBC (0.3%), decreased lymphocyte count (1.3%), and elevated eosinophil count (0.3%).

Markedly abnormal changes in chemistry laboratory values were also observed in some subjects (data on file). Rates of markedly abnormal labs were generally low in both Groups 1 and 2. The only markedly abnormal changes that occurred on more than 1 occasion were elevated alkaline phosphatase, ALT, AST, and total bilirubin levels, all of which observed in Group 2 subjects and at a low rate. The most common markedly abnormal change occurring across both Groups 1 and 2 was elevated ALT level (3.2% [12/378]).

Immunogenicity

Of the ustekinumab-treated population with evaluable samples through Week 124, 63 of 455 (13.8%) patients tested positive for antibodies to ustekinumab. This percentage is similar among patients receiving the 45 mg dose (n=41; 13.9%) to those receiving the 90 mg dose (n=22; 13.7%) and across Group 1 (n=7; 9.2%) and Group 2 (n=32; 10.6%). A majority of antibody-positive patients (33 out of 63) had titers ≤1:800. Most of the antibodies developed (from antibody-positive patients with sufficient serum samples) were able to neutralize the bioactivity of ustekinumab in vitro (47 out of 62 (75.8%). In testing dosing intervals that allowed declining ustekinumab concentrations below quantifiable levels between injections (which approximates multiple withdrawal and retreatment cycles), no increased susceptibility to anti-drug antibody developed was identified. These results suggest that there is no increased risk of immunogenicity when increasing the dosing interval to up to a 24-week interval.

Predictive Value of PGA=0 at Week 28

Group 2 patients who stably maintained clinical responses over time with a 24-week dosing interval generally demonstrated high levels of response for the most stringent measures through the initial run-in treatment period. Because a high proportion of 24-week dosing interval subgroup patients had a PGA of 0 at Week 28 (Table 6), the utility of this response parameter to be a predictive marker for ability to maintain clinical response at this interval was evaluated. Obtaining a PGA=0 at Week 28 correlated with a PPV of 60% for maintaining a PGA of 0 or 1 with any dosing interval larger than 12 weeks (e.g., 16 weeks, 20 weeks, 24 weeks) for ≥five out of seven Week 88 to Week 112 assessment period visits. Also, there was a PPV of 44% for maintaining a PGA of 0 or 1 with any dosing interval larger than 12 weeks for all seven of the visits. Obtaining a PGA=0 at Week 28 correlated with PPV's of 44% and 32%, respectively, for PGA of 0 for ≥five out of seven Week 88 to Week 112 assessment period visits and all seven visits. The sensitivity and specificity ranged between 61 and 75% for these determinations as shown in Table 6.

TABLE 6

Ability of PGA = 0 at Week 28 to predict long-term response with q12-24 wk response-based dosing, among all patients randomized at Week 28

| Visits with PGA <2 during Week 88-Week 112 by Sensitivity Specificity maintenancedosinginterval | (TPR)[a] | (FPR)[b] | PPV[c] | NPV[d] |
|---|---|---|---|---|
| q24 wk maintenance dosing | | | | |
| ≥5 visits | 75% | 72% | 44%[a] | 91%[b] |
| 7 visits | 75% | 69% | 32%[a] | 93%[b] |
| q20 wk or q24 wk maintenance dosing | | | | |
| ≥5 visits | 66% | 74% | 53% | 83% |
| 7 visits | 69% | 70% | 41% | 88% |
| >q12 wk maintenance dosing[e] | | | | |
| ≥5 visits | 61% | 75% | 60% | 76% |
| 7 visits | 63% | 70% | 44% | 88% |

[a]Sensitivity, or the "True Positive Rate" (TPR), represents the proportion of non-q12 w or q24 w maintenance subgroup patients that can be correctly identified by the predictive marker or test.
[b]Specificity, or the "True Negative Rate" (TNR), represents the proportion of patients that should be excluded from the predicted group that is suggested if the predictive marker is negative.
[c]PPV represents the probability of a given outcome if a predictive marker is positive, i.e., post-test likelihood of a positive outcome. As further explanation, these particular PPVs are based upon the observation that 117/302 Group 2 patients had PGA = at Week 28 and 51/117 (44%) patients received q24 wk maintenance dosing and had PGA <2 at five or more visits during Week 88-Week 112. Similarly, 38/117 (32%) of these Group 2 q24 wk patients had PGA <2 at all seven visits during Week 88-Week 112.
[d]NPV represents the probability of a negative outcome if a predictive marker is negative, i.e., post-test likelihood of a negative outcome. As further explanation, these particular NPVs derive from the observation that 17/185 Group 2 patients with PGA = 1 at Week 28 were treated with q24 wk maintenance dosing and had PGA <2 at five or more visits (NPV = [185 − 17])/185 = 91%), and 13/185 had PGA <2 at all seven visits (NPV = [185 − 13]/185 = 93%) between Week 88-Week 112.
[e]>q12 wk includes q16 wk, q20 wk, and q24 wk maintenance dosing intervals.
FPR—false positive rate, NPV—negative predictive value, PGA—Physician's Global Assessment, PPV—positive predictive value, q12/16/20/24 wk —every 12/16/20/24 weeks, TPR—true positive rate

TABLE 7

Schedule for Study Agent Administration

| Open-label run-in period Weeks | | | Subjects with a static PGA score of cleared (0) or minimal (1) will be randomized at Week 28 to 1 of 2 treatment groups. Group 1 will receive the approved maintenance regimen. In group 2, the time of loss of response (defined as a PGA score ≥ 2) will determine the mainenance regimen.[a] | Double-blind treatmeant period (Weeks) | | | | | | | | | | | | | | | | | | |
|---|---|---|---|---|---|---|---|---|---|---|---|---|---|---|---|---|---|---|---|---|---|---|
| 0 | 4 | 16 | | 28[b] | 32[b] | 36[b] | 40[b] | 44 | 48 | 52 | 56 | 60 | 64 | 68 | 72 | 76 | 80 | 84 | 88 | 92 | 96 | 100 | 104 |
| A | A | A | Group 1: Maintenance dosing according to approved regimen (ustekinumab q12w beginning at Week 28) | A | P | P | A | P | | A | P | P | A | P | | A | P | P | A | P | | A | P |
| A | A | A | Group 2a: If loss of response occurs at 16 weeks after the Week 16 injection (i.e., the Week 32 visit), subjects will receive ustekinumab q12w beginning at Week 32. | P | A | P | P | A | | P | A | P | P | A | | P | A | P | P | A | | P | A |
| A | A | A | Group 2b: If loss of response occurs at 20 weeks after the Week 16 injection (i.e., the Week 36 visit), subjects will receive ustekinumab q16w beginning at Week 36. | P | P | A | P | P | | A | P | P | P | A | | P | P | A | P | P | | A | P |
| A | A | A | Group 2c: If loss of response occurs at 24 weeks after the Week 16 injection (i.e., the Week 40 visit), subjects will receive ustekinumab q20w beginning at Week 40. | P | P | P | A | P | | P | P | A | P | P | | P | A | P | P | P | | A | P |

TABLE 7-continued

Schedule for Study Agent Administration

| Open-label run-in period Weeks | | | | Subjects with a static PGA score of cleared (0) or minimal (1) will be randomized at Week 28 to 1 of 2 treatment groups. Group 1 will receive the approved maintenance regimen. In group 2, the time of loss of response (defined as a PGA score ≥ 2) will determine the mainenance regimen.[a] | Double-blind treatmeant period (Weeks) | | | | | | | | | | | | | | | | |
|---|---|---|---|---|---|---|---|---|---|---|---|---|---|---|---|---|---|---|---|---|---|
| 0 | 4 | 16 | | | 28[b] | 32[b] | 36[b] | 40[b] | 44 | 48 | 52 | 56 | 60 | 64 | 68 | 72 | 76 | 80 | 84 | 88 | 92 | 96 | 100 | 104 |
| A | A | A | A | Group 2d: If no loss of response occurs up to 24 weeks after the Week 16 injection (i.e., the Week 40 visit), subjects will receive ustekinumab q24w beginning at Week 40. | P | P | P | A | P | | P | P | P | A | P | | P | P | P | A | P | | P | P |

A = Active treatment with 45 mg ustekinumab (for subjects who weigh ≤ 100 kg) or 90 mg ustekinumab (for subjects who weigh > 100 kg)
P = Placebo
= No study agent administration
[a]Subjects who do not receive a static PGA of cleared (0) or minimal (1) at Week 28, or have discontinued study agent prior to Week 28, have not received all 3 study agent injections prior to Week 28 (i.e., the Week 0, 4, 16 injections), will be discontinued from receiving further study agent injections, will be followed for safety for at least 20 weeks after their last study agent injection, and then will be withdrawn from the study.
[b]At these visits, the PGA score needs to be put into the IVRS/IWRS. At these visits special consideration should be given to the timing of the visit to allow for study agent allocation based on disease activity.
Note:
At each applicable visit, subjects will receive 1 to 2 injections. Those weighing ≤ 100 kg will receive 1 injection (45 mg ustekinumab or placebo) and those weighing > 100 kg will receive 2 injections (45 mg ustekinumab + 45 mg ustekinumab or placebo + placebo) depending on treatment group assignment and visit. The dose of study agent determined at baseline using weight will be the dose utilized throughout the study.

TABLE 8

Number of Subjects Who Discontinued Study Agent from Week 28 through Week 104; All Subjects Randomized at Week 28 (Study CNTO1275PSO3009)

| | Group 1 ustekinumab q12w maintenance regimen | Group 2 ustekinumab subject-tailored Interval maintenance regimen | | | | | |
|---|---|---|---|---|---|---|---|
| | | All randomized subjects | q12w | q16w | q20w | q24w | Total |
| Analysis set: all subjects randomized at Week 28 | 76 | 302 | 84 | 61 | 51 | 84 | 378 |
| Subjects who discontinued study agent | 17 (22.4%) | 67 (22.2%) | 17 (20.2%) | 7 (11.5%) | 7 (13.7%) | 14 (16.7%) | 84 (22.2%) |
| Reason for discontinuation | | | | | | | |
| Adverse event | 4 (5.3%) | 15 (5.0%) | 4 (4.8%) | 3 (4.9%) | 2 (3.9%) | 3 (3.6%) | 19 (5.0%) |
| Death | 1 (1.3%) | 0 | 0 | 0 | 0 | 0 | 1 (0.3%) |
| Lack of efficacy | 2 (2.6%) | 8 (2.6%) | 4 (4.8%) | 2 (3.3%) | 1 (2.0%) | 1 (1.2%) | 10 (2.6%) |
| Lost to follow-Up | 6 (7.9%) | 12 (4.0%) | 3 (3.6%) | 0 | 3 (5.9%) | 3 (3.6%) | 18 (4.8%) |
| Pregnancy | 0 | 3 (1.0%) | 1 (1.2%) | 0 | 0 | 0 | 3 (0.8%) |
| Protocol violation | 0 | 4 (1.3%) | 1 (1.2%) | 0 | 0 | 0 | 4 (1.1%) |
| Study terminated by sponsor | 0 | 0 | 0 | 0 | 0 | 0 | 0 |
| Withdrawal of consent | 2 (2.6%) | 15 (5.0%) | 3 (3.6%) | 1 (1.6%) | 0 | 6 (7.1%) | 17 (4.5%) |
| Other | 2 (2.6%) | 10 (3.3%) | 1 (1.2%) | 1 (1.6%) | 1 (2.0%) | 1 (1.2%) | 12 (3.2%) |

[TSIDS01B.RTF] [CNTO1275\PSO3009\DBR_WEEK_124\RE_WEEK_124_CSR\PREPROD\TSIDS01B.SAS] 30SEP2015, 10:53

TABLE 9

Number of Visits for Which Subjects Achieved a PGA Score of Cleared (0) or Minimal (1) between Week 88 and Week 112; All Subjects Randomized at Week 28 (Study CNT01275P503009)

| | Group 1 ustekinumab q12 w maintenance regimen | Group 2 ustekinumab subject-tailored interval maintenance regimen |
|---|---|---|
| Analysis set: all subjects randomized at Week 28 | 76 | 302 |
| N[a] | 76 | 302 |
| Mean | 4.5 (3.07) | 4.1 (2.93) |
| 95% confidence interval of mean[b] | (3.81; 5.21) | (3.72; 4.39) |
| Median | 7.0 | 5.0 |
| Range | (0; 7) | (0; 7) |
| IQ range | (1.0; 7.0) | (1.0; 7.0) |
| Difference between treatment groups | | −0.46 |
| 95% confidence interval[b] | | (−1.20; 0.29) |

TABLE 9-continued

Number of Visits for Which Subjects Achieved a PGA Score of Cleared (0) or Minimal (1) between Week 88 and Week 112; All Subjects Randomized at Week 28 (Study CNT01275P503009)

|  | Group 1 ustekinumab q12 w maintenance regimen | Group 2 ustekinumab subject-tailored interval maintenance regimen |
|---|---|---|
| Number of visits for which subjects with a PGA score of cleared (0) or minimal (1) | | |
| 0 | 17 (22.4%) | 73 (24.2%) |
| 1 | 6 (7.9%) | 19 (6.3%) |
| 2 | 2 (2.6%) | 17 (5.6%) |
| 3 | 3 (3.9%) | 17 (5.6%) |
| 4 | 2 (2.6%) | 16 (5.3%) |
| 5 | 2 (2.6%) | 20 (6.6%) |
| 6 | 2 (2.6%) | 23 (7.6%) |
| 7 | 42 (55.3%) | 117 (38.7%) |

[a]After applying treatment failure rules, subjects with any missing data between Weeks 88 and 112 were handled as follows:
(1) If a missing visit was intermittent, the missing value was imputed with the weighted average relative to the distance of the available values before and after the missing visit (a linear relationship was assumed across the visits). The resulting score was rounded to the nearest integer.
(2) If a missing visit was not intermittent, i.e., there were no data available after the missing visit, a last observation carried forward method was used to impute the missing data.
[b]95% confidence interval was based on normal approximation.
[TEFPGA01A.RTF] [CNTO1275 \ PSO3009 \DBR_WEEK_124\ RE_WEEK_124_CSR\ PROD \TEFPGA01A.SAS] 01OCT2015, 14:17

TABLE 10

Number of Visits for Which Subjects Achieved a PASI 75 Response between Week 88 and Week 112; All Subjects Randomized at Week 28 (Study CNTO1275PSO3009)

|  | Group 1 ustekinumab q12 w maintenance regimen | Group 2 ustekinumab subject-tailored interval maintenance regimen |
|---|---|---|
| Analysis set: all subjects randomized at Week 28 | 76 | 302 |
| N[a] | 76 | 302 |
| Mean (SD) | 5.8 (2.31) | 5.4 (2.61) |
| 95% confidence interval of mean[b] | (5.23; 6.29) | (5.15; 5.74) |
| Median | 7.0 | 7.0 |
| Range | (0; 7) | (0; 7) |
| IQ range | (6.0; 7.0) | (5.0; 7.0) |
| Difference between treatment groups |  | −0.32 |
| 95% confidence interval[b] |  | (−0.96; 0.33) |
| Number of visits for which subjects with a PASI 75 response | | |
| 0 | 7 (9.2%) | 43 (14.2%) |
| 1 | 2 (2.6%) | 7 (2.3%) |
| 2 | 0 | 8 (2.6%) |
| 3 | 5 (6.6%) | 5 (1.7%) |
| 4 | 1 (1.3%) | 9 (3.0%) |
| 5 | 2 (2.6%) | 11 (3.6%) |
| 6 | 6 (7.9%) | 17 (5.6%) |
| 7 | 53 (69.7%) | 202 (66.9%) |

[a]After applying treatment failure rules, subjects with any missing data between Weeks 88 and 112 were handled as follows:
(1) If a missing visit was intermittent, the missing value was imputed with the weighted average relative to the distance of the available values before and after the missing visit (a linear relationship was assumed across the visits).
(2) If a missing visit was not intermittent, i.e., there were no data available after the missing visit, a last observation carried forward method was used to impute the missing data.
[b]95% confidence interval was based on normal approximation.
[TEFPASI01.RTF]    [CNTO1275\PSO3009\DBR_WEEK_124\RE_WEEK_124_CSR\PROD\TEFPASI01.SAS] 01OCT2015, 14:16

TABLE 11

Number of Visits for Which Subjects Achieved a PAST 75 Response from Week 88 through Week 112; Subjects Randomized to Ustekinumab Subject-tailored Interval Maintenance Regimen at Week 28 (Study CNT01275P503009)

| | Group 2 ustekinumab subject-tailored interval maintenance regimen | | | | |
|---|---|---|---|---|---|
| | q12 w | q16 w | q20 w | q24 w | All randomized subjects |
| Analysis set: subjects assigned to ustekinumab subject-tailored interval maintenance regimen at Week 28 | 84 | 61 | 51 | 84 | 302 |
| N[a] | 84 | 61 | 51 | 84 | 302 |
| Mean (SD) | 4.7 (3.03) | 5.2 (2.73) | 5.6 (2.37) | 6.3 (1.67) | 5.4 (2.61) |
| 95% confidence interval of mean[b] | (4.07; 5.38) | (4.53; 5.93) | (4.92; 6.25) | (5.97; 6.70) | (5.15; 5.74) |
| Median | 7.0 | 7.0 | 7.0 | 7.0 | 7.0 |
| Range | (0; 7) | (0; 7) | (0; 7) | (0; 7) | (0; 7) |

| | Group 1 ustekinumab q12 w maintenance regimen | | | Group 2 ustekinumab subject-tailored interval maintenance regimen | |
|---|---|---|---|---|---|
| IQ range | (1.0; 7.0) | (3.0; 7.0) | (5.0; 7.0) | (7.0; 7.0) | (5.0; 7.0) |
| Number of visits for which subjects with a PASI 75 response | | | | | |
| 0 | 20 (23.8%) | 9 (14.8%) | 5 (9.8%) | 3 (3.6%) | 43 (14.2%) |
| 1 | 3 (3.6%) | 1 (1.6%) | 2 (3.9%) | 1 (1.2%) | 7 (2.3%) |
| 2 | 3 (3.6%) | 4 (6.6%) | 1 (2.0%) | 0 | 8 (2.6%) |
| 3 | 0 | 2 (3.3%) | 0 | 3 (3.6%) | 5 (1.7%) |
| 4 | 2 (2.4%) | 3 (4.9%) | 2 (3.9%) | 2 (2.4%) | 9 (3.0%) |
| 5 | 2 (2.4%) | 0 | 4 (7.8%) | 5 (6.0%) | 11 (3.6%) |

TABLE 11-continued

Number of Visits for Which Subjects Achieved a PAST 75 Response from Week 88 through Week 112; Subjects Randomized to Ustekinumab Subject-tailored Interval Maintenance Regimen at Week 28 (Study CNT01275P503009)

| | | | | | |
|---|---|---|---|---|---|
| 6 | 8 (9.5%) | 2 (3.3%) | 6 (11.8%) | 1 (1.2%) | 17 (5.6%) |
| 7 | 46 (54.8%) | 40 (65.6%) | 31 (60.8%) | 69 (82.1%) | 202 (66.9%) |

[a]After applying treatment failure rules, subjects with any missing data between Weeks 88 and 112 were handled as follows:
(1) If a missing visit was intermittent, the missing value was imputed with the weighted average relative to the distance of the available values before and after the missing visit (a linear relationship is assumed across the visits).
(2) If a missing visit was not intermittent, i.e., there were no data available after the missing visit, a last observation carried forward method was used to impute the missing data.
[b]95% confidence interval was based on normal approximation.
[TEFPASI04.RTF] [CNTO1275\PSO3009\DBR_WEEK_124\RE_WEEK_124_CSR\PROD\TEFPASI04.SAS] 01OCT2015, 14:16

TABLE 12

Summary of Key Safety Findings from Week 28 Through Week 124; Treated Subjects Randomized at Week 28 (Study CNTO1275PSO3009)

| | Group 1 ustekinumab q12w maintenance regimen | Group 2 ustekinumab subject-tailored interval maintenance regimen | | | | | |
|---|---|---|---|---|---|---|---|
| | | All randomized subjects | q12w | q16w | q20w | q24w | Total |
| Analysis set: treated subjects randomized at Week 28 | 76 | 302 | 84 | 61 | 51 | 84 | 378 |
| Avg duration of follow-up (wks) | 85.9 | 84.2 | 87.2 | 89.9 | 90.1 | 90.9 | 84.6 |
| Avg exposure (number of administrations) for injections at or after Week 28 | 14.6 | 14.6 | 15.3 | 15.7 | 15.7 | 15.9 | 14.6 |
| Subjects who discontinued study agent because of 1 or more adverse events | 5 (6.6%) | 17 (5.6%) | 5 (6.0%) | 3 (4.9%) | 2 (3.9%) | 3 (3.6%) | 22 (5.8%) |
| Subjects with 1 or more: | | | | | | | |
| Adverse events | 55 (72.4%) | 220 (72.8%) | 62 (73.8%) | 54 (88.5%) | 35 (68.6%) | 62 (73.8%) | 275 (72.8%) |
| Serious adverse events | 7 (9.2%) | 21 (7.0%) | 6 (7.1%) | 2 (3.3%) | 2 (3.9%) | 9 (10.7%) | 28 (7.4%) |
| Overall infections | 37 (48.7%) | 138 (45.7%) | 45 (53.6%) | 38 (62.3%) | 19 (37.3%) | 35 (41.7%) | 175 (46.3%) |
| Serious infections | 0 | 3 (1.0%) | 2 (2.4%) | 0 | 1 (2.0%) | 0 | 3 (0.8%) |
| Requiring treatment | 18 (23.7%) | 70 (23.2%) | 22 (26.2%) | 20 (32.8%) | 12 (23.5%) | 15 (17.9%) | 88 (23.3%) |
| Malignancy | 3 (3.9%) | 7 (2.3%) | 3 (3.6%) | 1 (1.6%) | 1 (2.0%) | 1 (1.2%) | 10 (2.6%) |
| MACE* | 0 | 2 (0.7%) | 0 | 0 | 0 | 2 (2.4%) | 2 (0.5%) |

*MACE: myocardial infarction (MI), stroke or CV death

What is claimed is:

1. A method of treating psoriasis in a a patient using an increasing dosing or maintenance interval, comprising administering a pharmaceutical composition comprising an antibody to both IL-12 and IL-23 to the patient, wherein the antibody comprises a heavy chain variable amino acid sequence of SEQ ID NO: 7 and a light chain variable amino acid sequence of SEQ ID NO: 8, in an initial dose, a dose 4 weeks after the initial dose and a dose once every 12 weeks for 24 weeks after administration of the initial dose and increasing the dosing interval 28 weeks after administration of the initial dose to a dosing interval of every 24 weeks after identifying the patient as a responder to the antibody 28 weeks after administration of the initial dose, wherein the dose is 45 mg or 90 mg.

2. The method of claim 1, wherein the step of identifying the patient as a responder to the antibody comprises measuring and identifying the patient as having a PASI75 or PGA 0 or 1 score.

3. The method of claim 1, wherein the antibody to IL-12 and IL-23 administered to the patient is ustekinumab.

4. The method of claim 1, wherein the patient does not show an increased risk of immunogenicity.

5. The method of claim 1, wherein the patient has a PASI75, PASI90 or PGA 0 or 1 score 28 weeks after initial treatment.

6. The method of claim 1, wherein the patient has a PASI75, PASI90 or PGA 0 or 1 score 52 weeks after initial treatment.

7. The method of claim 1, wherein the patient has a PASI75, PASI90 or PGA 0 or 1 score 108, 112 and/or 116 weeks after initial treatment.

8. The method of claim 1, wherein the antibody comprises the heavy chain variable region amino acid sequence of SEQ ID NO: 7 and the light chain variable region amino acid sequence of SEQ ID NO: 8 and comprises about 0.53 mg L-histidine per ml of the pharmaceutical composition; about 1.37 mg L-histidine monohydrochloride monohydrate per ml of the pharmaceutical composition; about 0.04 mg polysorbate 80 per ml of the pharmaceutical composition; about 76 mg of sucrose per ml of the pharmaceutical composition; and water as a diluent at standard state.

9. A method of treating psoriasis in a patient using an an increasing dosing or maintenance interval, comprising administering a pharmaceutical composition comprising an antibody to both IL-12 and IL-23 to the patient in an initial dose, a dose 4 weeks after the initial dose and a dose once every 12 weeks for 24 weeks after administration of the initial dose and increasing the dosing interval 28 weeks after administration of the initial dose to a dosing interval of every 24 weeks after identifying the patient as a responder to the antibody 28 weeks after administration of the initial dose, wherein the dose is 45 mg or 90 mg, and wherein the antibody comprises the heavy chain CDR amino acid sequences of SEQ ID NO: 1, SEQ ID NO: 2, and SEQ ID NO: 3; and the light chain CDR amino acid sequences of SEQ ID NO: 4, SEQ ID NO: 5, and SEQ ID NO: 6 and comprises about 0.53 mg L-histidine per ml of the pharmaceutical composition; about 1.37 mg L-histidine monohydrochloride monohydrate per ml of the pharmaceutical composition; about 0.04 mg polysorbate 80 per ml of the pharmaceutical composition; about 76 mg of sucrose per ml of the pharmaceutical composition; and water as a diluent at standard state.

* * * * *